US006248086B1

(12) United States Patent
Sweezer et al.

(10) Patent No.: US 6,248,086 B1
(45) Date of Patent: *Jun. 19, 2001

(54) METHOD FOR CANNULATING A PATIENT'S AORTIC ARCH AND OCCLUDING THE PATIENT'S ASCENDING AORTIC ARCH

(75) Inventors: William Penn Sweezer, Lafayette; James Jimison, Palo Alto; Ronald L. Coleman, Sunnyvale, all of CA (US)

(73) Assignee: Heartport, Inc., Redwood City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/027,942

(22) Filed: Feb. 23, 1998

Related U.S. Application Data

(63) Continuation of application No. 08/580,076, filed on Dec. 20, 1995, now Pat. No. 5,800,375, which is a continuation of application No. 08/250,721, filed on May 27, 1994, now Pat. No. 5,478,309.

(51) Int. Cl.[7] .................................................. A61M 29/00

(52) U.S. Cl. ...................... 604/4.01; 604/6.14; 604/6.16; 604/96; 604/101; 604/102

(58) Field of Search ............................ 604/4–6, 506–509, 604/4.01, 6.09, 6.1, 6.11, 6.13, 6.14, 6.16, 96, 101, 102; 600/16–18

(56) References Cited

U.S. PATENT DOCUMENTS

| Re. 33,258 | 7/1990 | Onik et al. . |
| 2,308,484 | 1/1943 | Auzin et al. . |
| 2,854,982 | 10/1958 | Pagano . |

(List continued on next page.)

FOREIGN PATENT DOCUMENTS

| 2246526 | 3/1973 | (DE) . |
| 0 161 045 | 11/1985 | (EP) . |

(List continued on next page.)

OTHER PUBLICATIONS

Baxter Healthcare Corporation, "Fogarty Occlusion Catheter: Instructions for Use," ©1994.

(List continued on next page.)

Primary Examiner—Dennis Ruhl
(74) Attorney, Agent, or Firm—Jens E. Hoekendijk

(57) ABSTRACT

A catheter system and method for achieving total cardiopulmonary bypass during heart surgery. A venous perfusion catheter is inserted peripherally into a preselected vein where it is advanced and positioned at the atrio-caval junction. The venous perfusion catheter has first and second balloons which when inflated respectively occlude the inferior and superior vena cava thereby precluding blood flow into the right atrium. An arterial perfusion catheter is inserted peripherally into a preselected arterial vessel and advanced within the vessel and positioned in the ascending aorta cephalid of the junction of the coronary arteries with the aortic root. A second flexible arterial cannula is mounted in sliding relationship with the first flexible cannula and carries an inflatable balloon adjacent its distal end to provide for occlusion of the ascending aorta. A first flexible cannula has a first lumen and an arterial venting orifice communicating with the first lumen defining a single flow path for the passage of cardioplegia solution to arrest the heart or for the evacuation of blood from the aortic root. A third lumen extends axially through the first flexible arterial cannula and communicates with a multiplicity of openings in the distal tip of the cannula defining a flow path for suctioning blood from the left ventricle. The second flexible cannula of the arterial perfusion catheter has a first cavity extending axially therethrough that communicates with an opening at its distal tip to permit the passage of blood delivered by the cardiopulmonary bypass pump into arterial circulation.

6 Claims, 33 Drawing Sheets

U.S. PATENT DOCUMENTS

| | | |
|---|---|---|
| 3,385,300 | 5/1968 | Holter . |
| 3,635,223 | 1/1972 | Klieman . |
| 3,674,014 | 7/1972 | Tillander . |
| 3,692,018 | 9/1972 | Goetz et al. . |
| 3,766,924 | 10/1973 | Pidgeon . |
| 3,769,960 | 11/1973 | Robinson . |
| 3,788,328 | 1/1974 | Alley et al. . |
| 3,833,003 | 9/1974 | Taricco . |
| 3,837,347 | 9/1974 | Tower . |
| 3,851,647 | 12/1974 | Monestere, Jr. et al. . |
| 3,889,686 | 6/1975 | Duturbure . |
| 3,903,895 | 9/1975 | Alley et al. . |
| 3,915,171 | 10/1975 | Shermeta . |
| 3,963,028 | 6/1976 | Cooley et al. . |
| 3,970,090 | 7/1976 | Loiacono . |
| 3,983,879 | 10/1976 | Todd . |
| 4,000,739 | 1/1977 | Stevens . |
| 4,019,515 | 4/1977 | Kornblum et al. . |
| 4,029,104 | 6/1977 | Kerber . |
| 4,073,297 | 2/1978 | Kopp . |
| 4,122,858 | 10/1978 | Schiff . |
| 4,154,227 | 5/1979 | Krause et al. . |
| 4,173,981 | 11/1979 | Mortensen . |
| 4,204,328 | 5/1980 | Kutner . |
| 4,248,224 | 2/1981 | Jones . |
| 4,276,874 | 7/1981 | Wolvek et al. . |
| 4,284,073 | 8/1981 | Krause et al. . |
| 4,285,341 | 8/1981 | Pollack . |
| 4,287,892 | 9/1981 | Schiff . |
| 4,289,129 | 9/1981 | Turner . |
| 4,290,428 | 9/1981 | Durand et al. . |
| 4,301,803 | 11/1981 | Handa et al. . |
| 4,304,239 | 12/1981 | Perlin . |
| 4,310,017 | 1/1982 | Raines . |
| 4,323,071 | 4/1982 | Simpson et al. . |
| 4,327,709 | 5/1982 | Hanson et al. . |
| 4,328,056 | 5/1982 | Snooks . |
| 4,351,341 | 9/1982 | Goldberg et al. . |
| 4,405,313 | 9/1983 | Sisley et al. . |
| 4,411,055 | 10/1983 | Simpson et al. . |
| 4,413,989 | 11/1983 | Schjeldahl et al. . |
| 4,417,576 | 11/1983 | Baran . |
| 4,430,081 | 2/1984 | Timmermans . |
| 4,439,186 | 3/1984 | Kuhl . |
| 4,441,495 | 4/1984 | Hicswa . |
| 4,451,251 | 5/1984 | Osterholm . |
| 4,456,000 | 6/1984 | Schjeldahl et al. . |
| 4,459,977 | 7/1984 | Pizon et al. . |
| 4,464,175 | 8/1984 | Altman et al. . |
| 4,493,697 | 1/1985 | Krause et al. . |
| 4,496,345 | 1/1985 | Hasson . |
| 4,497,325 | 2/1985 | Wedel . |
| 4,512,762 | 4/1985 | Spears . |
| 4,527,549 | 7/1985 | Gabbay . |
| 4,531,935 | 7/1985 | Berryessa . |
| 4,531,936 | 7/1985 | Gordon . |
| 4,535,757 | 8/1985 | Webster, Jr. . |
| 4,540,399 | 9/1985 | Litzie et al. . |
| 4,552,558 | 11/1985 | Muto . |
| 4,573,966 | 3/1986 | Weikl et al. . |
| 4,580,568 | 4/1986 | Gianturco . |
| 4,592,340 | 6/1986 | Boyles . |
| 4,596,552 | 6/1986 | DeVries . |
| 4,601,706 | 7/1986 | Aillon . |
| 4,601,713 | 7/1986 | Fuqua . |
| 4,610,661 | 9/1986 | Possis et al. . |
| 4,631,052 | 12/1986 | Kensey . |
| 4,639,252 | 1/1987 | Kelly et al. . |
| 4,648,384 | 3/1987 | Schmukler . |
| 4,664,125 | 5/1987 | Pinto . |
| 4,681,117 | 7/1987 | Brodman et al. . |
| 4,686,085 | 8/1987 | Osterholm . |
| 4,689,041 | 8/1987 | Corday et al. . |
| 4,692,148 | 9/1987 | Kantrowitz et al. . |
| 4,697,574 | 10/1987 | Karcher et al. . |
| 4,704,102 | 11/1987 | Guthery . |
| 4,705,507 | 11/1987 | Boyles . |
| 4,714,460 | 12/1987 | Calderon . |
| 4,721,109 | 1/1988 | Healey . |
| 4,722,347 | 2/1988 | Abrams et al. . |
| 4,722,732 | 2/1988 | Martin . |
| 4,723,550 | 2/1988 | Bales et al. . |
| 4,723,936 | 2/1988 | Buchbinder et al. . |
| 4,741,328 | 5/1988 | Gabby . |
| 4,751,924 | 6/1988 | Hammerschmidt et al. . |
| 4,753,637 | 6/1988 | Horneffer . |
| 4,767,409 | 8/1988 | Brooks . |
| 4,770,652 | 9/1988 | Mahurkar . |
| 4,771,777 | 9/1988 | Horzewski et al. . |
| 4,777,951 | 10/1988 | Cribier et al. . |
| 4,785,795 | 11/1988 | Singh . |
| 4,787,899 | 11/1988 | Lazarus . |
| 4,787,901 | 11/1988 | Baykut . |
| 4,790,825 | 12/1988 | Bernstein et al. . |
| 4,794,928 | 1/1989 | Kletschka . |
| 4,796,629 | 1/1989 | Grayzel . |
| 4,798,588 | 1/1989 | Aillon . |
| 4,804,358 | 2/1989 | Karcher et al. . |
| 4,804,365 | 2/1989 | Litzie et al. . |
| 4,808,165 | 2/1989 | Carr . |
| 4,809,681 | 3/1989 | Kantrowitz et al. . |
| 4,811,737 | 3/1989 | Rydell . |
| 4,821,722 | 4/1989 | Miller et al. . |
| 4,830,849 | 5/1989 | Osterholm . |
| 4,848,344 | 7/1989 | Sos et al. . |
| 4,850,969 | 7/1989 | Jackson . |
| 4,865,581 | 9/1989 | Lindquist et al. . |
| 4,877,031 | 10/1989 | Conway et al. . |
| 4,877,035 | 10/1989 | Bogen et al. . |
| 4,878,495 | 11/1989 | Grayzel . |
| 4,883,458 | 11/1989 | Shiber . |
| 4,886,507 | 12/1989 | Patton et al. . |
| 4,889,137 | 12/1989 | Kolobow . |
| 4,898,168 | 2/1990 | Yule . |
| 4,902,272 | 2/1990 | Milder et al. . |
| 4,902,273 | 2/1990 | Choy et al. . |
| 4,911,163 | 3/1990 | Fina . |
| 4,917,667 | 4/1990 | Jackson . |
| 4,923,450 | 5/1990 | Maeda et al. . |
| 4,927,412 | 5/1990 | Menasche . |
| 4,934,996 | 6/1990 | Mohl et al. . |
| 4,943,275 | 7/1990 | Stricker . |
| 4,943,277 | 7/1990 | Bolling . |
| 4,960,412 | 10/1990 | Fink . |
| 4,966,604 | 10/1990 | Reiss . |
| 4,969,470 | 11/1990 | Mohl et al. . |
| 4,979,939 | 12/1990 | Shiber . |
| 4,985,014 | 1/1991 | Orejola . |
| 4,986,830 | 1/1991 | Owens et al. . |
| 4,990,143 | 2/1991 | Sheridan . |
| 4,994,032 | 2/1991 | Sugiyama et al. . |
| 4,994,033 | 2/1991 | Shockey et al. . |
| 5,007,896 | 4/1991 | Shiber . |
| 5,009,636 | 4/1991 | Wortley et al. . |
| 5,011,468 | 4/1991 | Lundquist et al. . |
| 5,011,469 | 4/1991 | Buckberg et al. . |
| 5,011,488 | 4/1991 | Ginsburg . |
| 5,013,296 | 5/1991 | Buckberg et al. . |
| 5,021,044 | 6/1991 | Sharkaway . |
| 5,021,045 | 6/1991 | Buckberg et al. . |
| 5,024,668 | 6/1991 | Peters et al. . |

| | | |
|---|---|---|
| 5,026,366 | 6/1991 | Leckrone . |
| 5,033,998 | 7/1991 | Corday et al. . |
| 5,041,093 | 8/1991 | Chu . |
| 5,041,098 | 8/1991 | Loiterman et al. . |
| 5,047,041 | 9/1991 | Samuels . |
| 5,049,132 | 9/1991 | Schaffer et al. . |
| 5,053,008 | 10/1991 | Bajaj . |
| 5,059,167 | 10/1991 | Lundquist et al. . |
| 5,069,661 | 12/1991 | Trudell . |
| 5,069,662 | 12/1991 | Bodden . |
| 5,073,168 | 12/1991 | Danforth . |
| 5,088,984 | 2/1992 | Fields . |
| 5,089,015 | 2/1992 | Ross . |
| 5,090,960 | 2/1992 | Michael . |
| 5,106,368 | 4/1992 | Uldall et al. . |
| 5,109,859 | 5/1992 | Jenkins . |
| 5,112,305 | 5/1992 | Barath et al. . |
| 5,116,305 | 5/1992 | Milder et al. . |
| 5,125,903 | 6/1992 | McLaughlin et al. . |
| 5,152,771 | 10/1992 | Sabbaghian et al. . |
| 5,167,628 | 12/1992 | Boyles . |
| 5,171,232 | 12/1992 | Castillo et al. . |
| 5,176,619 | 1/1993 | Segalowitz . |
| 5,181,518 | 1/1993 | McDonagh . |
| 5,186,713 | 2/1993 | Raible . |
| 5,195,942 | 3/1993 | Weil et al. . |
| 5,197,952 | 3/1993 | Marcadis et al. . |
| 5,216,032 | 6/1993 | Manning . |
| 5,219,326 | 6/1993 | Hattler . |
| 5,226,427 | 7/1993 | Buckberg et al. . |
| 5,236,413 | 8/1993 | Feiring . |
| 5,246,007 | 9/1993 | Frisbie et al. . |
| 5,250,038 | 10/1993 | Melker et al. . |
| 5,250,069 | 10/1993 | Nobuyoshi et al. . |
| 5,254,089 | 10/1993 | Wang . |
| 5,254,097 | 10/1993 | Schock et al. . |
| 5,270,005 | 12/1993 | Raible . |
| 5,275,622 | 1/1994 | Lazarus et al. . |
| 5,290,231 | 3/1994 | Marcadis et al. . |
| 5,295,958 | 3/1994 | Shturman . |
| 5,308,320 | 5/1994 | Safar et al. . |
| 5,312,344 | 5/1994 | Grinfeld et al. . |
| 5,314,418 | 5/1994 | Takano et al. . |
| 5,322,500 | 6/1994 | Rickerd . |
| 5,322,509 | 6/1994 | Johnson et al. . |
| 5,324,260 | 6/1994 | O'Neill et al. . |
| 5,330,451 | 7/1994 | Gabbay . |
| 5,334,142 | 8/1994 | Paradis . |
| 5,370,618 | 12/1994 | Leonhardt . |
| 5,370,640 | 12/1994 | Kolff . |
| 5,374,245 | 12/1994 | Mahurkar . |
| 5,380,282 | 1/1995 | Burns . |
| 5,382,239 | 1/1995 | Orr et al. . |
| 5,383,854 | 1/1995 | Safar et al. . |
| 5,385,548 | 1/1995 | Williams et al. . |
| 5,395,330 | 3/1995 | Marcadis et al. . |
| 5,395,331 | 3/1995 | O'Neill et al. . |
| 5,397,306 | 3/1995 | Nobuyoshi et al. . |
| 5,411,027 | 5/1995 | Wiklund et al. . |
| 5,411,479 | 5/1995 | Bodden . |
| 5,411,552 | 5/1995 | Andersen et al. . |
| 5,421,825 | 6/1995 | Farcot . |
| 5,425,708 | 6/1995 | Nasu . |
| 5,428,070 | 6/1995 | Cooke et al. . |
| 5,433,700 | 7/1995 | Peters . |
| 5,437,633 | 8/1995 | Manning . |
| 5,439,443 | 8/1995 | Miyata et al. . |
| 5,443,446 | 8/1995 | Shturman . |
| 5,451,207 | 9/1995 | Yock . |
| 5,456,665 | 10/1995 | Postell et al. . |
| 5,458,574 | 10/1995 | Machold et al. . |
| 5,478,309 | 12/1995 | Sweezer et al. . |
| 5,487,730 | 1/1996 | Marcadis et al. . |
| 5,499,996 | 3/1996 | Hill . |
| 5,505,698 | 4/1996 | Booth et al. . |
| 5,509,897 | 4/1996 | Twardowski et al. . |
| 5,525,388 | 6/1996 | Wand et al. . |
| 5,527,292 | 6/1996 | Adams et al. . |
| 5,533,957 | 7/1996 | Aldea . |
| 5,562,606 | 10/1996 | Huybregts . |
| 5,578,010 | 11/1996 | Ashby . |
| 5,584,803 | 12/1996 | Stevens et al. . |
| 5,591,129 | 1/1997 | Shoup et al. . |
| 5,595,181 | 1/1997 | Hubbard . |
| 5,597,377 | 1/1997 | Aldea . |
| 5,599,329 | 2/1997 | Gabbay . |
| 5,800,375 * | 9/1998 | Sweezer et al. .................. 604/4 |

FOREIGN PATENT DOCUMENTS

| | | |
|---|---|---|
| 0 218 275 | 4/1987 | (EP) . |
| 0 238 106 | 9/1987 | (EP) . |
| 0 249 338 | 12/1987 | (EP) . |
| 0 277 367 | 8/1988 | (EP) . |
| 0 321 614 | 6/1989 | (EP) . |
| 0 335 205 | 10/1989 | (EP) . |
| 0 414 350 | 2/1991 | (EP) . |
| 1097881 | 1/1968 | (GB) . |
| 1097882 | 1/1968 | (GB) . |
| 1284701 | 8/1972 | (GB) . |
| 1414344 | 11/1975 | (GB) . |
| 1467976 | 3/1977 | (GB) . |
| 1477665 | 6/1977 | (GB) . |
| 1513918 | 6/1978 | (GB) . |
| 334404 | 1/1936 | (IT) . |
| 1271508 | 11/1986 | (SU) . |
| 1371701 | 2/1988 | (SU) . |
| WO 81/03613 | 12/1981 | (WO) . |
| WO 83/03204 | 9/1983 | (WO) . |
| WO 89/10155 | 11/1989 | (WO) . |
| WO 91/01689 | 2/1991 | (WO) . |
| WO 91/08791 | 6/1991 | (WO) . |
| WO 91/10456 | 7/1991 | (WO) . |
| WO 91/17720 | 11/1991 | (WO) . |
| WO 92/17118 | 10/1992 | (WO) . |
| WO 93/07927 | 4/1993 | (WO) . |
| WO 95/30447 | 11/1995 | (WO) . |

OTHER PUBLICATIONS

Buckberg, G.D., "Strategies and Logic of Cardioplegic Delivery to Prevent, Avoid, and Reverse Ischemic and Reperfusion Damage," *J Thorac Vasc Surg,* 1987; 93:127–129.

Corday et al., "Symposium on the Present Status of Reperfusion of the Acutely Ischemic Myocardium. Part I," *J. Am Coll Cardiol,* 1983; 1(4):1031–1036.

Cosgrove, "Management of the Calcified Aorta: An Alternative Method of Occlusion," *Ann Thorac Surg,* 1983;36:718–719.

Crooke et al., "Biventricular Distribution of Cold Blood Cardioplegic Solution Administered by Different Retrograde Techniques," *J Cardiac Thorac Surg,* 1991;102(4):631–636.

Datascope FDA 510(k) Application, "PERCLUDER–DL Occluding Balloon," Oct. 12, 1993.

Derwent Abstract No. 87–190867/27 (1987), SU 127508 (Gorki Kirov Medical Ins.).

DLP, Inc., Directions for Use: Cardioplegic Pressure Cannula with Vent Line, Code #24009 9 Gauge (no date).

DLP Medtronic Alternative Access Cannulae Brochure, ©1995.

DLP Worldwide Medical Innovations, Instrument Listings, pp. 5–9.

Douville et al., "Retrograde Versus Antegrade Cardioplegia: Impact on Right Ventricular Function," *Ann Thorac Surg*, 1992; 54:56–61.

Drinkwater et al., "The Use of Combined Antegrade–Retrograde Infusion of Blood Cardioplegic Solution in Pediatric Patients Undergoing Heart Operations," *Thorac and Cardiovascular Surg*, 1992; 104(5):1349–1355.

Elecath, "Baim Coronary Sinus Flow Catheter for Jugular or Subclavian Entry," Catalog No. 75–2337, 1994.

Erath and Stoney, "Balloon Catheter Occlusion of the Ascending Aorta," *Ann Thorac Surg*, 1983;35:560–561.

Farcot et al., "New Catheter–Pump System for Diastolic Synchronized Coronary Sinus Retroperfusion (D.S.R.)," *Med Prog Technol*, 1980; 8(1):29–37.

Farcot et al., "Synchronized Retroperfusion of Coronary Veins for Circulatory Support of Jeopardized Ischemic Myocardium," *Am J Cardiol*, 1978; 41:1101–1201.

Foster and Threlkel, "Proximal Control of Aorta with a Balloon Catheter," *Surg Gynecology & Obstetrics*, 1971, pp. 693–694.

Gundry et al., "A Comparison of Retrograde of Cardioplegia Versus Antegrade Cardioplegia in the Presence of Coronary Artery Obstruction," *Ann Thorac Surg*, 1984; 38(2):124–127.

Gundry, "Modification of Myocardial Ischemic in Normal and Hypertrophied Hearts Utilizing Diastolic Retroperfusion of the Coronary Veins," *J Thorac Cardiovasc Surg*, 1982; 83:659–669.

Haendchen et al., "Prevention of Ischemic Injury and Early Reperfusion Derangements by Hypothermic Retroperfusion," *J Am Coll Cardiol*, 1983; 1(4):1067–1080.

Hammond et al., "Retrograde Coronary Sinus Perfusion: A Method of Myocardial Protection in the Dog During Left Coronary Artery Occlusion," *Ann Surg*, 1967; 166(1):139–147.

Ishizaka, "Myocardial Protection by Retrograde Cardiac Perfusion with Cold Medified Krebs Solution through Coronary Sinus During Complete Ischemic Arrest for 120 Minutes," *J Jpn Assn Thorac Surg*, 1977;25(12);:1592–1601.

Kalmbach et al., "Cardioplegia Delivery by Combined Aortic Root and Coronary Sinus Perfusion," *Ann Thorac Surg*, 1989; 47:316–317.

Kar and Nordlander, "Coronary Veins: An Alternate Route to Ischemic Myocardium," *Heart and Lung*, Mar. 1992, vol. 21, No. 2, pp. 148–155.

Leggett et al., "Fiberoptic Cardioscopy Under Cardiopulmonary Bypass: Potential for Cardioscopy Surgery?" *Ann Thorac Surg*, 1994;58:222–225.

Lust et al., "Improved Protection of Chronically Inflow–limited Myocardium with Retrograde Coronary Sinus Cardioplegia," *Circulation III*, 1988;78(5):217–223.

Markov et al., "Reversal of Acute Myocardial Ischemia in Closed Chest Animals by Retrograde Perfusion of the Coronary Sinus with Arterial Blood," *Acta Cardiologica*, 1976; XXXI(3):185–199.

Medex, Inc. Product Brochure, Angioplasty Kits and Accessories and PTCA Valve, 1990.

Medex, Inc., MX220 Single Tuohy–Borst Adaptor: Instructions for Use, 1992.

Medi–Tech, Boston Scientific Corporation, "Occlusion Balloon Catheters: Instructions for Use," Rev. Jun., 1991.

Medtronic Bio–Medicus, Inc., "Bio–Medicus Cannula Instructions for Use Manual, Sterile and Non–Pyrogenic Single–Use Only," PN 85281 Rev C(10–91).

Medtronic Bio–Medicus, Inc., "Bio–Medicus Cannula Introducer Instructions for Use Manual," PN 85146–Rev. C(7/91).

Medtronic Bio–Medicus Femoral Cannulae advertisement, ©1991.

Medtronic Bio–Medicus Pediatric Cannulae advertisement, ©1991.

Medtronic Bio–Medicus Percutaneous Cannula Kits advertisements, ©1991.

Meerbaum et al., "Diastolic Retroperfusion of Acutely Ischemic Myocardium," *Am J Cardiol*, 1976; 37:588–598.

Meerbaum et al., "Hypothermic Coronary Venous Phased Retroperfusion: A Closed–Chest Treatment of Acute Regional Myocardial Ischemia," *Circulation*, 1982; 65(7): 1435–1445.

Meerbaum et al., "Retrograde Lysis of Coronary Artery Thrombus by Coronary Venouse Strepokinase Administration," *J Am Coll Cardiol*, 1983; 1(5):1262–1267.

Menasche et al., "Cardioplegia by Way of the coronary Sinus for Valvular and Coronary Surgery," *JACC*, 1991; 18(2):628–636.

Menasche et al., "Retrograde Cardioplegia through the Coronary Sinus," *Ann Thorac Surg*, 1987; 44:214–216.

Menasche et al., "Retrograde Coronary Sinus Cardioplegia for Aortic Valve Operations: A Clinical Report on 500 Patients," *Ann Thorac Surg*, 1990; 49:556–564.

Menasche et al., "Retrograde Warm Blood Cardioplegia Preserves Hypertrophied Myocardium: A Clinical Study," *Ann Thorac Surg*, 1994; 57:1429–1435.

"Valvular Heart Disease," Merck Manual of Diagnosis and Therapy, sixteenth ed, 1992, pp. 546–553.

Ogawa, K. "Aortic Arch Reconstruction Without Aortic Cross–Clamping Using Separate Extracorporeal Circulation," *J Jpn Assn Thorac Surg*, 1993; pp. 2185–2190.

Okita et al., "Utilization of Triple–Lumen Balloon Catheter for Occlusion of the Ascending Aorta During Distal Aortic Arch Surgery with Hypothermic Retrograde Cerebral Circulation Technique Through Left Thoracotomy," *Journal of Cardiac Surgery*, 1996; 10:699–702.

Peters, W. S., "The Promise of Cardioscopic Surgery," *AustralAs J Cardiac Thorac Surg*, 1993; 2(3):152–154.

Pilling Surgical Instruments, Vascular Clamps—Cooley Brochure, p. 385 (no date).

Razi, D..M., "The Challenge of Calcific Aortitis," *J Cardiac Surg*, 1993; 8:102–107.

Research Medical, Inc., Cardioplegia Products, Product Catalog 1995.

Research Medical, Inc., Fem Flex Femoral Percutaneous Cannulae, advertisement, *Ann Thorac Surg*, Jan., 1995, p. A38.

Ropchan et al., "Salvage of Ischemic Myocardium by Non-synchronized Retroperfusion in the Pig," *The Journal of Thoracic and Cardiovascular Surgery*, Sep. 1992, vol. 104, No. 3, pp. 619–625.

Rossi, "Long–term Cardiopulmonary Bypass by Peripheral Cannulation in a Model of Total Heart Failure," *J Thorac Cardiac Vasc Surg*, 1990;100:914–921.

Sabiston, D.C., Textbook of Surgery, 10$^{th}$ Ed., 1972, pp. 2021–2023, 2114–2121.

Sakaguchi et al, "Aortic Valve Replacement and Coronary Artery Bypass," *J Jpn Assoc for Thoracic Surg,* 1993;41(6):1063–1068.

Shumway, "Forward Versus Retrograde Coronary Perfusion for Direct Vision Surgery of Acquired Aortic Valvular Disease," *J Thoracic and Cardiovasc Surg,* 1959; 75–80.

Takahashi, M., "Retrograde Coronary Sinus Perfusion for Myocardial protection in Aortic A valve Surgery," *J Jpn Assn Thorac Surg,* 1982;30(3):306–318.

Uchida et al, "Percutaneous Cardiomyotomy ad Valvulotomy with Angioscopic Guidance," *American Heart Journal,* 1991;121(4, part I):1221–1224.

Uchida et al., "Percutaneous Fiberoptic Angioscopy of the Cardiac Valves," *Am Heart J,* 1991;121(6, part I):1791–1798.

Yamaguchi, A., "A Case of Reoperation Using a Balloon Catheter with Blocked Pars Ascendes Aortae," *Kyobu Geka,* 1991; 42(11):961–964.

* cited by examiner

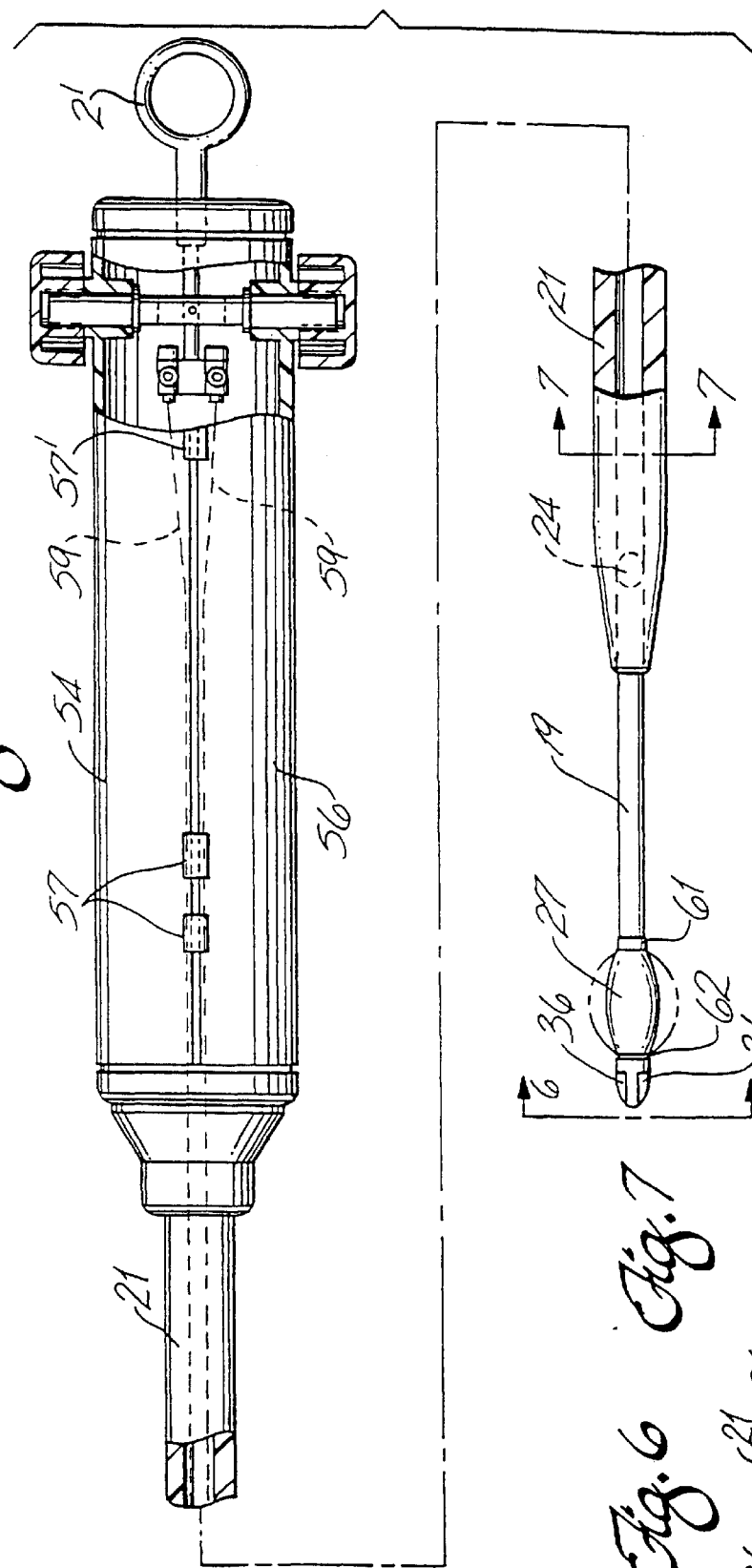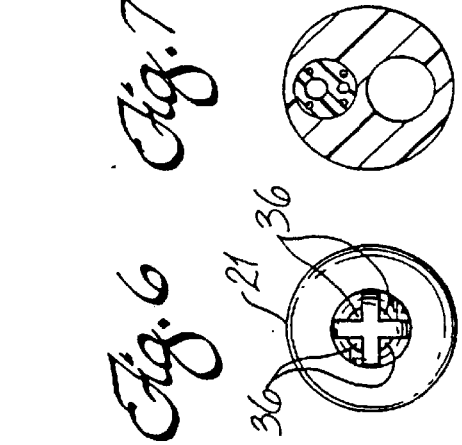

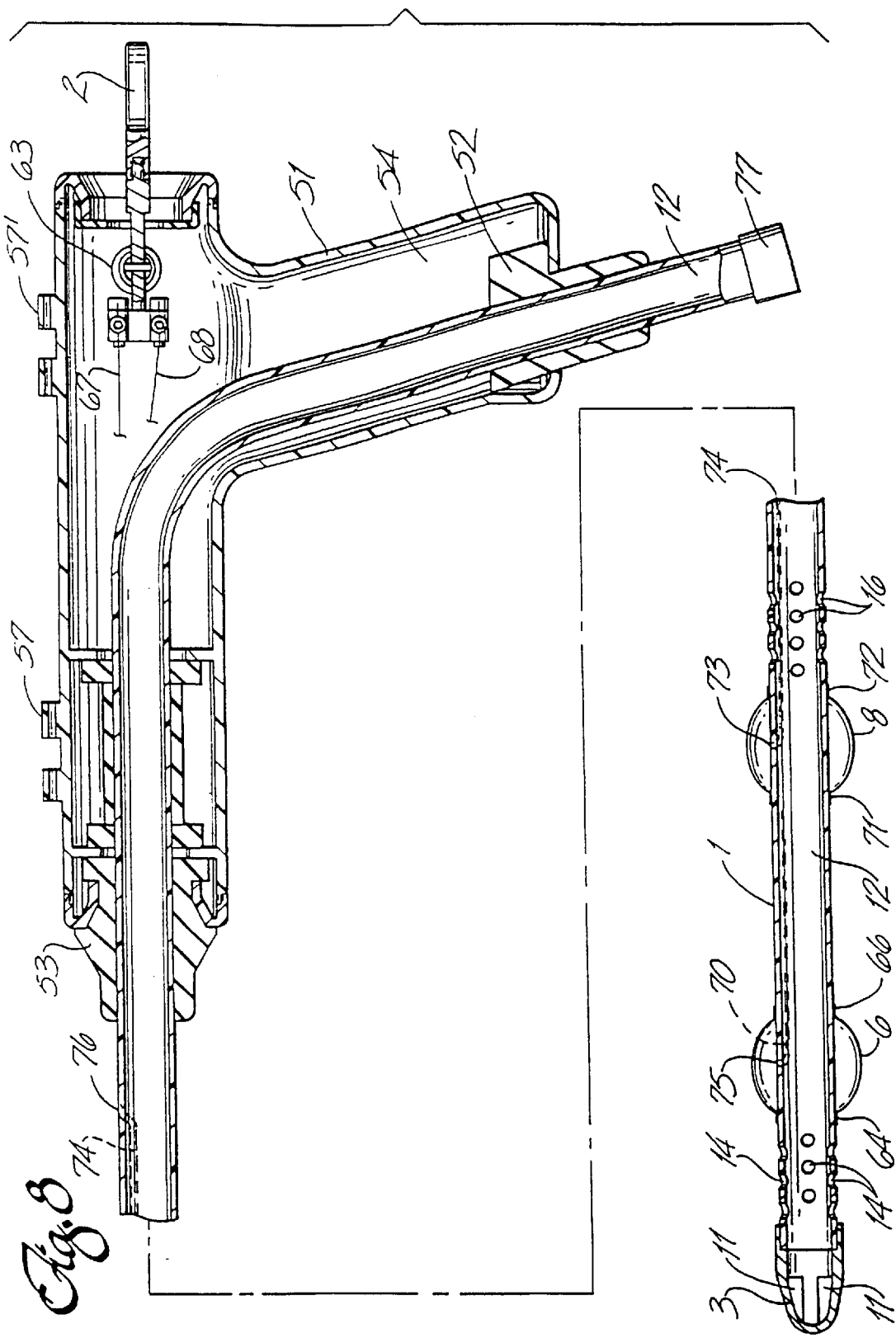

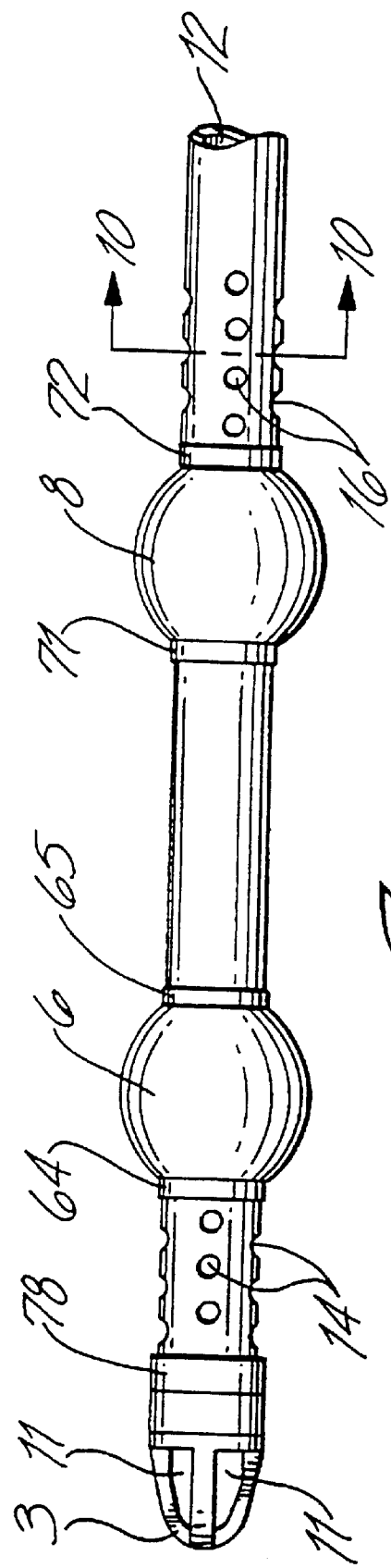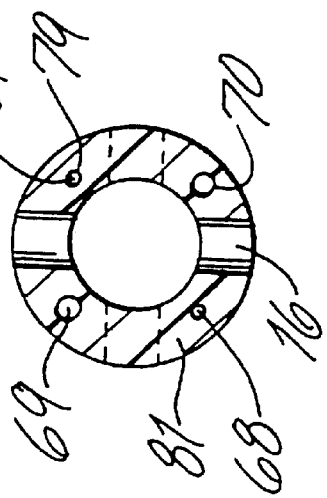

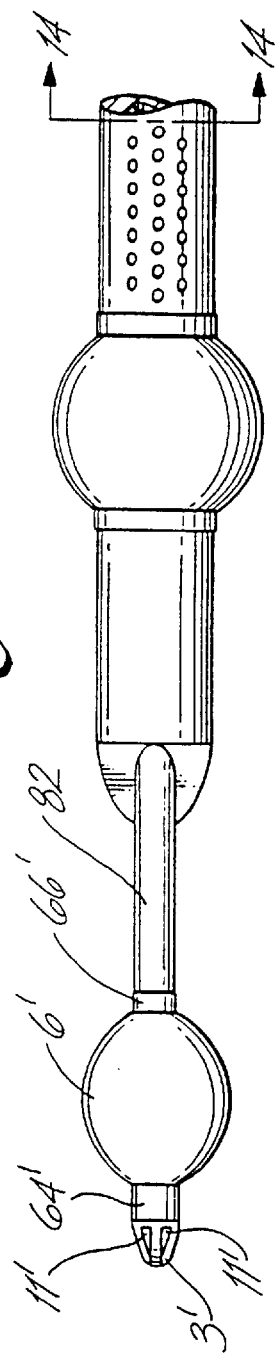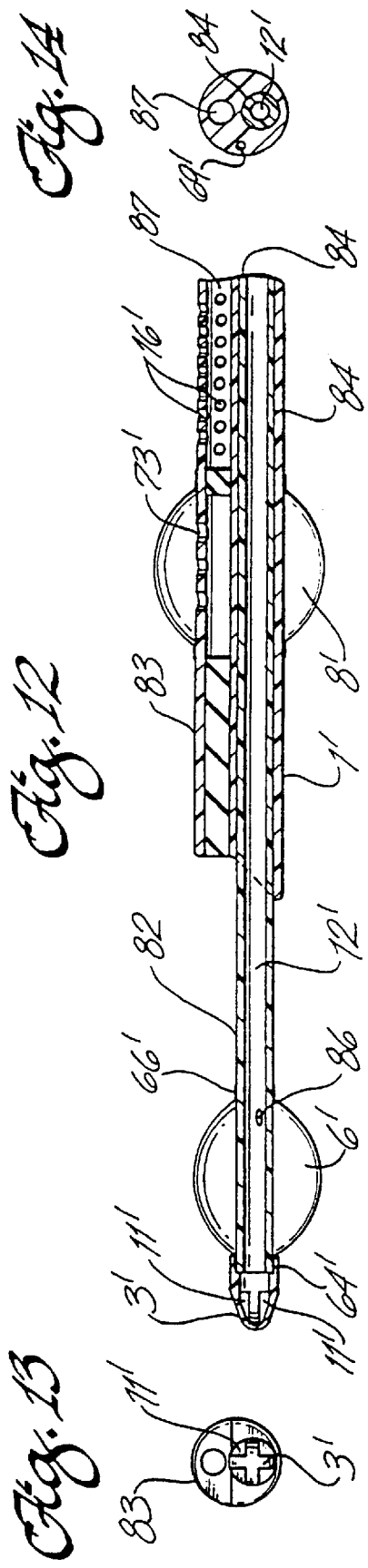

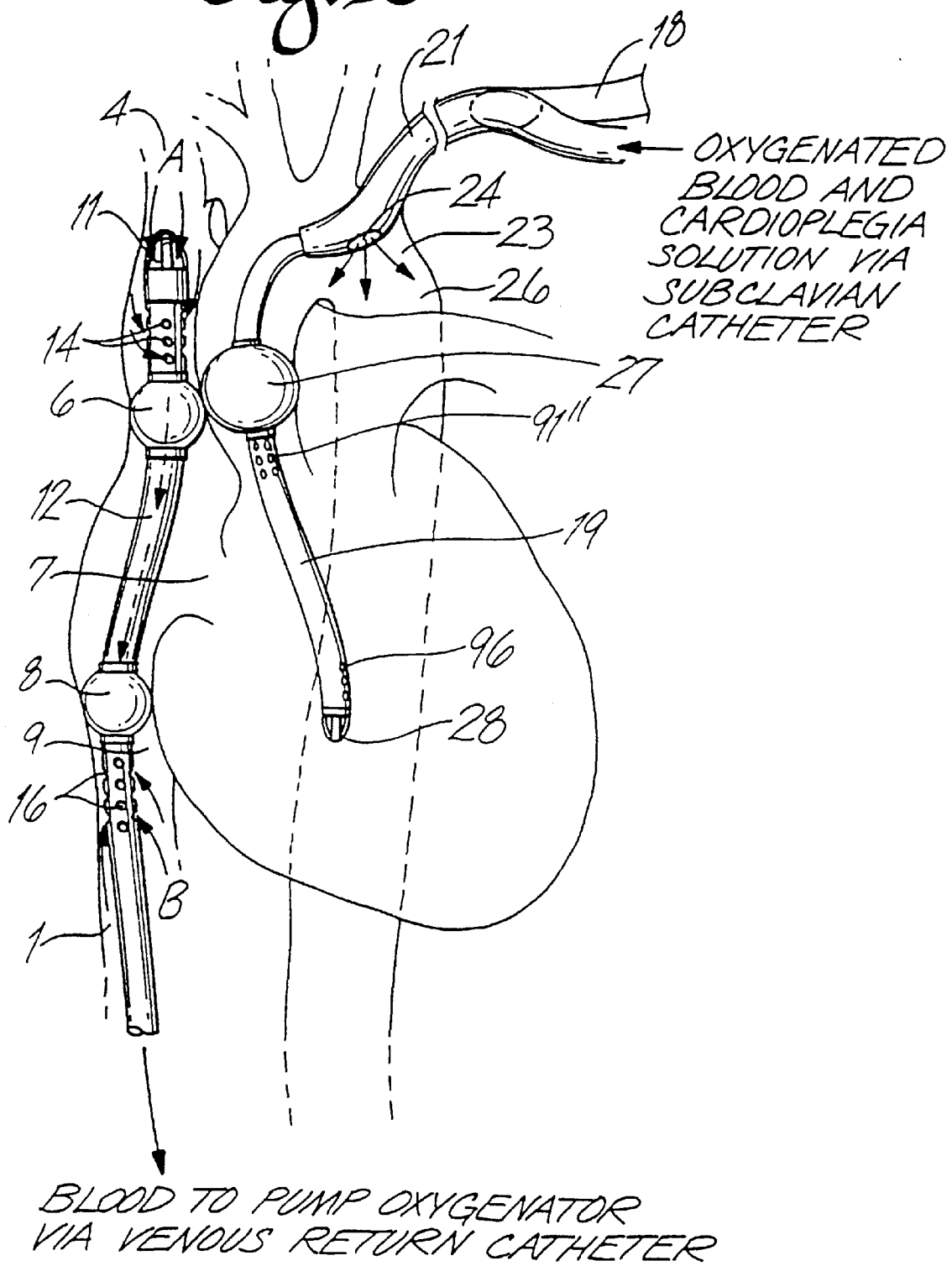

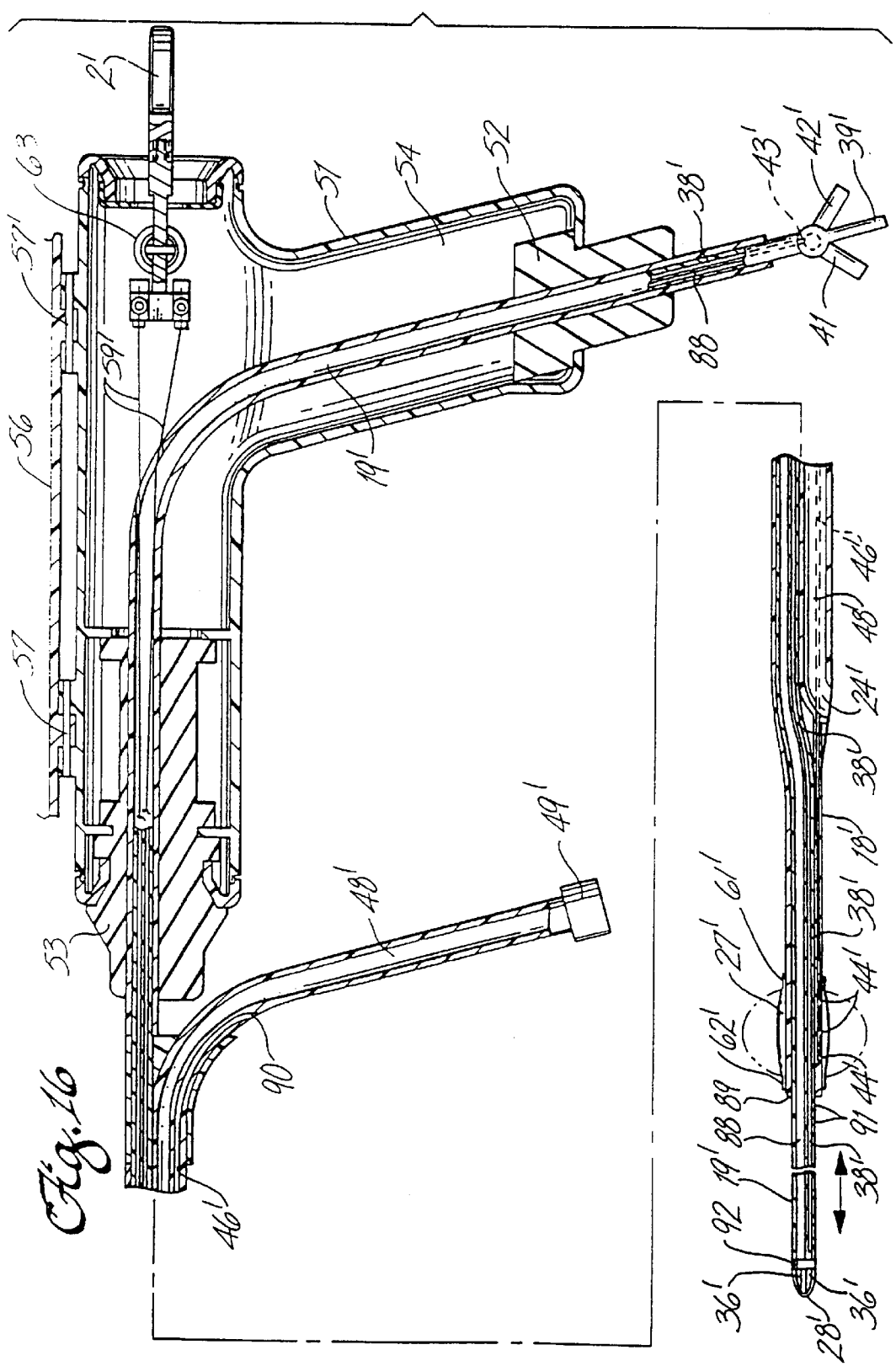

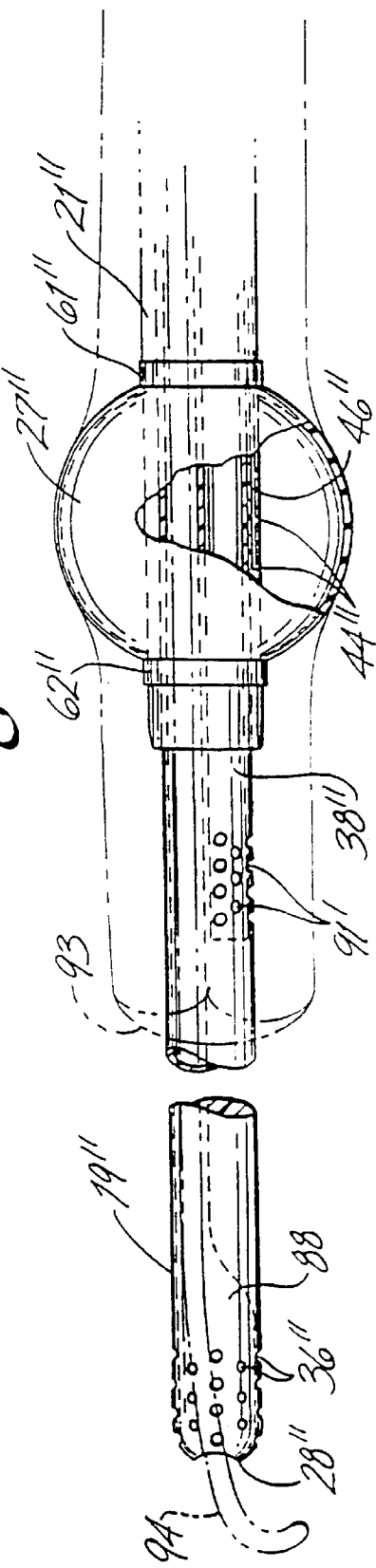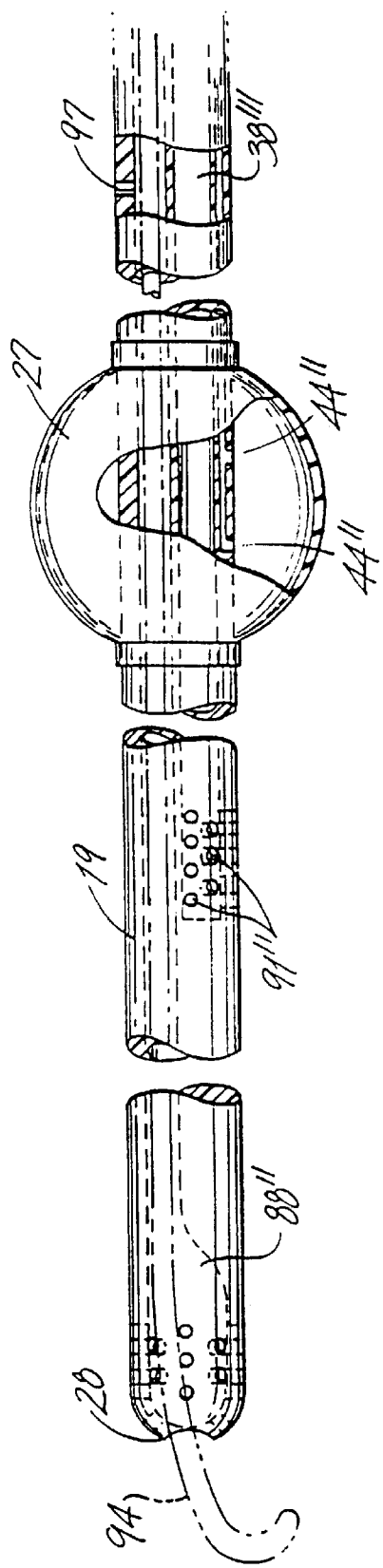

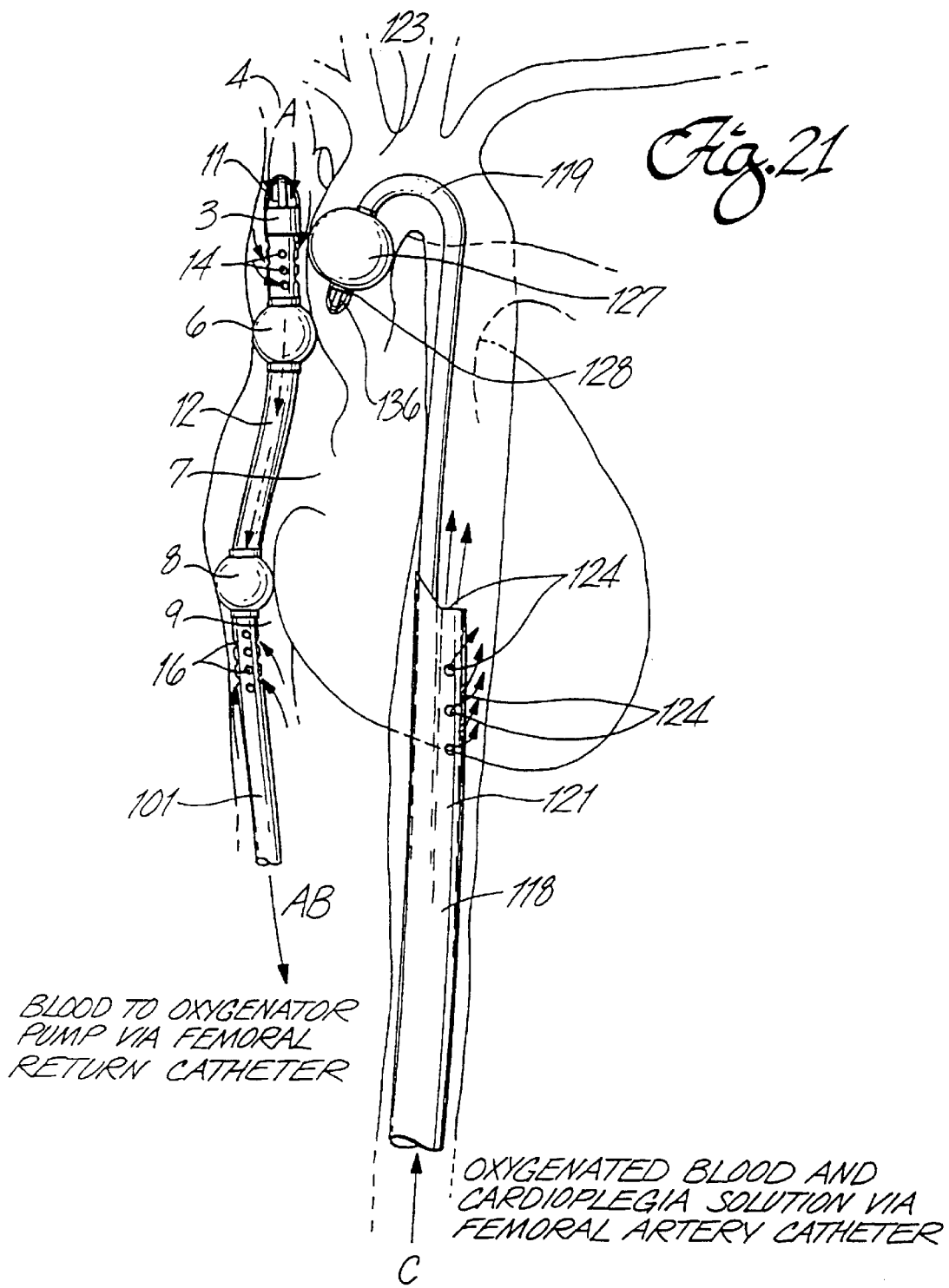

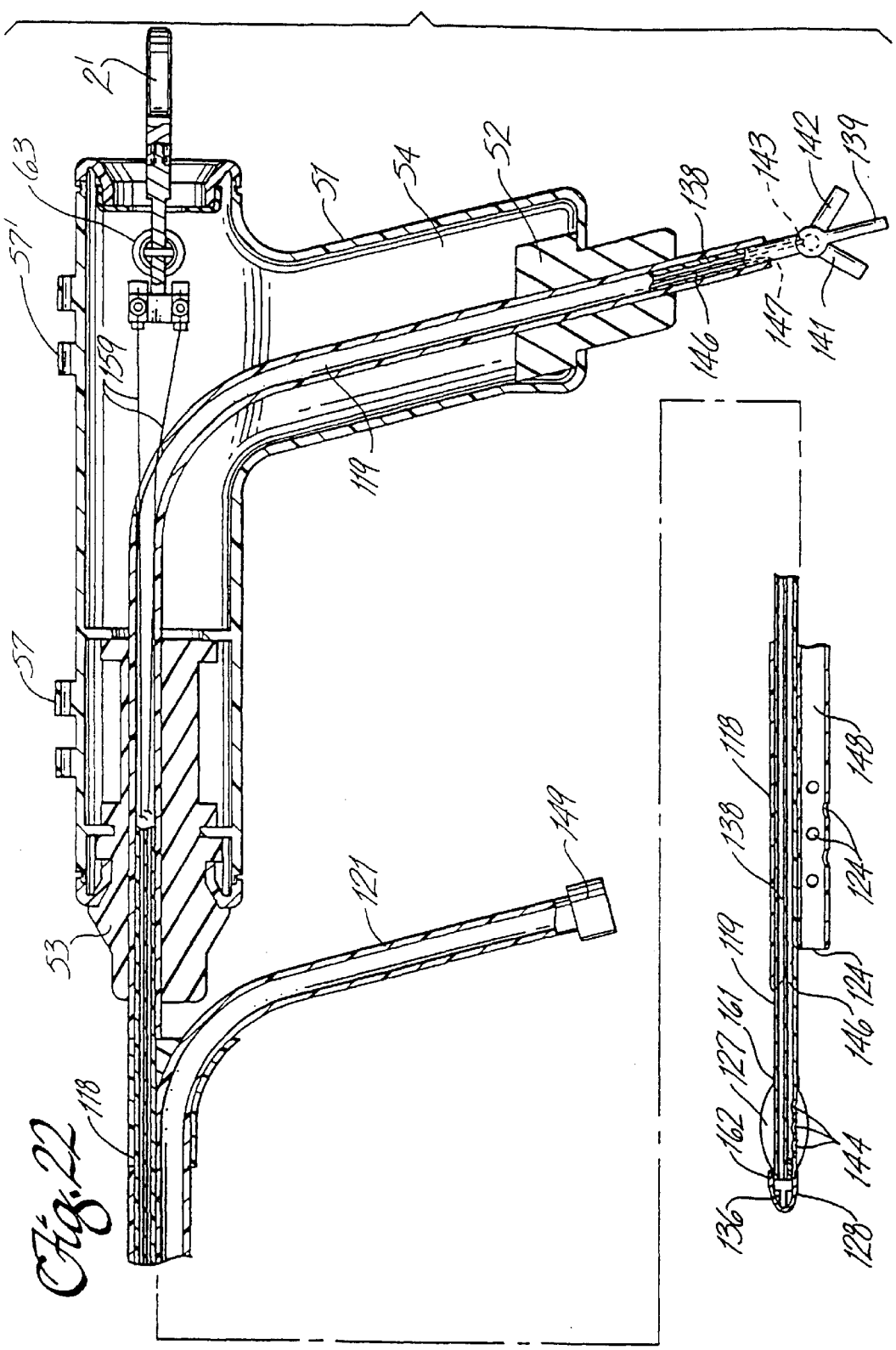

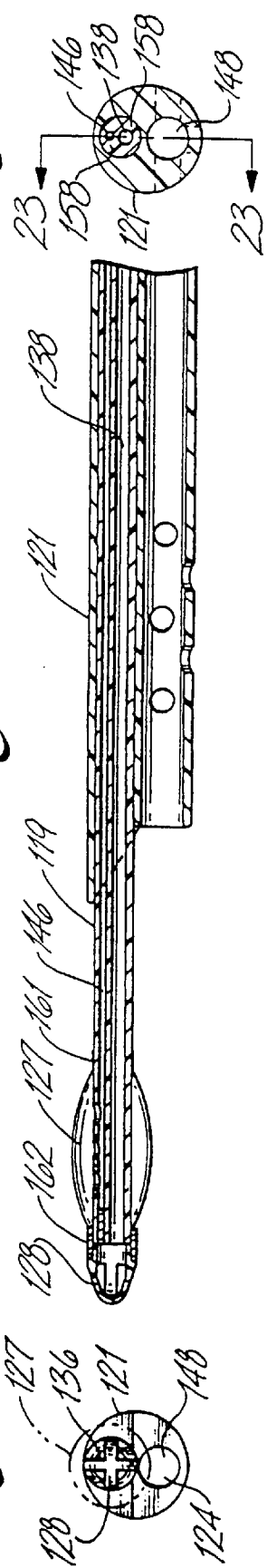

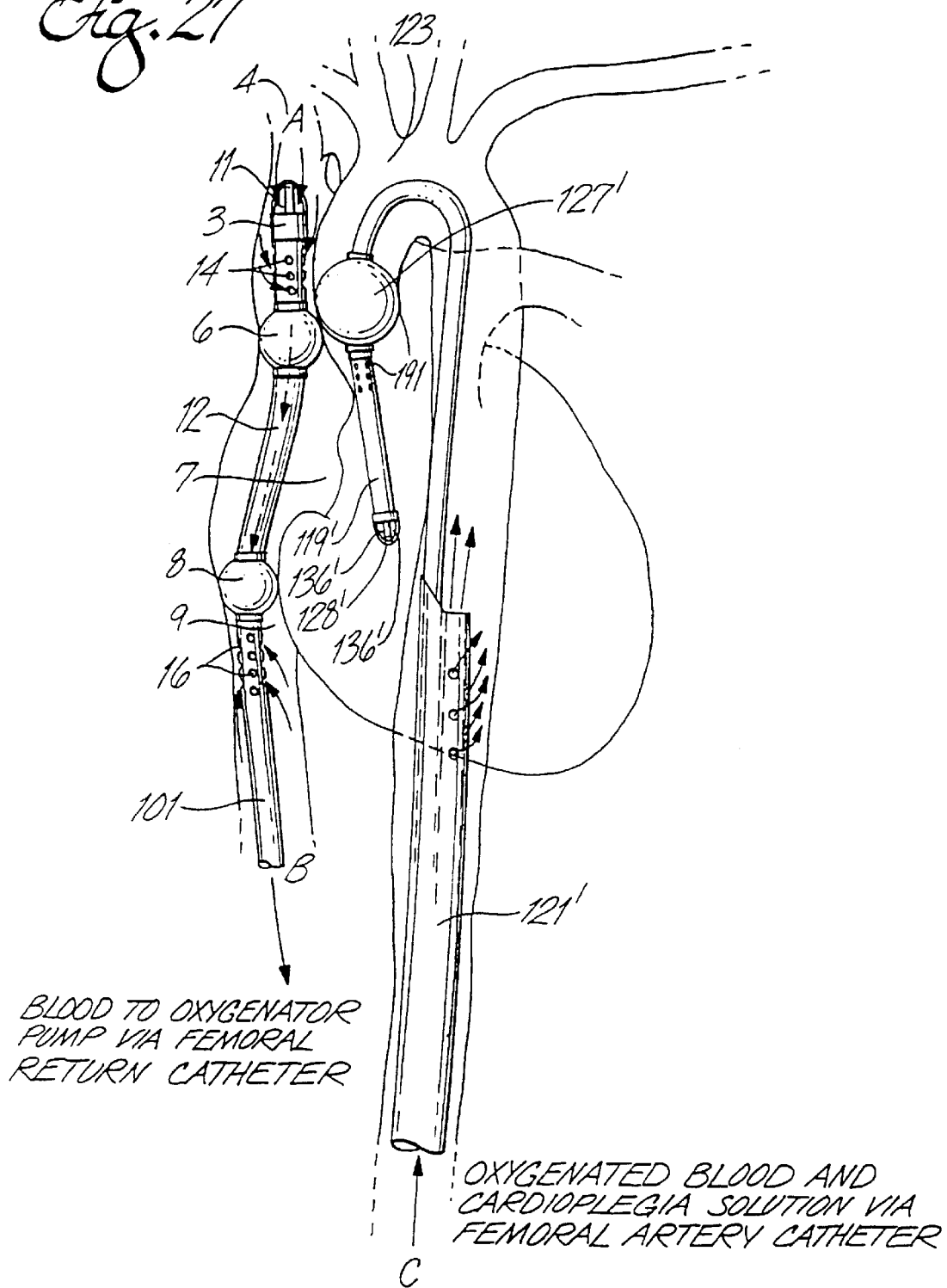

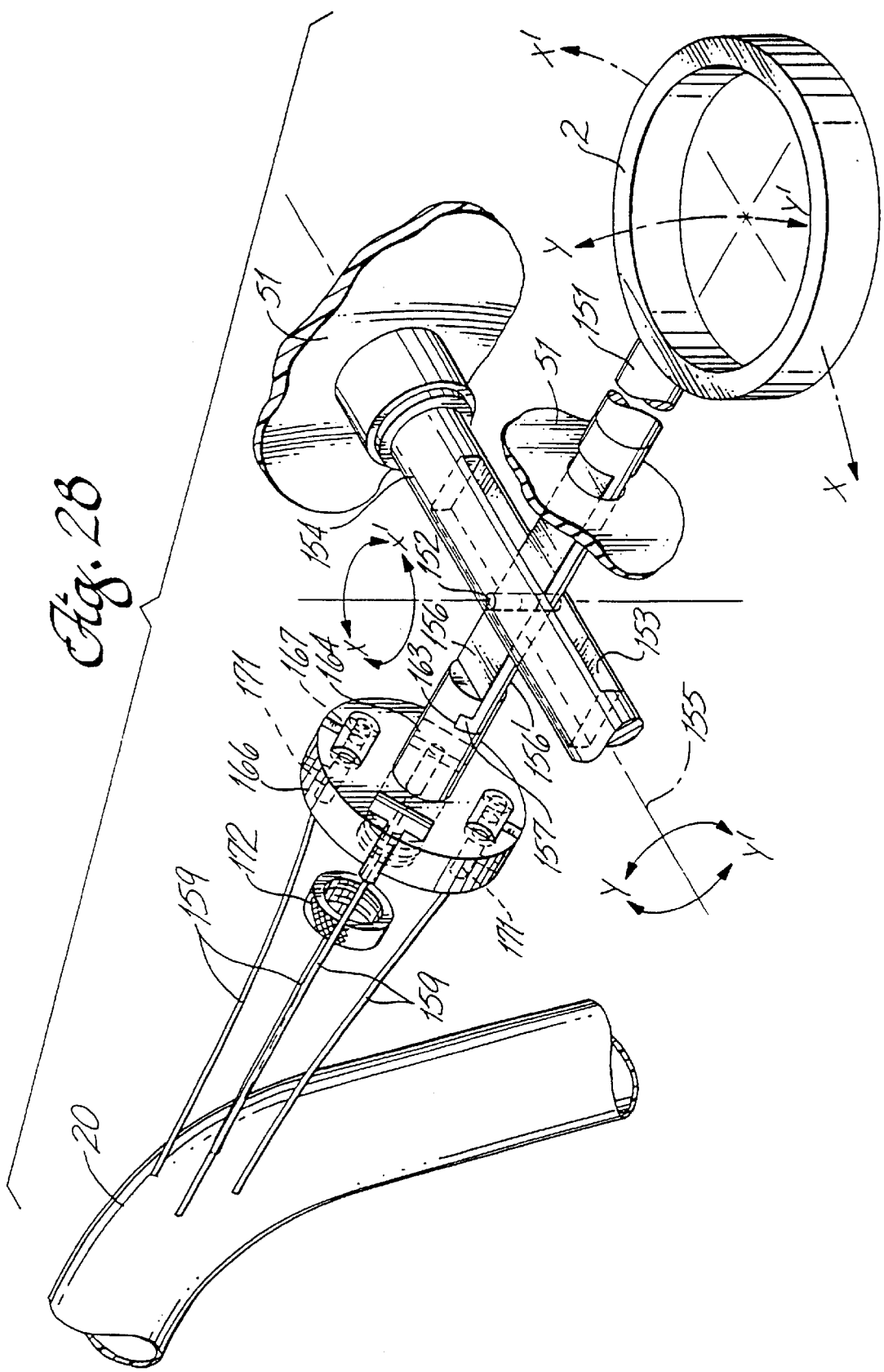

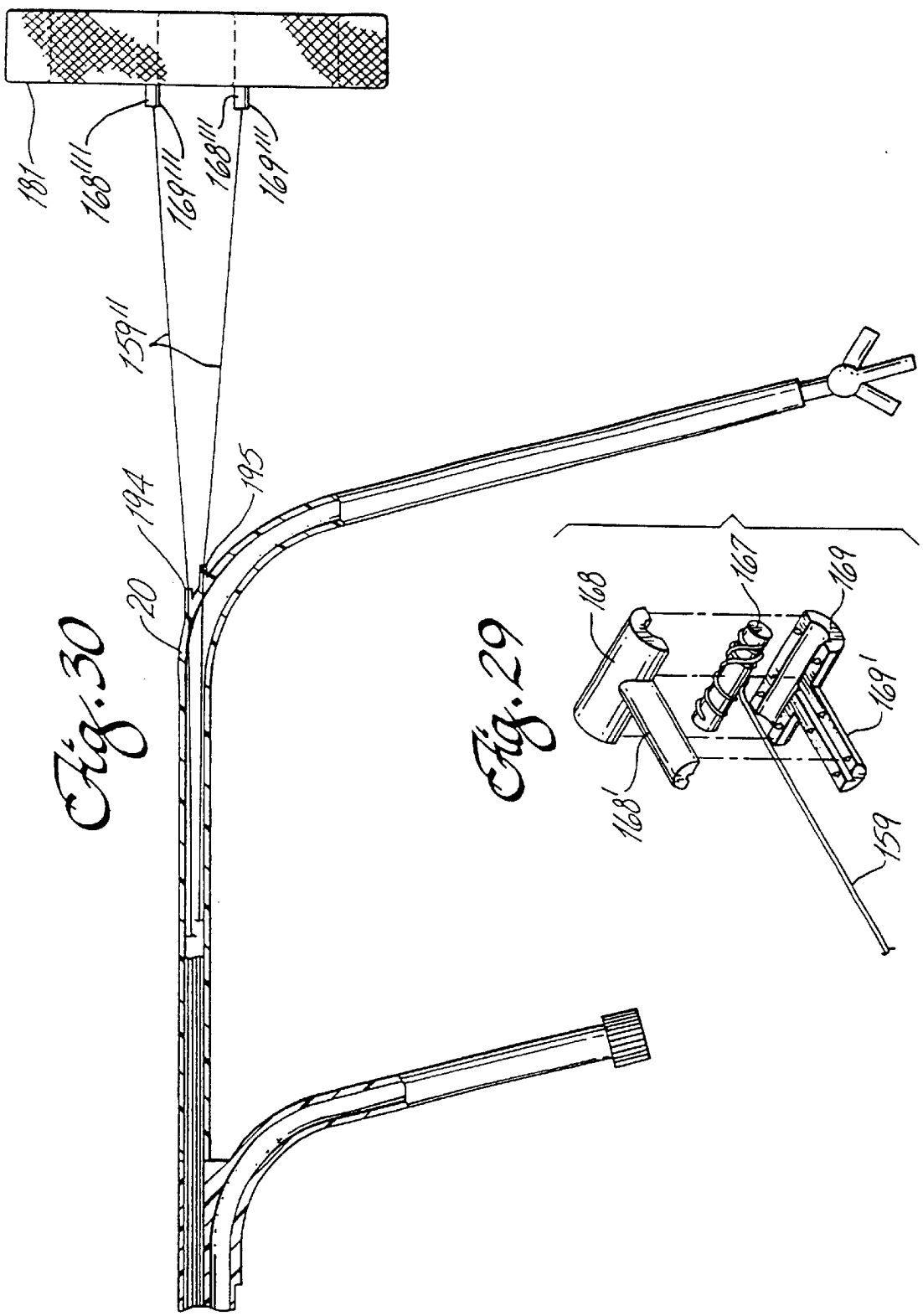

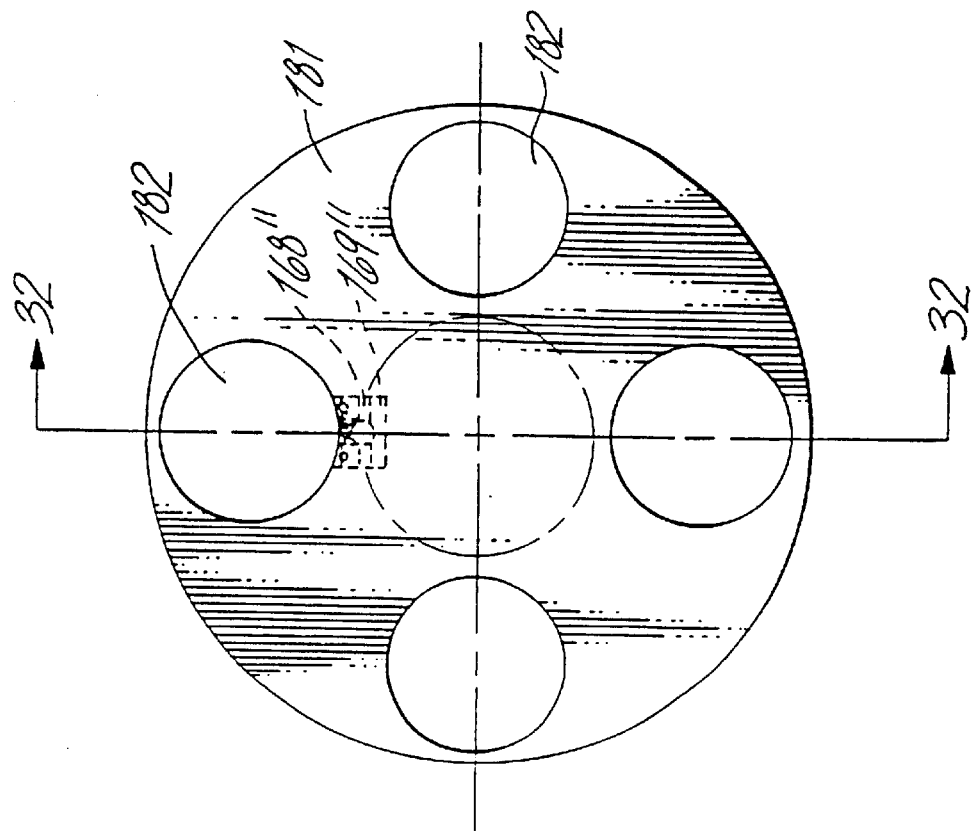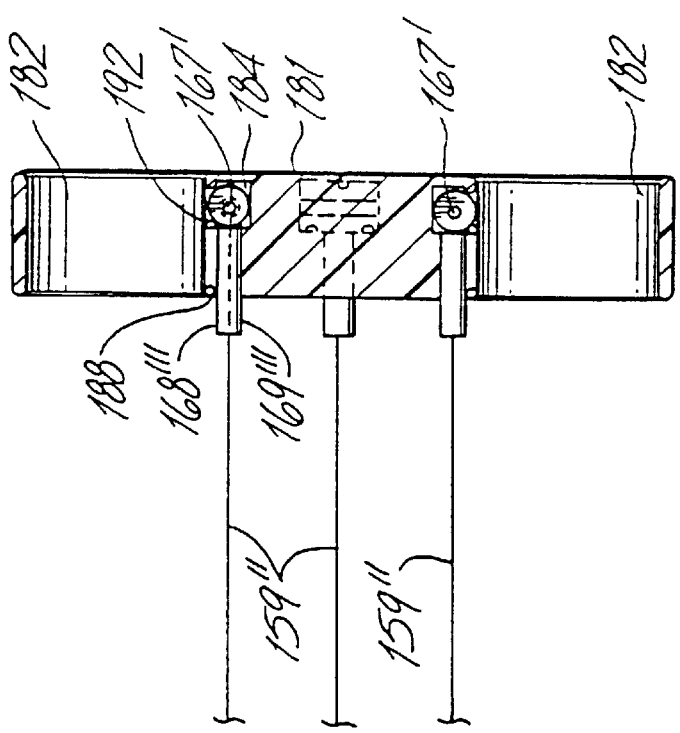

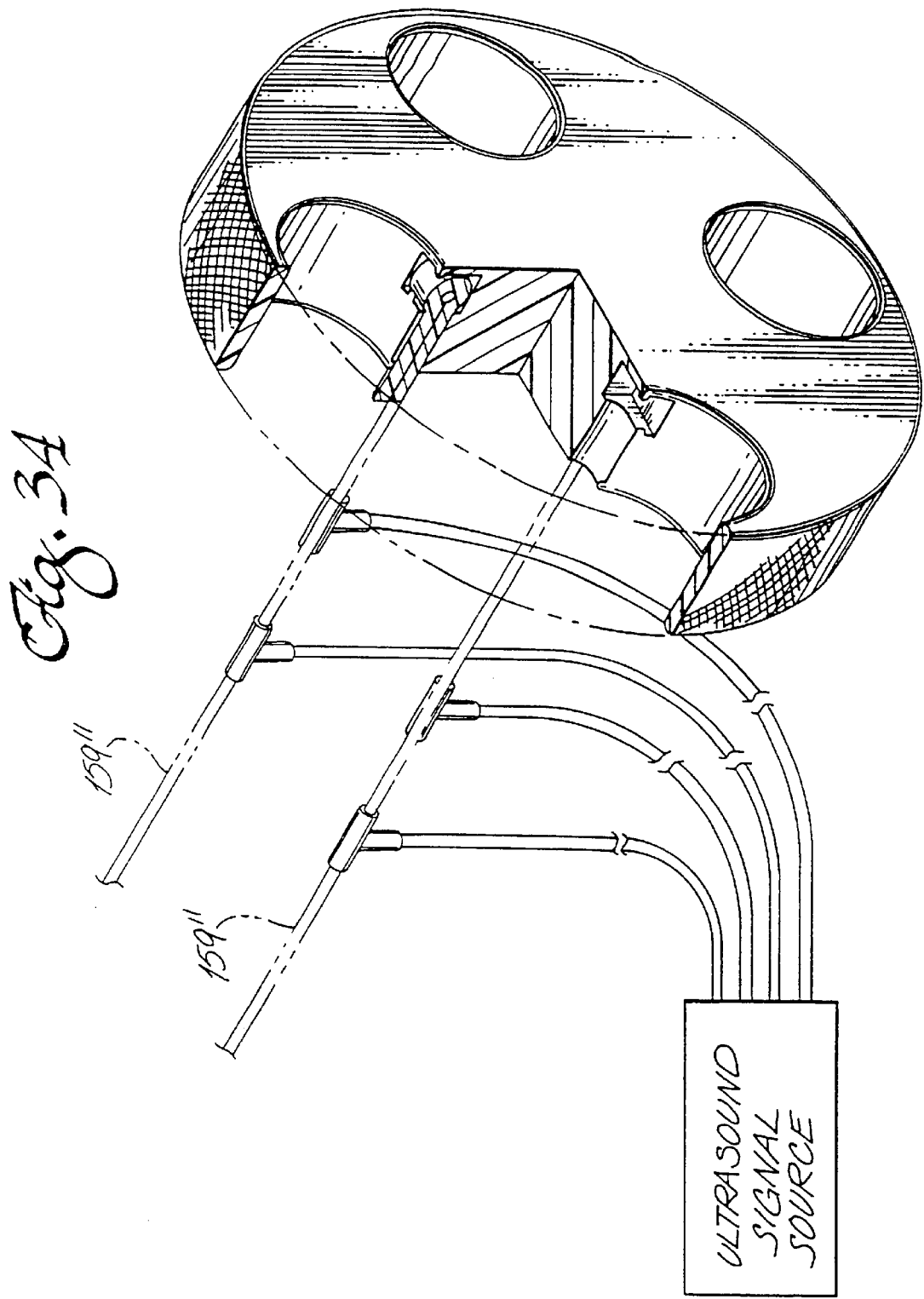

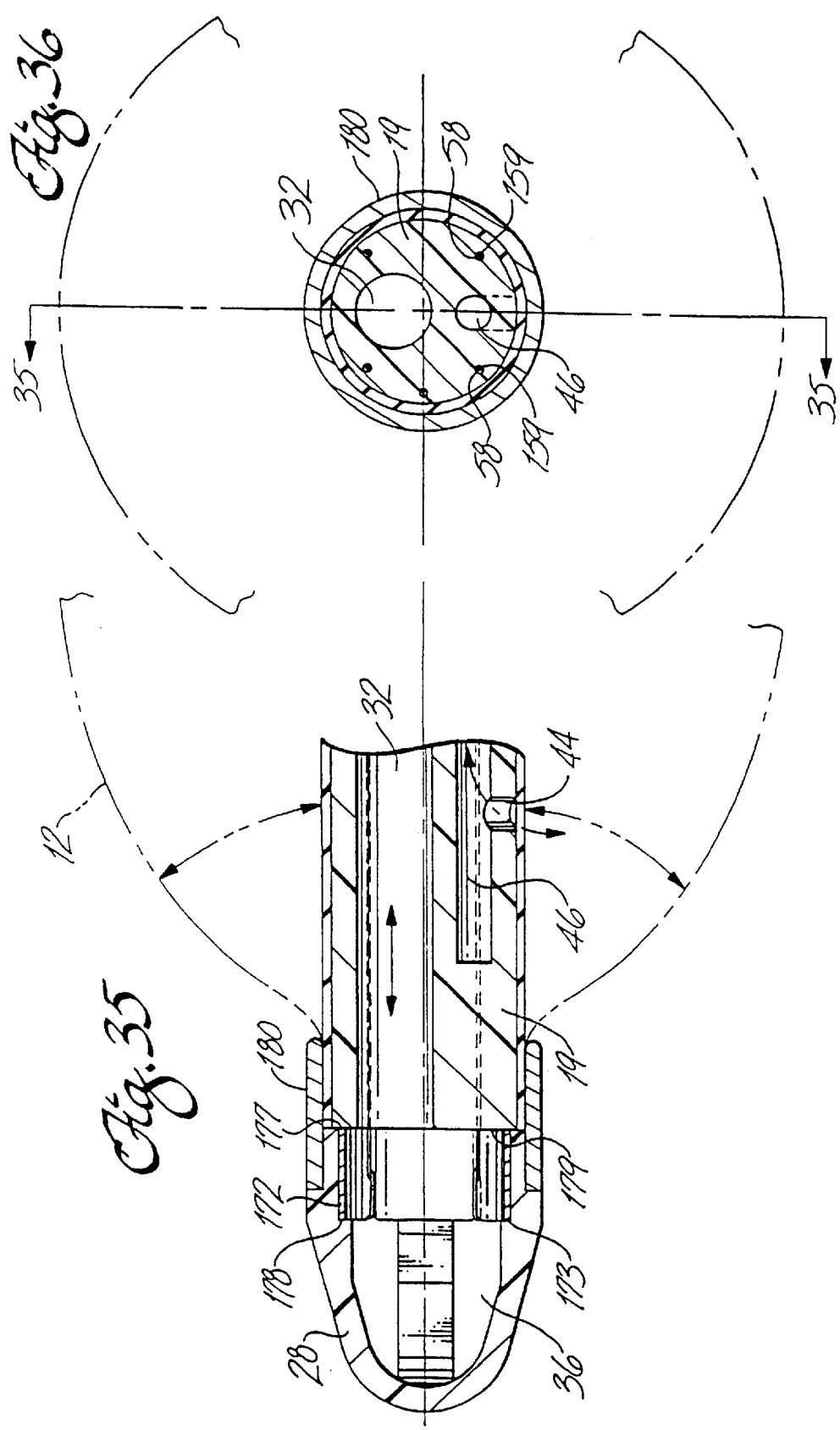

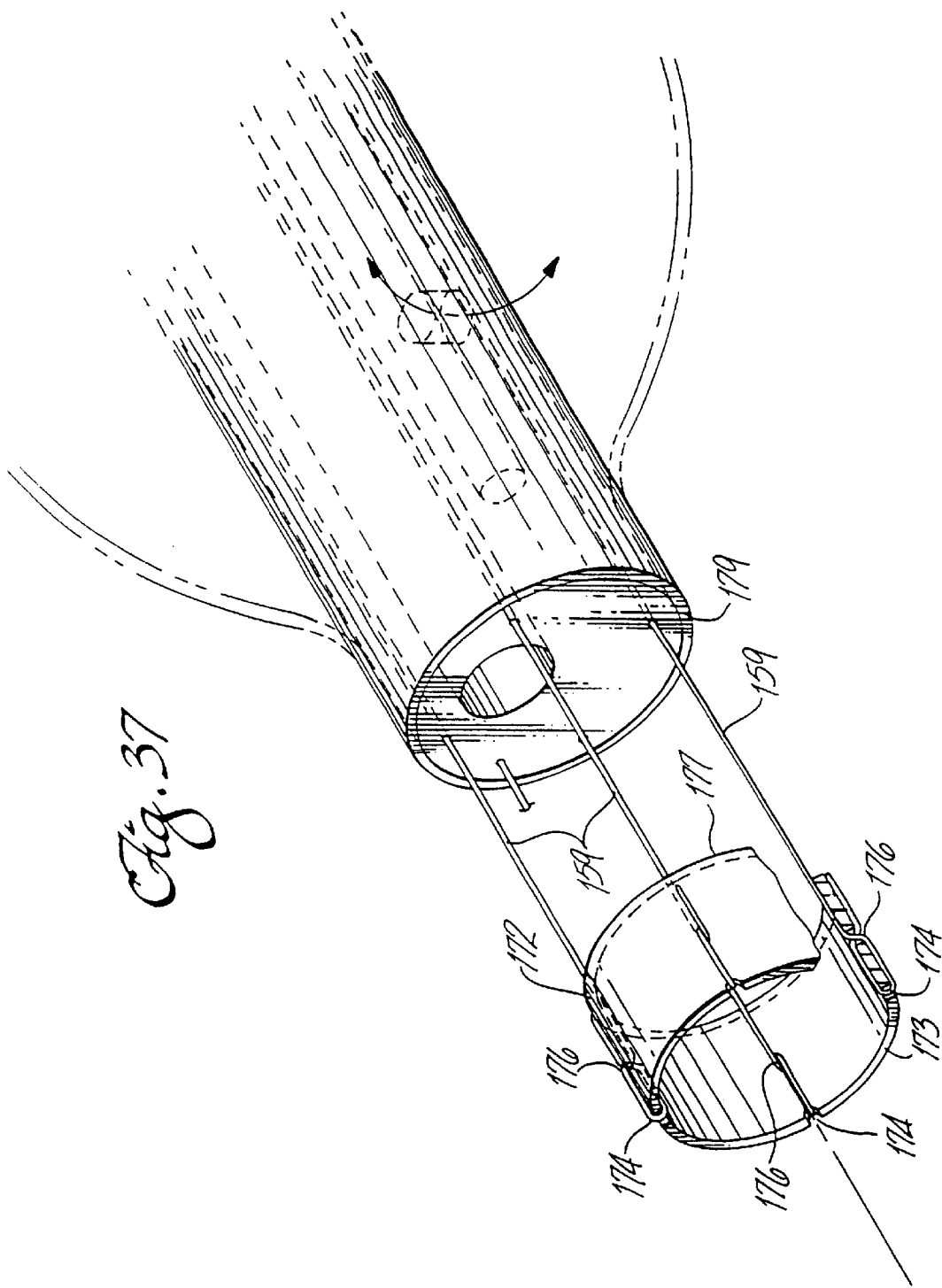

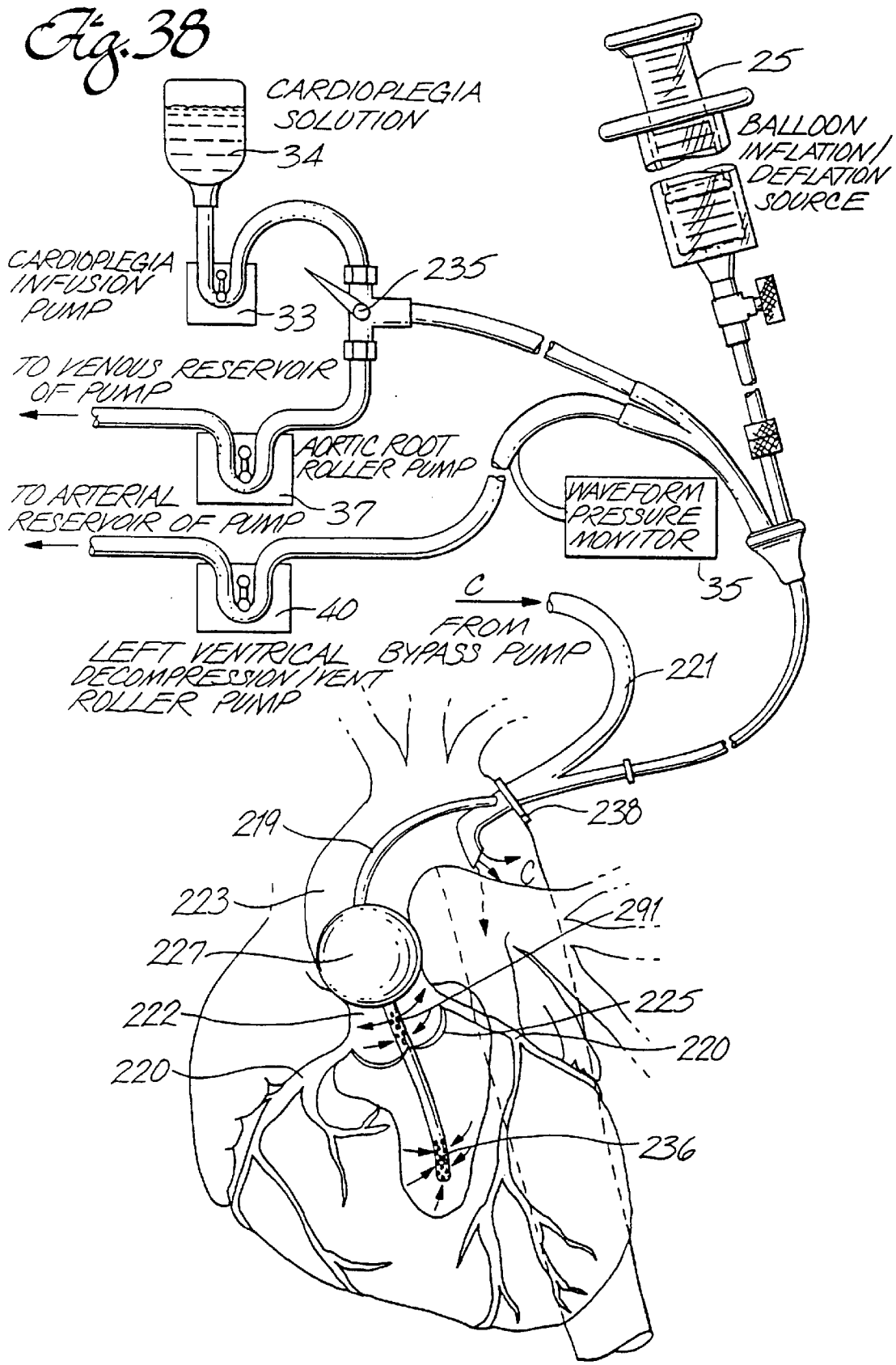

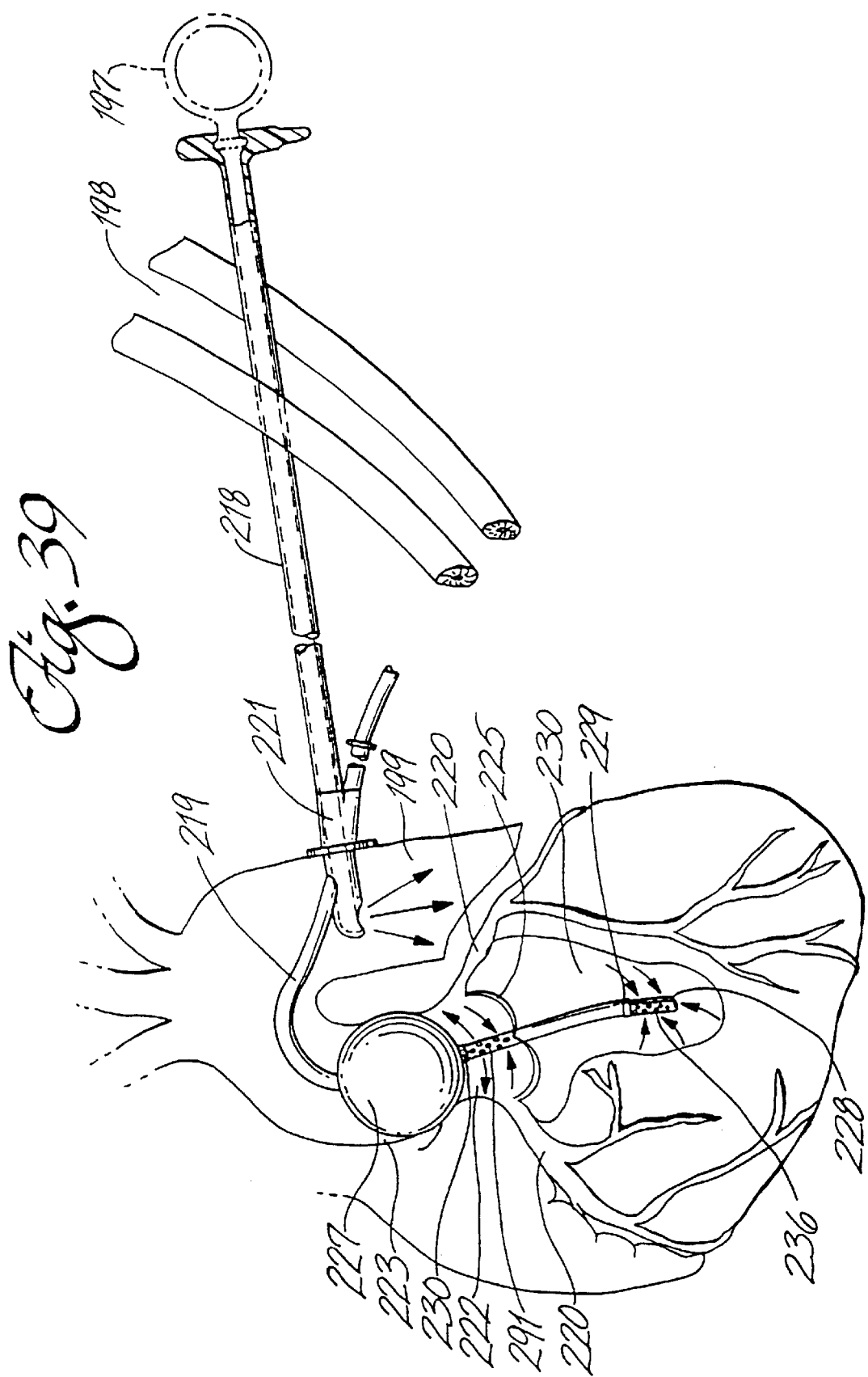

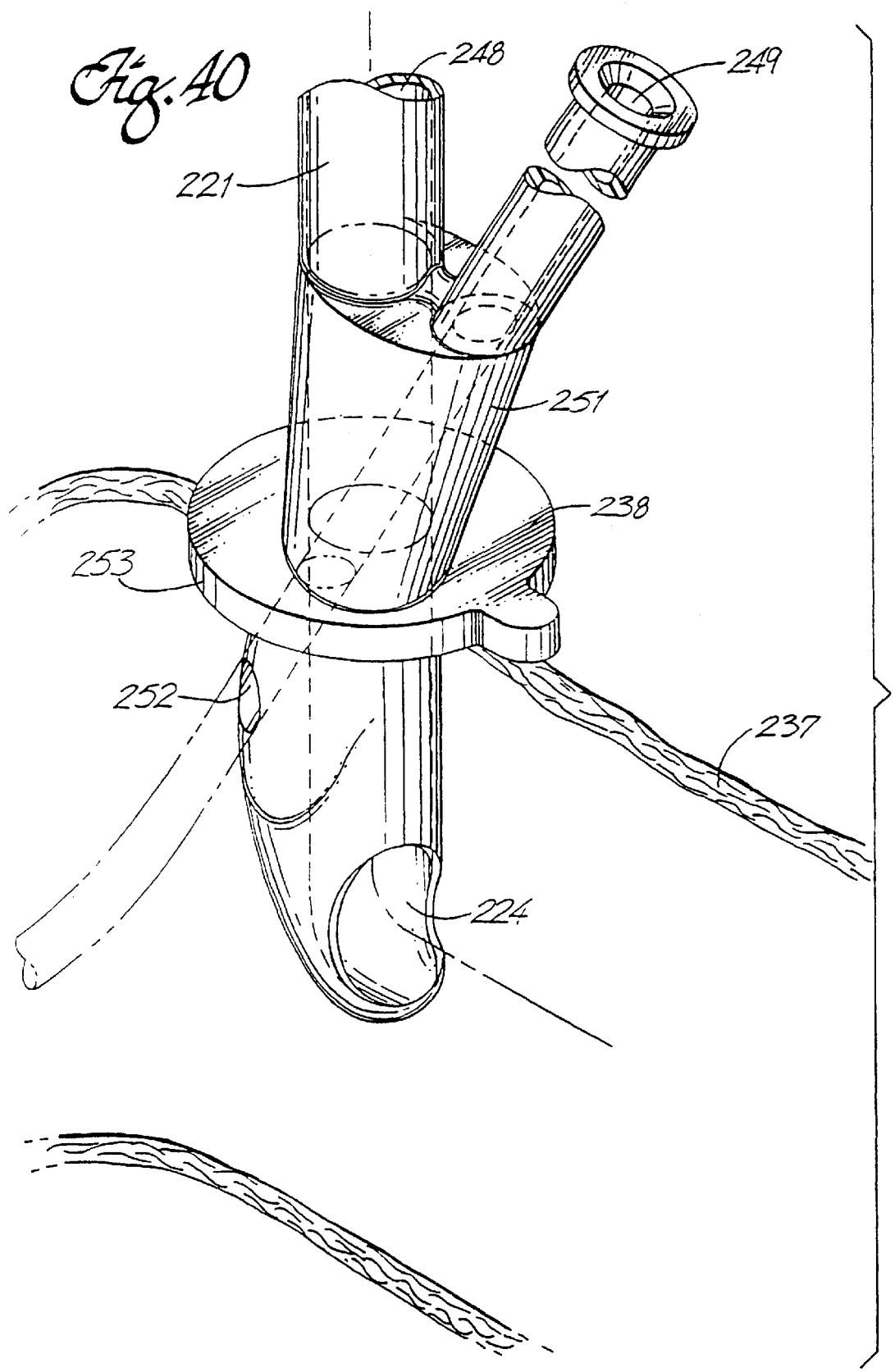

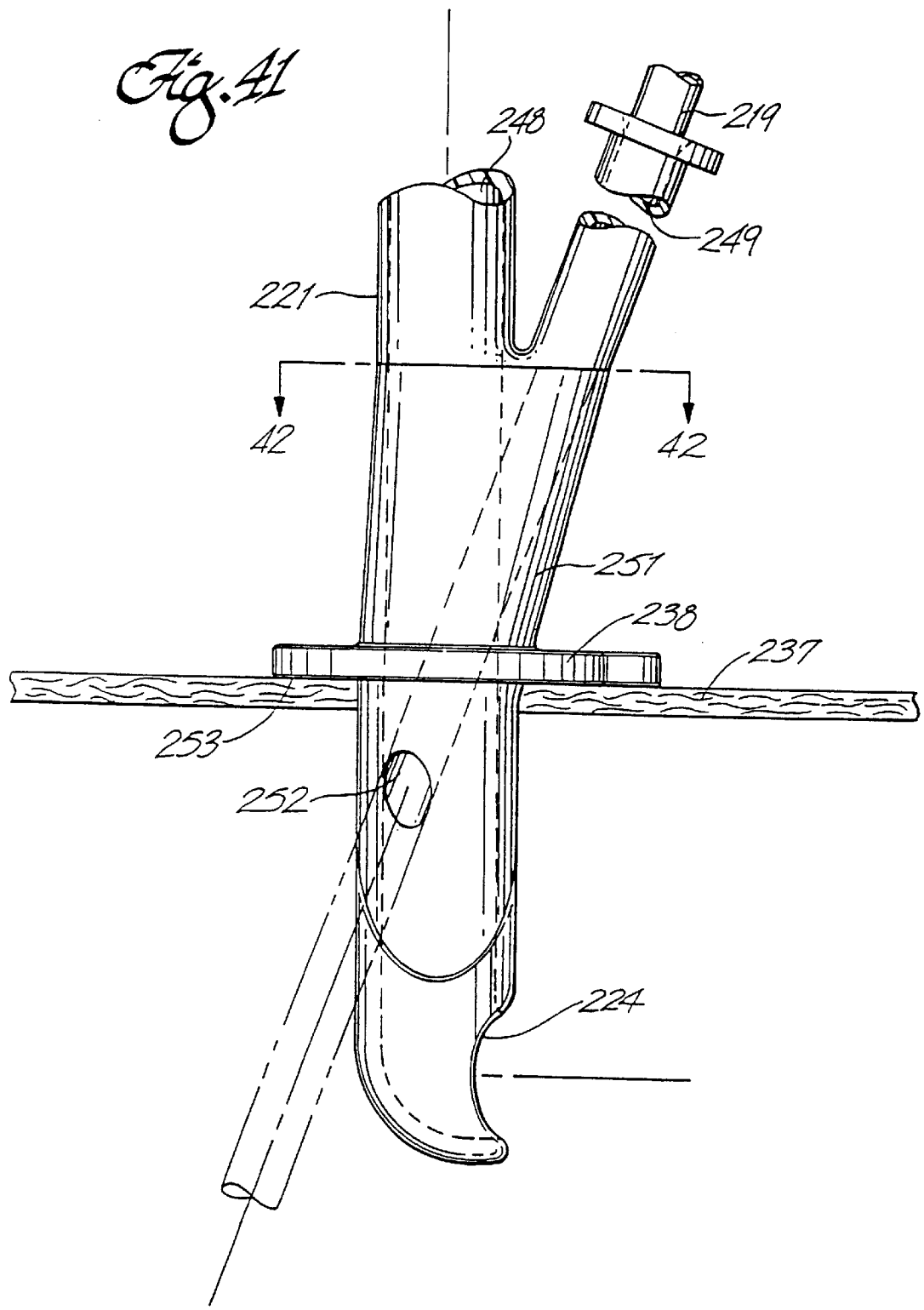

METHOD FOR CANNULATING A PATIENT'S AORTIC ARCH AND OCCLUDING THE PATIENT'S ASCENDING AORTIC ARCH

This application is a continuation of U.S. application Ser. No. 08/580,076, filed Dec. 20, 1995, now U.S. Pat. No. 5,800,375 which is a continuation of U.S. application Ser. No. 08/250,721 filed May 27, 1994, now U.S. Pat. No. 5,478,309.

FIELD OF THE INVENTION

This invention relates to a system of venous perfusion and a rterial perfusion catheters for use in obtaining total cardiopulmonary bypass support and isolation of the heart during the performance of heart surgery with provisions for proximal aortic occlusion, aortic root cardioplegia delivery, aortic root venting, and left ventricular decompression without the necessity for a conventional open chest operation.

BACKGROUND OF THE INVENTION

Each year cardiopulmonary bypass permits over 500,000 patients worldwide with disabling heart disease to undergo therapeutic cardiac operations. The essential goals of cardiopulmonary bypass for heart surgery are to provide life-support functions, a motionless, decompressed heart, and a dry, bloodless field of view for the surgeon.

In a basic heart-lung life-support system oxygen-poor blood is diverted from the venous circulation of the patient and is transported to the heart-lung machine where reoxygenation occurs, carbon dioxide is discarded and heat regulation (warming or cooling) is accomplished. This processed blood is then returned (perfused) into the patient's arterial circulation for distribution throughout the entire body to nourish and maintain viability of the vital organs. Although current venous diversion and arterial perfusion methods can be combined with other measures to effectively isolate the heart for cardiac surgery, they are associated with disadvantages and limitations which contribute significantly to patient morbidity, mortality, and health care costs. It is thus desirable to develop improved cardiopulmonary bypass devices and methods that are safer, less traumatic, and more cost effective.

In the prior art, the method of collecting oxygen-depleted venous return blood from a patient for transportation to the cardiopulmonary bypass pump (heart-lung machine) for re-oxygenation and temperature regulation consisted of three different techniques: (1) a single venous catheter was inserted directly into the right atrium; (2) two catheters were directed via right atrial insertion selectively into the superior vena cava and inferior vena cava; (3) the third technique required the venous catheters to be inserted through peripheral vein access sites with the distal tip of the catheter(s) thereafter positioned either in the right atrium and/or superior vena cava/inferior vena cava areas.

In the techniques where catheters were inserted via the right atrium, the surgeon had available three options of catheter types. Firstly, a simple type where all of the orifices or openings for passage of blood into the catheter were positioned within the atrial chamber; or secondly, a two-stage type wherein some openings were positioned in the atrial chamber and others were located at the tip of the catheter device and positioned in the inferior vena cava; or thirdly, where two individual catheters were inserted at separate sites into the right atrial chamber or caval (inferior vena cava/superior vena cava) structures and selectively directed so that all orifices or openings for passage of blood were positioned within the superior vena cava or the inferior vena cava respectively. Direct insertion of catheters into the right atrium or vena cava results in direct surgical trauma due to the holes which must be cut in these structures for catheter entry; A circular, purse-string suture, an atrial vascular clamp for controlling bleeding and closing the hole, adds to the operative time and the cost of the procedure. Surgical wounds in the atrium, inferior vena cava, or superior vena cava have the potential for causing complications including, but not limited to, hemorrhagic bleeding, cardiac rhythm disturbances, air embolism (introduction of air into the cardiac chambers), and extensive surgical adhesions. Furthermore, this approach requires a major invasive breastbone splitting (sternotomy) or rib spreading (thoracotomy) surgical procedure to reach the atrium and make the insertion.

Cardiopulmonary bypass support can be either partial where only a portion of the blood returning via the superior vena cava (upper body) and inferior vena cava (lower body) into the right atrium is diverted into the pump (heart-lung machine); or, total, wherein all, blood returning via the superior vena cava and inferior vena cava is diverted away from the right atrium into the pump. There are clinical situations where it is advantageous to divert all venous return blood away from the heart. Total cardiopulmonary bypass contributes to cardiac decompression and decreases the detrimental effects of myocardial distention. Furthermore, it provides the surgeon with superior operating visibility of structures within the cardiac chambers which can be obscured if a substantial volume of blood is allowed to enter the heart. There are two methods in the prior art for achieving total cardiopulmonary bypass. The first required placement of tourniquet loops around the superior vena cava and inferior vena cava catheters. The loops are snugly tightened around the catheters in order to prevent blood from entering the atrium. In the second method, occlusion balloons mounted on selective superior vena cava and inferior vena cava catheters were inflated to prevent blood from reaching the right atrium. Both of these methods for total cardiopulmonary bypass capability require major surgical thoracotomy or sternotomy for access to the right atrium and caval structures. Direct surgical dissection of the inferior vena cava, superior vena cava, and right atrium for catheter insertion and tourniquet loop positioning not only adds to the operative time but also increases the risks of injury to these structures which could lead to bleeding, cardiac rhythm disturbances and scarring.

Although peripherally inserted venous drainage catheters of the prior art avoid direct cardiac trauma and can be placed without a major invasive chest incision (sternotomy or thoracotomy), they are not capable of establishing the condition of total cardiopulmonary bypass.

The technique of the present invention is to insert the venous catheters through a peripheral vein access site and thereafter position the drainage orifices in the superior vena cava and inferior vena cava areas. The catheter(s) features inflatable occlusion balloons that allow the choice of either partial (balloons deflated) or total (balloons inflated) cardiopulmonary bypass support. The insertion site(s) may be individual or a combination of choices of the femoral veins, iliac veins, subclavian veins, axillary veins, and internal jugular veins. The use of this technique has the advantage of avoiding a major chest incision as well as surgical trauma to the right atrium, superior vena cava and inferior vena cava. This eliminates costly surgical instruments, sutures, tourniquets, and operative time associated with the conventional approaches.

In the prior art, the method of delivery of oxygen-rich (arterialized) temperature-regulated blood from the cardiopulmonary bypass pump to the arterial circulation of the patient consisted of two different techniques: 1.) a simple, single lumen catheter (cannula) was inserted directly into the aorta (most often the ascending aorta). To make such an insertion, however, access to the aortic wall could only be achieved through a major invasive chest incision such as thoracotomy or sternotomy. Direct surgical trauma to the aorta occurs as a result of the hole which must be cut in the aorta for catheter entry. This hole is surgically repaired after removal of the catheter at the end of the operation but leaves potential for major post-operative bleeding. Other catastrophic complications related to direct insertion of catheters into the aorta include: (a) the risk of splitting the three layers of the aortic wall apart (known as aortic dissection) and (b), the risk of disruption of cholesterol and/or calcium deposits from the innermost layer of the aortic wall at the site of entry which can then be carried into the blood stream to occlude flow in distal arterial branches and reduce function in vital organs such as the brain (stroke), kidneys (renal failure), legs (gangrene), bowels (gangrene), liver (hepatic failure). 2.) The alternative prior art method for delivery of arterialized blood to the patient's circulation employed a simple, single lumen catheter which was inserted into a peripheral artery, either percutaneously or by using a surgical cut-down procedure. This technique avoided a major chest incision. While the two arterial methods of the prior art complete the loop of the heart-lung machine for basic life-support by returning blood to the patient, neither has the intrinsic capability of providing all optimal conditions (requirements) for heart surgery which will be discussed below.

In order to perform complex, delicate surgical procedures on the heart, i.e., coronary artery bypass and valve operations, it is desirable to establish a resting, non-beating (flaccid) non-distended state. This condition, along with a dry, bloodless field, is ideal for safe manipulation and suturing of cardiac structures, and furthermore, contributes to decreased metabolic cardiac energy demands while promoting preservation of cellular functions. In the prior art this non-beating state was accomplished by delivery of a cardioplegia (heart paralyzing) solution to the coronary circulation to stop the heart by one or a combination of two general methods: (1) Antegrade (cardioplegia infusion is initiated at the arterial end of the coronary circulation via the origins of the coronary arteries, i.e., ostia, in the aortic root and flows towards the capillaries within the heart muscle; (2) retrograde (cardioplegia infusion is directed into the venous circulation via a coronary sinus and flows backwards into the capillary circulation of the heart muscle). It is at the capillary level where the cardioplegia solution interacts with the cardiac muscle cells, resulting in its desired effects.

All prior art antegrade cardioplegic techniques for heart surgery required an occlusive vascular clamp to be applied to the ascending aorta to prevent arterialized blood from the cardiopulmonary bypass pump from reaching the coronary arteries, proximal ascending aorta, and aortic valve areas while at the same time maintaining arterial perfusion to all points distal (downstream) to the clamp. This isolation maneuver then allowed infusion of cardioplegia solution either directly into the coronary openings (ostia) via catheters, (cannulas) whose tips were inserted into the ostia or indirectly via a catheter (cannula) inserted into the isolated segment of the ascending aorta adjacent to the coronary ostia. Surgical trauma to the aorta resulted from the aortic puncture wounds or major aortic incisions that had to be made to use these techniques, both of which were dependent on major sternotomy or thoracotomy for exposure. The use of the surgical clamp to squeeze the opposing aortic walls together also has major disadvantages. For instance, a major invasive surgical incision (sternotomy or thoracotomy) is required to reach the aorta in order to apply the clamp. By the compressing or squeezing action of the clamp, fragments of cholesterol or calcium in the aortic wall may break away and embolize to the vital organs downstream. In cases of very severe calcification of the ascending aorta, it is not feasible to apply an external clamp because the compressibility of the aorta has been lost. Surgeons must then resort to less optimal, more complex methods of bypass support, myocardial protection and heart isolation which further increases the likelihood of post-operative complications. There are situations where the surgeon cannot proceed with the operation and it is terminated (abandoned) with the patient losing the opportunity for definitive therapeutic treatment of his disabling heart disease. Retrograde prior art cardioplegia delivery methods also are dependent upon major invasive chest operations as well as direct trauma to the atrium for their use. Again, the patient is being subjected to increased risks of bleeding and direct cardiac trauma. The present invention eliminates the need to distort the aorta with a clamp by integrating an occlusion balloon into the arterial perfusion catheter which when positioned in the ascending aorta and inflated appropriately will provide the same function without the risks. Antegrade cardioplegia delivery in the present invention conveys blood into the isolated segment of the ascending aorta just below the aortic occlusion balloon into the coronary ostia, avoiding the need for aortic puncture wounds, aortic incisions, purse-strings or surgical repair.

Prior art methods of controlling distention (decompression or venting) and improving visibility of the heart during heart surgery included: (1) insertion of a catheter via the left atrium or a pulmonary vein which was then directed across the mitral valve so that its openings at the tip were positioned within the left ventricular chamber for suction evacuation (also called venting) of blood; (2) inserting a catheter directly into the apex of the left ventricular muscle so that its openings at the tip were positioned within the left ventricular chamber for suction evacuation (venting) of blood; and (3) the prior art catheter placed in the isolated segment of the ascending aorta for antegrade cardioplegia delivery could alternatively be switched to a suction source to accomplish aortic root venting (decompression) but not left ventricular decompression (venting). All of these methods have the disadvantages of requiring major sternotomy or thoracotomy and are associated with direct cardiac and aortic trauma. The present invention provides for both aortic root and left ventricular decompression integrated into the arterial perfusion catheter which can be inserted remotely without a major chest incision, cardiac trauma or aortic trauma.

When surgeons are required to perform repeat open heart surgery (known as "redo" operations) in someone whose chest has previously been entered via a major sternotomy or thoracotomy, extensive adhesions are usually encountered which obliterate the natural relationship and appearance of anatomic structures. This distortion further increases the risks of injury and massive fatal hemorrhage during the process of exposing, isolating and preparing structures for catheter insertions (arterial, venous, cardioplegia, left ventricular vent) and therapeutic repair. The present invention allows peripheral insertion, institution, and maintenance of cardiopulmonary bypass to take over the circulation prior to opening the chest or at any time thereafter when major hemorrhage, cardiac instability, or other complications arise which lead to deterioration of the patient's condition.

Major invasive chest incisions are often associated with a higher incidence of morbidity including, but not limited to, intraoperative and post-operative bleeding, resulting in the likelihood of increased blood transfusion requirements, returns to surgery for re-exploration to control hemorrhage, longer healing and recovery times, pulmonary complications (such as lung collapse and pneumonia), catastrophic wound infection (mediastinitis), extensive scarring and adhesions, mechanical wound instability and disruption (dehiscence), chronic incisional pain, peripheral nerve and musculoskeletal dysfunction syndromes. Developing a system with features that avoid surgical maneuvers, instrumentation and devices known to be associated with increased morbidity and mortality is desirable. Such improvements have the likelihood of resulting in a favorable impact on patient care, quality of life, and health care costs. The present invention for cardiopulmonary bypass during heart surgery integrates multiple functions which were not available in the prior art and has the advantage of avoiding a major chest operation and its potential complications.

SUMMARY OF THE INVENTION

There is, therefore, provided according to the present invention, a catheter system and method for achieving total cardiopulmonary bypass during heart surgery. The catheter system permits a venous catheter to be inserted peripherally thus avoiding the need for a major chest incision such as a thoracotomy or median sternotomy. By utilizing ultrasound or fluoroscopic imaging, the venous catheter may be precisely positioned adjacent the right atrium such that upon inflation of inflatable balloons carried by the catheter, the superior vena cava and inferior vena cava may be occluded to prevent blood flow into the right atrium thereby achieving the condition of total cardiopulmonary bypass.

The arterial perfusion catheter of the catheter system of this invention in one embodiment may be remotely inserted through a femoral artery or in another embodiment through the left subclavian artery. The arterial catheter device incorporates an inflatable balloon which is carried by a cannula member and steered into the ascending aorta just above the aortic valve and coronary artery orifices (ostias). The balloon is inflated with a saline or other biocompatible fluid until it circumferentially bears against the aortic wall and occludes blood flow through the aorta. This eliminates distortion and trauma to the aorta which would occur if a vascular clamp were to be applied to it externally. The arterial perfusion catheter of the catheter sytems of this invention may be inserted at a remote location into an arterial vessel and thus eliminate the need for a sternotomy or major thoracotomy. Even if the aorta is brittle and heavily calcified or involved with cholesterol deposits, the arterial perfusion catheter of this invention may nevertheless be used.

The present invention is directed to a catheter system and method for achieving total cardiopulmonary bypass of the heart during heart surgery with provisions for proximal aortic occlusion, aortic root cardioplegia delivery, aortic root venting, and left ventricular decompression. The system comprises a cardiopulmonary bypass pump which has an inlet port for reception of oxygen depleted blood from the venous circulation, and an outlet port for the delivery of oxygen-rich blood to arterial circulation. The blood is delivered to the patient through an arterial perfusion catheter which is comprised of a first flexible cannula member that has an axis of elongation, a distal and proximate end, and a first lumen that extends at least in part axially through the flexible cannula.

To deliver cardioplegia solution, a first proximate port on the cannula communicates with the first lumen and the cannula contains an orifice adjacent its distal end which is in communication with the first lumen thereby defining a single flow path for either the passage of cardioplegia solution or for the evacuation of fluid from the aortic root. The flexible cannula also has a second lumen extending at least in part axially therethrough and a balloon inflation port that communicates with the second lumen. There is also an inlet port which is in communication with both the second lumen and the inflation port. An inflation balloon is carried by the first cannula member adjacent its distal end and spaced in an axially proximate direction from the orifice where the balloon radially and sealingly encloses the inflation port and communicates with it.

In the delivery of oxygen-rich blood to arterial circulation, a second flexible cannula member is utilized which has a second axis of elongation and a distal and proximate end and an axially extending first cavity therethrough. A first opening located at the distal end of the cannula communicates with the first cavity to permit the passage of blood into the aorta. Additionally, the second cannula has a second axially extending cavity therethrough which is adapted for receiving the first cannula in order to permit relative slideable movement between the first and second cannulas. At its proximate end, the second cannula is connected to the outlet port of the cardiopulmonary bypass pump.

Selective flow of cardioplegia solution is accomplished through the use of a valve means that communicates with the first lumen to selectively permit the flow of cardioplegic solution within the single flow path when placed in one position and in another position the valve may be used for selectively evacuating fluid from the aortic root through the single flow path.

In providing for the transport of blood to the cardiopulmonary bypass pump from the patient, a venous catheter is utilized comprising a flexible cannula member which has an axis of elongation, a distal and proximal end, and an axially extending venous cavity therethrough; to provide for the inflation of the balloons to occlude the superior and inferior vena cava, the venous catheter has a first venous lumen extending at least in part axially through the catheter and a first venous inflation port which communicates with the first venous lumen. The flexible cannula member further has a second venous lumen which extends at least in part axially therethrough and a second venous inflation port which communicates with the second venous lumen. A first inflatable venous balloon is carried by the flexible cannula member adjacent its distal end and this inflatable balloon is used for occluding the superior vena cava. A plurality of first venous return ports are spaced intermediate the distal end of the flexible cannula member and the first inflatable venous balloon; the plurality of first venous return ports communicate with the venous cavity to permit the flow of blood from the superior vena cava into the catheter member. The second inflatable venous balloon is carried by the flexible member proximately of the first inflatable venous balloon for the purpose of occluding the inferior vena cava. The flexible member has a plurality of second venous return ports spaced proximately and adjacent the second inflatable venous balloon and which communicate with the venous cavity for receiving blood from the inferior vena cava. The second inflatable balloon radially and sealingly encloses and communicates with the second venous inflation port which permits inflation of the second inflatable venous balloon with a saline solution or other fluid. Such inflation occludes the inferior vena cava and thereby prevents blood flow from the inferior vena cava into the right atrium. A connecting member connects the flexible cannula member to the cardiopulmonary bypass pump so as to permit the venous cavity to be in fluid communication with the pump for the return of blood.

The catheter system described above for bypassing the heart during heart surgery also incorporates a plurality of radially and oppositely spaced steering lumens which extend at least in part axially through the flexible cannula; a plurality of steering cables, having first ends which are fixed to the flexible cannula member at its distal end extend axially through the steering lumens and the second ends of the steering cables are connected to a steering device which omnidirectionally permits the distal end of the first flexible cannula to articulate.

To position the arterial and venous catheters, a sensor member or marker is carried at a preselected location to delineate and position of the inflatable balloon, orifices, and distal tip of the catheter. In one embodiment the sensors generate an electric signal which is transformed into locational coordinates. The locational coordinates are visually presented to the surgeon which permits precise positioning of the balloons so as to permit the occlusion of the inferior and superior vena cava and the ascending aorta.

Another embodiment of the arterial catheter system for bypass support utilizes a first flexible cannula that has a third lumen which extends at least in part axially therethrough where the third lumen communicates with a decompression port located distally of the inflatable balloon. A plurality of second openings are located on the first flexible cannula adjacent the distal end of the cannula where the plurality of openings communicate with both the third lumen and the decompression port thereby defining a flow path for blood suctioned from the left ventricle. The plurality of second openings are spaced sufficiently axially and distally from the orifice so as to permit the plurality of second openings to communicate with the left ventricle on one side of the aortic valve while the orifice communicates with the aortic root on the cephalid side of the aortic valve. Thus, an arterial catheter is presented which permits suctioning of fluid from the aortic root while at the same time permits suctioning of blood from the left ventricle. To achieve added flexibility, the first flexible cannula includes a region of flexion which is located adjacent to and proximately of the inflatable balloon. This region of flexion has less flexural rigidity than the flexural rigidity of the cannula which permits enhanced elastic bending of the cannula within the region of flexion.

In yet another embodiment of the catheter system of this invention, the venous catheter device for occluding the superior vena cava and inferior vena cava has a first flexible cannula and a first venous lumen extending at least in part axially therethrough and a first inflation port that communicates with the first lumen. Isolation of the right atrium is achieved by occluding the superior and inferior vena cava. A first inflatable balloon is carried by the first flexible cannula adjacent its distal end for occluding the superior vena cava. To receive blood from venous ciruclation, an orifice which is spaced distally of the first inflatable balloon communicates with the cavity and permits the flow of blood from the superior vena cava into the cavity. A second flexible cannula has a second cavity which is adapted for receiving the first cannula to permit relative slideable movement between the first and second cannulas where the second cannula has a second inflatable balloon carried at its distal end for occluding the inferior vena cava and also has a plurality of venous return ports which are spaced proximately of and adjacent to the inflatable balloon. These return ports communicate with a third cavity for receiving blood from the inferior vena cava.

To achieve cardiopulmonary bypass pump support during heart surgery, a method is provided which comprises: (a) the insertion of an arterial perfusion catheter into a preselected arterial vessel of sufficient radial dimensions to permit the passage of the arterial perfusion catheter through the vessel and into the ascending aorta. An inflatable balloon is carried at the distal tip of the arterial perfusion catheter for occluding the aorta so as to occlude blood flow from the left ventricle when the balloon is inflated. The arterial catheter also has a second lumen for delivering a cardioplegia solution into the aortic root distally of the inflatable balloon and a third lumen to deliver blood from the cardiopulmonary bypass pump into the ascending aorta proximately of the balloon; (b) advancing the arterial catheter within the arterial vessel and positioning the balloon in the ascending aorta cephalid of the junction of the coronary arteries with the aortic root; (c) inserting a venous perfusion catheter into a preselected vein having sufficient radial dimensions to permit passage of the venous perfusion catheter through the vein and into communication with the superior and inferior vena cava entrances into the right atrium. The venous catheter carries a first inflatable balloon adjacent the tip of the venous catheter for occluding the superior vena cava and a second inflatable balloon carried by the venous catheter located proximately of the first balloon for occluding the inferior vena cava thereby precluding blood flow into the right atrium. The venous catheter has a first conduit communicating with the first and second inflatable balloons to provide fluid to the balloons for inflating them and the catheter also has a second conduit for receiving blood from the superior and inferior vena cava for delivering blood to the intake of the cardiopulmonary bypass pump; (d) advancing the venous catheter within the vein and positioning the first and second balloons in the superior vena cava and inferior vena cava respectively so as to preclude blood flow into the right atrium upon inflation of the balloons; (e) connecting the arterial catheter to the cardiopulmonary bypass pump such that the third lumen of the arterial catheter is in communication with the outlet port of the cardiopulmonary bypass pump and connecting the venous catheter to the cardiopulmonary bypass pump so that the second conduit of the venous catheter is in communication with the inlet port of the cardiopulmonary bypass pump; (f) after the steps described in (a), (b), (c), (d) and (e) above, the step of activating the cardiopulmonary bypass pump; (g) after performing the step described in (f), the step of inflating the inflatable balloon carried by the arterial perfusion catheter sufficiently to occlude the passage of blood from the aortic root into systemic arterial circulation; (h) after performing the steps set forth in paragraph (g), the step of injecting cardioplegia solution into the aortic root to arrest the heart; and (i) inflating the first and second balloons sufficiently to preclude blood flow from the inferior and superior vena cava respectively into the right atrium thereby completing isolation of the heart and establishing total cardiopulmonary bypass support.

Thus, a catheter system has been set forth for providing cardiopulmonary bypass pump support during heart surgery which may be utilized during minimally invasive procedures or utilized when a median sternotomy or major thoracotomy is performed. The catheter system allows the catheters to be inserted peripherally. In minimally invasive surgery this procedure avoids the need for a major chest incision such as thoracotomy or median sternotomy. The catheters may be positioned by using ultrasound imaging and sensor technology which eliminates the need for ionizing irradiation exposure as a means of locating the balloons and tip of the catheters. Precision positioning by ultrasound imaging can be achieved through the use of well-known techniques such as transesophageal, transthoracic, or an endoscopic echo probe placed between the ribs. The catheter system of this invention permits an arterial perfusion catheter to be peripherally inserted into arterial vessels, preferably into a femoral artery, and then advanced into the aortic arch; or the arterial perfusion catheter can be inserted into the left subclavian artery, advanced, and thereafter positioned in the aortic arch. Inserting the arterial catheter into the peripheral arterial vessels has the advantage of reducing the risk of embolism from cholesterol or calcium fragments which are frequently present in the ascending aorta. Such insertion also avoids surgical trauma to the ascending aorta and most importantly, eliminates the need for a median sternotomy incision or a major thoracotomy. The use of balloons on the catheter to occlude the aorta have the advantage of eliminating distortion and trauma to the aorta which occurs when a cross clamp is applied to occlude the aorta; the balloons can be inserted from a remote location thus eliminating the need for a sternotomy or major thoracotomy. If the aorta is brittle and heavily calcified or involved with cholesterol deposits, balloon occlusion nevertheless will be effective thereby avoiding abortive surgery. In circumstances where direct decompression of the left ventricular chamber is desired, this can be accomplished by the arterial catheter having an extended tip length which is of sufficient dimensions to traverse the aortic valve into the left ventricle. To decompress the left ventricle, the tip has a multiplicity of openings which communicate with a dedicated lumen connected to a suction source. This allows the evacuation of blood from the chamber and reduces the risk of overdistension.

BRIEF DESCRIPTION OF THE DRAWINGS

These and other features and advantages will become appreciated as the same become better understood with reference to the following specification, claims and drawings wherein:

FIG. 5 is a top view of FIG. 4.

FIG. 6 is a cross-sectional view along the lines 6—6.

FIG. 7 is a cross-sectional view along the lines 7—7.

FIG. 8 is in part, cross-sectional, view of one embodiment of a venous catheter.

FIG. 9 is a top view of the distal end of the venous catheter shown in FIG. 8.

FIG. 10 is a cross-sectional view taken along the lines 10—10.

FIG. 11 is another embodiment illustrating the distal portion of a venous catheter.

FIG. 12 is a side, part cross-sectional view, of FIG. 11.

FIG. 13 is a left end view of FIG. 12.

FIG. 14 is a cross-sectional view taken along the lines of 14—14 of FIG. 11.

FIG. 15 is a schematic view of the catheter system of this invention illustrating an embodiment of an arterial catheter for decompressing the left ventricle.

FIG. 16 is a part cross-sectional view of an arterial perfusion catheter of the type illustrated in FIG. 15.

FIG. 18 is a part phantom cross-sectional view illustrating an embodiment of the distal end of an arterial perfusion catheter.

FIG. 19 is a phantom and part cross-sectional view of another embodiment of an arterial perfusion catheter of this invention.

FIG. 21 is a schematic view illustrating an arterial perfusion catheter inserted through the femoral artery and a venous catheter occluding the superior and inferior vena cava.

FIG. 22 is a part cross-sectional side view of the arterial perfusion catheter illustrated in FIG. 21.

FIG. 23 is a partial cross-sectional view of the distal end of the venous catheter shown in FIG. 22.

FIG. 24 is a left end view of FIG. 22.

FIG. 25 is a right end cross-sectional view of FIG. 23.

FIG. 26 is a bottom view of FIG. 23.

FIG. 27 is a schematic view illustrating the catheter system of this invention with an arterial perfusion catheter inserted through the femoral artery and having an extended distal tip for decompressing the left ventricle.

FIG. 28 is a perspective view of a catheter steering method.

FIG. 29 is an exploded perspective view of a steering cable holder.

FIG. 30 is a part cross-sectional view illustrating another embodiment for catheter steering.

FIG. 32 is a cross-sectional view of taken along the lines 32—32 of FIG. 33.

FIG. 33 is a top view of FIG. 32.

FIG. 34 is a part cross-sectional perspective view of the embodiment shown in FIG. 30, schematically illustrating the ultrasound signal source for positioning the catheter in a body structure.

FIG. 35 is a part cross-sectional view illustrating the distal end of an arterial perfusion catheter.

FIG. 36 is a right side view of FIG. 35.

FIG. 37 is a perspective view illustrating the catheter sensor for detecting ultrasound and converting the sound energy into an electrical impulse.

FIG. 38 is a schematic view illustrating another embodiment of the arterial perfusion catheter of this invention inserted directly into the descending aorta.

FIG. 39 is an illustration of minimal invasive thoracopic placement in the aorta of the catheter shown in FIG. 38.

FIG. 40 is a perspective view of another embodiment of an arterial perfusion catheter.

FIG. 41 is a side view of the catheter shown in FIG. 40.

DETAILED DESCRIPTION

Figure 1:
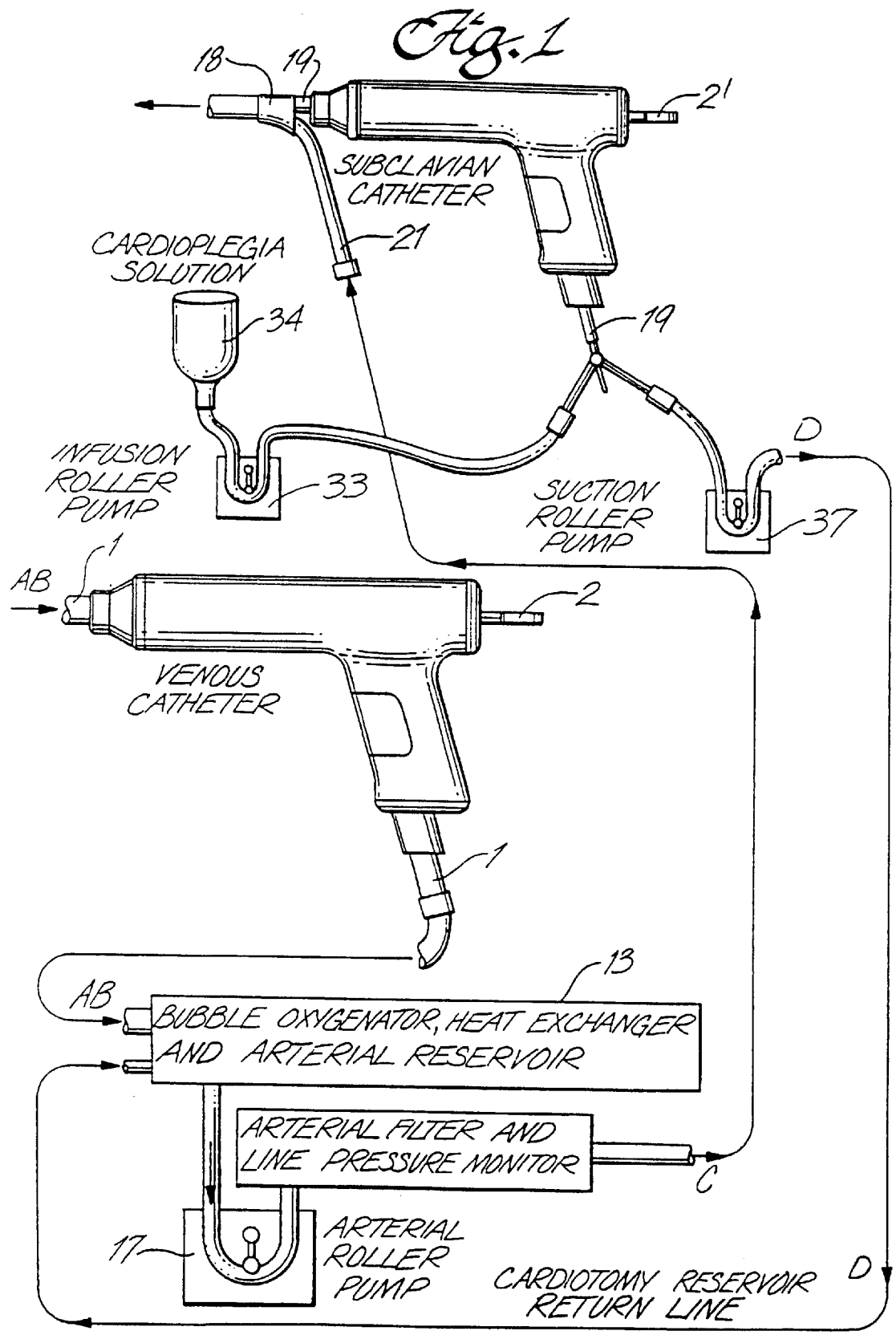
FIG. 1 is a schematic drawing illustrating a catheter system of this invention.

FIG. 1 is a schematic view illustrating a system of venous perfusion and arterial perfusion catheters for use in obtaining total cardiopulmonary bypass support and isolation of the heart during the performance of heart surgery. In general, the catheter system incorporates a venous catheter 1 which is inserted peripherally into the femoral vein and advanced through the femoral vein by a steering mechanism controlled by joy stick 2. By referring to FIG. 3, venous catheter 1 is then positioned either by ultrasound techniques or radiography such that the distal tip 3 extends into the superior vena cava 4. Superior vena cava 4 is occluded by the expander or balloon 6 which is located adjacent to distal tip 3 and placed cephalid to the atrio-caval junction 7. A second expander or balloon 8 carried by venous catheter 1 is spaced proximally from first expander or balloon 6 at a fixed distance and positioned proximately of the atrio-caval junction to occlude the inferior vena cava 9. As can be seen in FIG. first and second expanders or balloons straddle the atrio-caval junction 7 and when inflated isolate the heart from blood flow into the right atrium of the heart. Arrows A illustrate the blood flow from the superior vena cava 4 through a multiplicity of venous orifices 11 which are located in the distal tip 3 of venous catheter 1. These orifices communicate with axially extending venous cavity 12 which provides a flow path to the bubble oxygenator, heat exchanger and arterial reservoir 13 (shown on FIG. 1).

Blood flow into axially extending venous cavity 12 from the inferior vena cava 9 is shown by arrows B. Blood flow represented by arrow A also flows into venous cavity 12 through a plurality of venous return ports 14 which communicate with venous cavity 12. Similarly, a plurality of second venous return ports 16 communicate with venous cavity 12 to permit blood flow into cavity 12 for transportation to bubble oxygenator, heat exchanger and arterial reservoir 13 in the direction shown by arrow AB.

Figure 3:
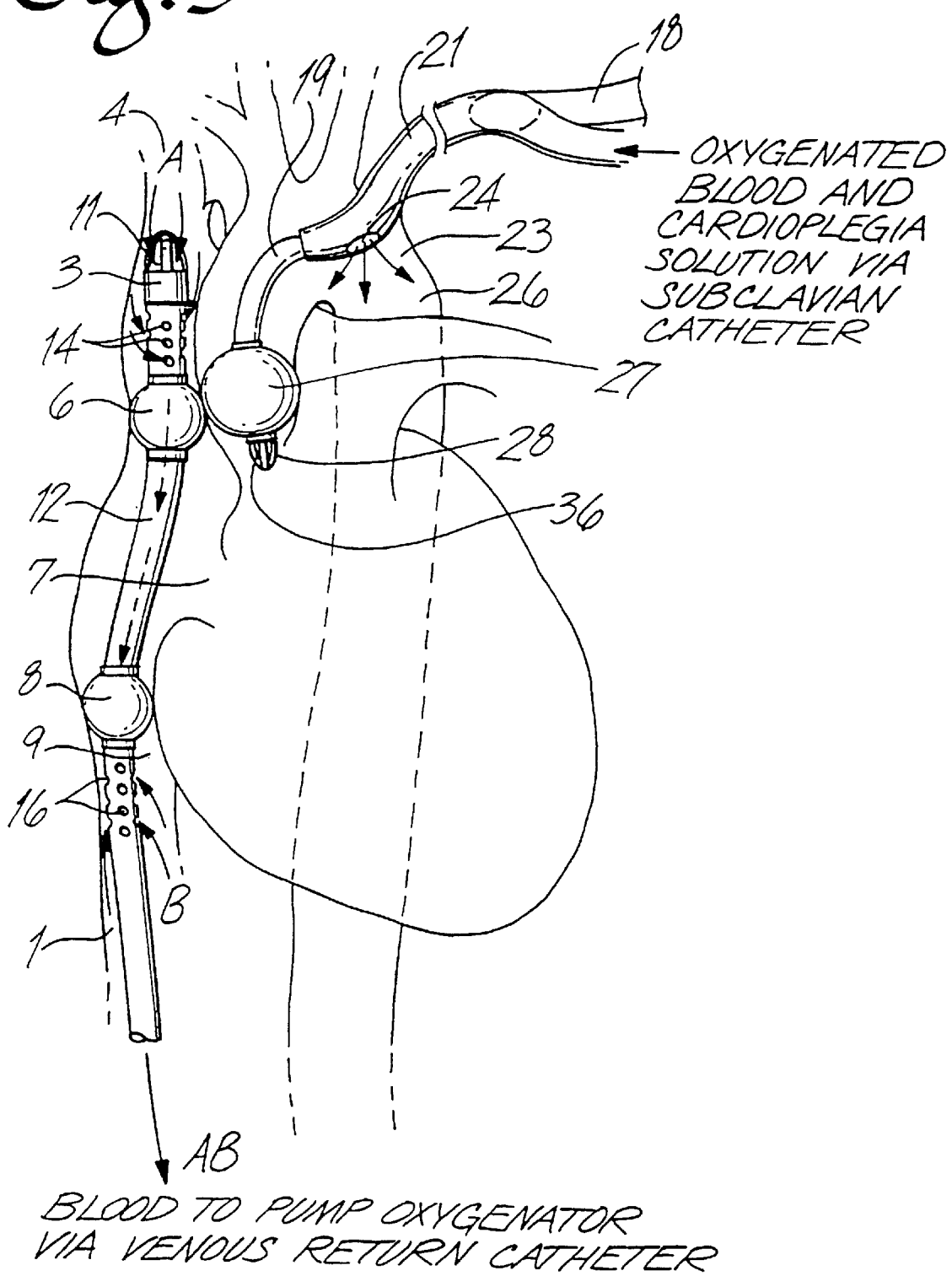
FIG. 3 is a schematic drawing illustrating positioning of the arterial and venous catheters to achieve cardiopulmonary bypass support.

Referring again to FIG. 1, it can be seen that the blood is directed from bubble oxygenator 13 into arterial roller pump 17 from which oxygenated blood is returned to arterial circulation as shown by arrow C. Venous catheter 1 as shown and described in both FIGS. 1 and 3, is one embodiment of the venous perfusion catheters of this invention which will be described in greater detail below. Likewise, the arterial perfusion catheters of this invention will be described in several embodiments hereafter; however, for the purpose of describing a system embodiment of a venous catheter and arterial catheter system to achieve total cardiopulmonary bypass, further reference to FIGS. 1 and 3 will be made for the purpose of an orderly presentation of the various systems and catheter structures of this invention.

Further reference is now made to FIG. 1 wherein an embodiment of the perfusion arterial catheter of this invention is referred to as a subclavian catheter 18. Subclavian catheter 18 is comprised of two cannulas, namely first flexible cannula member 19 and second flexible cannula member 21 (illustrated in FIG. 3).

Figure 2:
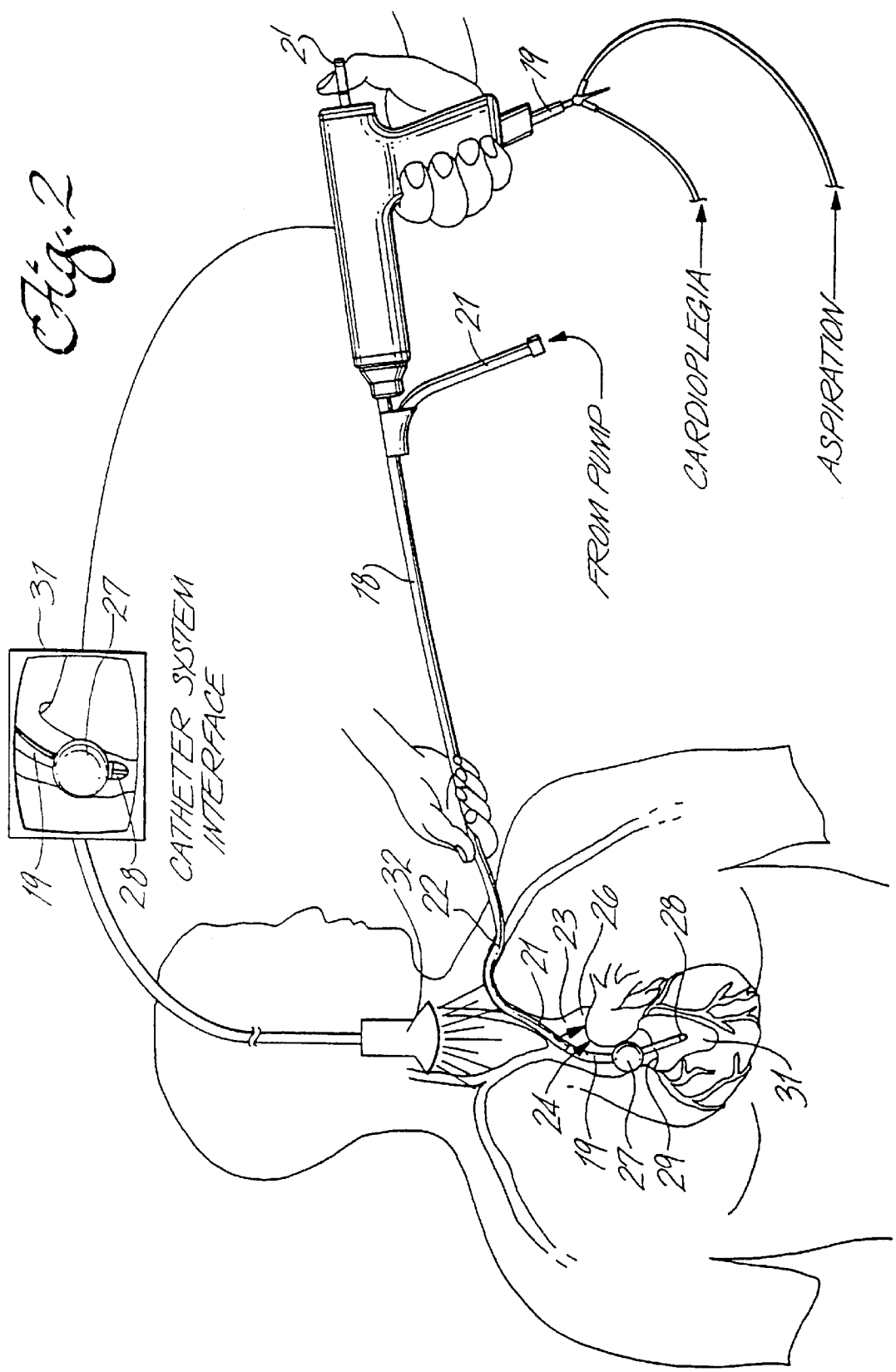
FIG. 2 is a schematic drawing of an arterial perfusion catheter inserted into the subclavian artery.

In FIG. 2, the insertion of arterial perfusion catheter 18 into subclavian artery 22 is schematically illustrated. As can be seen in FIG. 2, the catheter 18 is steered by arterial catheter joy stick 2' into the aortic arch 23 such that first opening 24 of second flexible cannula 21 is positioned adjacent the descending or thorasic aorta 26. This permits the flow of oxygenated blood from the cardiopulmonary bypass pump into arterial circulation. By referring to both FIGS. 2 and 3, it can be seen that first flexible cannula 19 is slideably extendable from second flexible cannula 21 and has an inflatable balloon 27 adjacent its distal tip 28. In one embodiment, distal tip 28 is spaced a sufficient fixed distance from inflatable balloon 27 to transverse the aortic valve; in another embodiment, as shown in FIG. 3, the distal tip 28 is directly adjacent inflatable balloon 27, and in yet another embodiment, distal tip 28 is extendable distally relative to inflatable balloon 27 to permit the distal-tip 28 to be advanced across the aortic valve 19 and into the left ventricle 31. Inflatable balloon 27 may be positioned in the ascending aorta by utilizing ultrasound techniques or fluoroscopic imagery.

FIG. 2 illustrates the use of a catheter system interface 31 where an ultrasonic image of scanned tissue is presented on a television monitor. A transopical echo device 32 is positioned behind the heart in the esophagus where the ultrasonic sound waves emitted from the device reflect from both the body tissue and the catheter, thereby assisting the surgeon in precisely positioning inflatable balloon 27 in the aortic root just above the aortic valve and coronary artery orifices (ostias).

Again referring to the schematic of FIG. 1, first flexible cannula 19 may be selectively placed in communication with an infusion roller pump 33 for the delivery of a cardioplegia solution 34 to the aortic root through the orifices 36 contained in distal tip 28 of first flexible cannula 19 or for venting blood from the aortic root into suction roller pump 37 where the vented blood is returned as shown by arrow D through the cardiotomy reservoir return line to the bubble oxygenator and heat exchanger 13. The vented blood is thereafter oxygenated and then delivered to the arterial roller pump 17 where it is returned into arterial circulation as shown by arrow C (FIG. 1).

Figure 4:
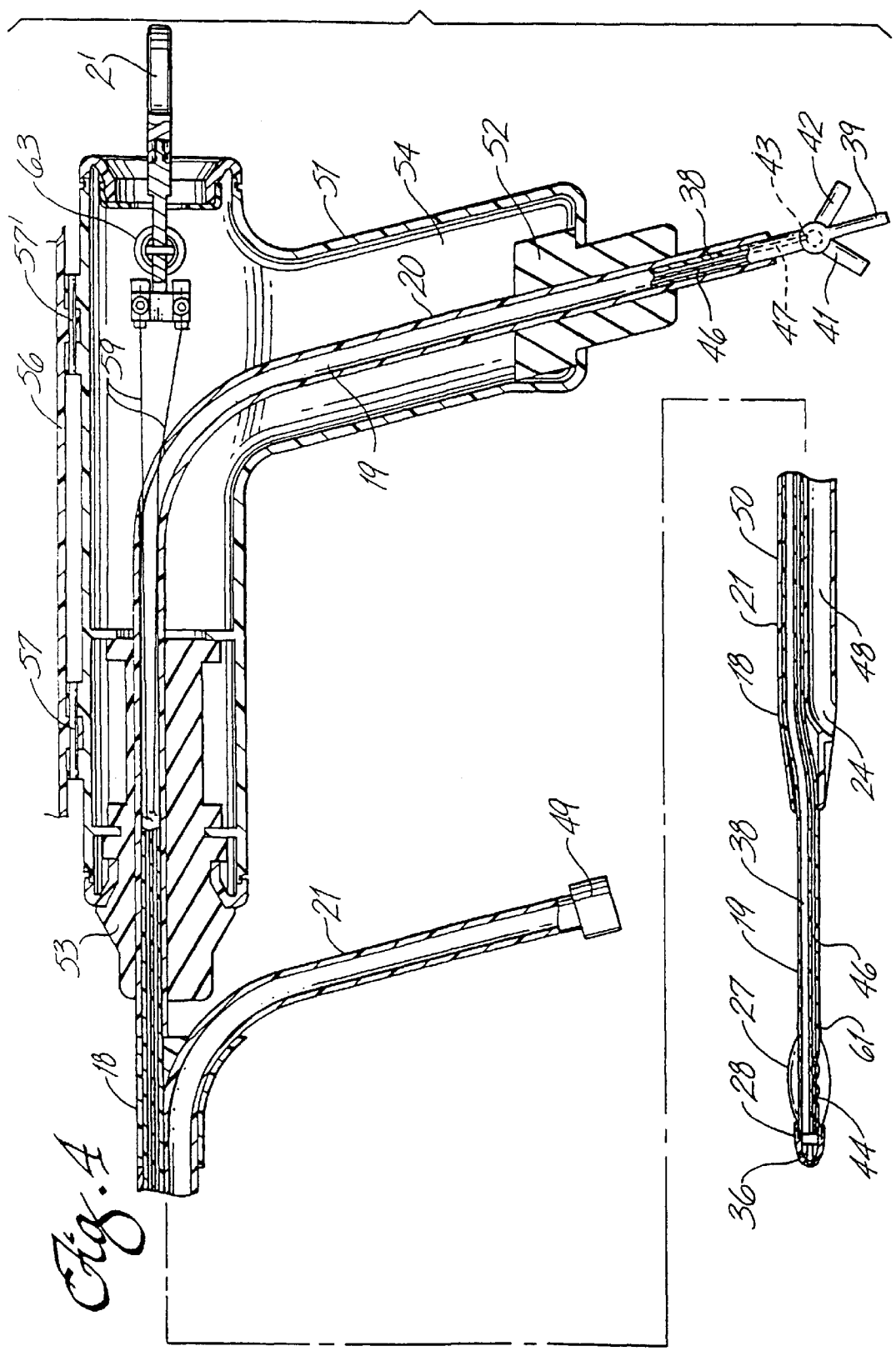
FIG. 4 is an in-part cross-sectional view of one embodiment of an arterial perfusion catheter.

The embodiment of catheter 18, illustrated in FIG. 3, is set forth in greater detail in FIGS. 4, 5, 6, 7 and 7a. Referring to FIG. 4, arterial perfusion catheter 18 has a first flexible cannula member 19 which has an axially extending first arterial lumen 38 that communicates with a plurality of orifices 36 located in the distal tip 28 of first flexible cannula member 19. The proximal end of first flexible cannula member 19 is connected to two-way connector switch 39 which permits selective communication between first lumen 38 and infusion roller pump 34 or suction roller pump 37 through cardioplegia connector 41 and aspiration connector 42. Both cardioplegia connector 41 and aspiration connector 42 communicate with first proximate port 43 such that first lumen 38 may selectively either provide a fluid route for the delivery of cardioplegia solution to distal orifices 36 or to permit the aspiration of blood from the aortic root cephalid of the coronary artery ostia. To occlude the ascending aorta cephalid of the coronary artery junction, an inflatable balloon 27 is carried by first flexible cannula member 19 adjacent distal tip 28 of the catheter. A multiplicity of inflation ports 44 communicate with a second arterial lumen 46 which extends axially in part within first flexible member 19 and communicates with arterial inlet port 47. Although not shown in FIG. 4, arterial inlet port 47 communicates with a balloon inflation-deflation syringe source 43 which may inject either a saline or other biocompatible fluid solution into the balloon to inflate it sufficiently to occlude the ascending aorta at a location adjacent and cephalid of the junction of the coronary arteries. Thus, an arterial perfusion catheter is provided which has the advantage of occluding the aorta by eliminating the distortion and trauma to it which would occur if a vascular clamp were applied to the aorta externally to occlude left ventricular flow into the aorta.

The return of oxygenated blood to arterial circulation is achieved through first opening 24 which communicates with first arterial cavity 48. Arterial cavity 48 extends axially through second flexible cannula 21 to provide a flow channel from the cardiopulmonary bypass pump to which it is connected at its proximal end by connector 49.

A handpiece 51 is shown in FIG. 4 which can be used interchangeably with either the venous catheter or arterial catheter embodiments of the catheter systems of this invention. As can be seen in FIG. 4, a cross-section is shown of handpiece 51 within which first flexible cannula member 19 is held in fixed relationship with the handpiece by plug members 52 and 53 and catheter housing 20. Plug members 52 and 53, and housing 20, are composed of two sections which are mirror images of each other and are carried by the mating frame members 54 and 56. The frame members are hinged together by hinges 57 and 57'. The hinging of the mating frame members permits the handpiece to be opened and allows the catheter, whether an arterial perfusion catheter or venous perfusion catheter, to be removably mountable to the handpiece.

By referring to FIG. 5 which is a top view of FIG. 4, mating frame members 54 and 56 are shown in closed position with first flexible cannula 19 clamped therebetween. By reference to FIG. 7a which is an enlarged view of FIG. 7, it can be seen that first cannula member 19 has four steering lumens 58 which extend in part axially through the cannula to permit steering wires 59 to pass through cannula 19 in slideable relationship where the distal ends of the steering wires 59 are connected to the distal tip of the first flexible cannula member as is more definitively illustrated in FIGS. 35, 36 and 37. The steering mechanism for handpiece 51 and steering wire relationship to the catheter will be more fully detailed hereinafter, however, it will be appreciated that through the manipulation of joy stick 2' appropriate linkage permits steering wires 59 to be placed in tension relative to each other thereby permitting the distal tip of the catheter to articulate.

Referring again to FIG. 7a, it can be seen that a clearance 61 exists between first flexible cannula 19 and second flexible cannula 21 to permit flexible cannula 19 to be advanced through cannula 21. Preferably this clearance is 0.01". Thus, by gripping handpiece 51, the surgeon by moving the handpiece in either direction horizontally will induce the slideable advance of first cannula 19 within second cannula 21. This arrangement permits the surgeon to position first opening 24 of second flexible cannula 21 in the aortic arch and thereafter to slide first cannula 19 relative to second cannula 21 so as to position inflatable balloon 27 in the aortic root. A first sensor 61 is carried by first flexible cannula 19 proximally of balloon 27 and a second sensor 62 shown on FIG. 5 is positioned at the distal end of the balloon 27 where the sensors may be made of a material that efficiently reflects ultrasonic waves. These ultrasound waves are detectable by a device such as a transophical echo device 32 (FIG. 2) for a clear presentation of the extremities of inflatable balloon 27 so as to more precisely position the balloon in the aortic arch cephalid of the junction of the coronary arteries. Other embodiments of the catheter may utilize a reflective material to promote fluoroscopic imaging of the balloon extremities to properly position the balloon in the aortic root; reflective materials such as barium sulfate or bismouth subcarbonate are well known in the prior art of fluoroscopy. The cannulas 19 and 21 may also be in part impregnated with radiopaque materials such as barium sulfate, bismouth subcarbonate or iodine containing molecules; or impregnated with tungsten, or fillers such as plasticizers or other pigmentation or anti-oxidents, or coated with Heparin or anti-thrombogenic agents to promote visualization of the catheter and balloon within the arterial vessel and aortic wall. There are well known materials in the prior art for use in constructing the balloon such as silicon rubber, polyurethane, latex nylon, polyamide, and polyethylene. Likewise, cannulas 19 and 21 may be made of known materials in the prior art such as silicon rubber, polyvinyl chloride, polyurethane, or other suitable materials such as ethylene or nylon. Catheter sizes may vary from 12–35 French with 4–12 mm outside diameter and have lengths from 40–120 cm to accommodate flow rates of 0.5 to 8.0 liters per minute.

By referring to FIG. 6 it can be seen that the distal tip of first flexible cannula 19 has a plurality of orifices 36 which communicate with first lumen 38 thereby permitting the flow of either cardioplegia solution into the aortic root or the aspiration of blood from the aortic root. Distal tip 28 is tapered to permit ease of passage of cannula member 19 as it is advanced through an arterial vessel.

One embodiment of the venous perfusion catheter of this invention is shown in FIG. 3. This embodiment is removably mountable to the handpiece 51 and is more definitively illustrated in FIG. 8. As previously described, handpiece 51 has a joy stick member 2 which is connected to a steering mechanism 63 for articulating the tip 3 of the venous catheter 1 so as to position tip 3 in the superior vena cava and position inflatable balloons 6 and 8 to straddle the atriocaval junction. Upon inflation of the balloons, the superior and inferior vena cava are occluded and the heart isolated. As in the construction of the arterial perfusion catheter, the distal tip 3 of venous catheter is tapered to promote passage through the femoral vein.

By referring again to FIG. 8, axially extending venous cavity 12 provides a flow path for blood which is suctioned from the superior vena cava through the multiplicity of orifices 11 located at the distal tip and also through the plurality of first venous return ports 14. Second venous return ports 16 also communicate with axially extending venous cavity 12 to permit passage of blood from the inferior vena cava into the cavity for transport to the cardiopulmonary bypass pump. To accurately position first inflatable balloon 6 in the superior vena cava at the atriocaval junction, a pair of venous sensors 64 and 66 are carried by venous catheter 1 and located at the distal and proximal ends of first inflatable balloon 6. Venous sensors 64 and 66 may be made of a material reflective of ultrasound or coated with a piezoelectric material. The piezoelectric material may generate an electric signal to be carried by steering wires 67 and 68 for transmission to a catheter system interface and thereafter presented on a monitor to assist the surgeon in visualizing the distal and proximal ends of the first inflatable balloon during its passage through the femoral vein and ultimate positioning in the atrio-caval junction. Sensors 64 and 66 may alternatively be radiopaque markers for use in fluoroscopically imaging the location of the balloon.

To inflate the balloons, a first venous inflation port communicates with first inflatable balloon 6 and a first venous lumen 70 extends in part axially through venous catheter 1 and ultimately communicates with a syringe device for injecting saline solution or other biocompatible fluid through the first venous lumen and into first inflatable balloon 6 for expanding the balloon until it circumferencially bears against the vessel wall of the superior vena cava thereby precluding blood flow around the balloon. Blood therefore returning from the superior vena cava for delivery into the right atrium will pass through the multiplicity of orifices 11 at the distal tip of catheter 1 and also through the plurality of venous return ports 14 which are located distally of first inflatable balloon 6. Likewise, second inflatable balloon 8 is straddled by a pair of sensors 71 and 72 which may be coated with a piezoelectric material or made of an ultrasound reflective material; alternatively, the sensors may be radiopaque markers for fluoroscopically imaging the location of the second inflatable balloon in the femoral vein.

As can further be seen in FIG. 8, a second inflation port 73 communicates with second inflatable balloon 8 and also communicates with a second venous lumen 74 to permit the passage of a saline solution or other fluid into the second inflatable balloon. A remote opening 76 communicates with second lumen 74 to permit the insertion of a syringe into the second lumen for injecting a saline solution or other fluid to inflate second inflatable balloon 8. The inferior vena cava is occluded by the inflation of second inflatable balloon 8 and thus blood which is flowing toward the right atrium after the balloon is inflated will be precluded from flowing past the balloon and will enter into axially extending venous cavity 12 through second venous return ports 16. The blood is then transported directly to the intake side of the cardiopulmonary bypass pump to which the venous catheter 1 is connected by venous connector 77.

By referring to FIG. 9 it can be seen that the distal tip of the venous catheter 3 has a distal sensor 78. Sensor 78 may also be coated with a piezoelectric material or be made of a suitable ultrasound reflective material, or may be a radiopaque marker for fluoroscopically imaging the location of the distal tip of the catheter. By reference to FIG. 10, first venous lumen 70 is radially spaced oppositely from second venous lumen 69; and steering wires 67 and 68 pass through steering lumens 79 and 81 respectively. As will be more clearly shown hereafter, the steering wires permit articulation of the distal tip of the catheter to promote passage of the catheter and advancement within an arterial or venous structure.

Another embodiment of a venous perfusion catheter 1' is shown in FIGS. 11, 12, 13, 14 and 14a. This catheter performs the identical function as venous catheter 1 described above, however, venous catheter 1' utilizes a structure which permits the spacing between the first and second inflatable balloons to be adjustable thereby enhancing the universality of use of catheter 1'.

Referring now to FIG. 12, it can be seen that venous catheter 1' is comprised of a first venous flexible cannula 82 which is in part slideably contained for slideable axial movement relative to second flexible cannula 83. First flexible cannula 82 because of its slideable relationship with second flexible cannula 83 permits the distance between first inflatable balloon 6' and second inflatable balloon 8' to be varied. This slideable relationship between first inflatable balloon 6' and second inflatable balloon 8' permits this embodiment, venous perfusion catheter 1', to be used with a greater spectrum of patients than the venous catheter embodiment described above. As in the previous embodiment, the first and second inflatable balloons are positioned by the surgeon through the use of sensors 64' and 66' which respectively straddle first inflatable balloon 6' at its proximal and distal ends; similarly, second inflatable balloon 8' has sensors 71' and 72' which likewise straddle inflatable balloon 8' respectively at its distal and proximal ends. Sensors 64', 66', 71' and 72' may be made of a material which is reflective of ultrasonic waves or coated with a piezoelectric material to convert ultrasound energy into an electrical signal by methods which are well known in the prior art. Such signals may be transformed into an image presentable on a video monitor to assist the surgeon in identifying the exact location of the balloon extremities before inflation. Radiopaque markers may also be used to delineate the location of the balloons and fluoroscopically imaged to again assist the surgeon in locating the balloon relative to the atrio-caval junction.

Inflation of the first inflatable balloon after it is positioned in the superior vena cava is achieved through the injection of a saline solution or other biocompatible fluid by a syringe (not shown) where the fluid is transported through first venous lumen 70' which is contained within first flexible cannula member 82 and communicates with first venous inflation port 86. Port 86 in turn communicates with the internal region of the first inflatable balloon. To inflate second inflatable balloon 8', a second venous lumen 69' (shown in FIG. 14a) communicates with second venous inflation port 73' which in turn communicates with the internal region of the second inflatable balloon such that a saline fluid remotely injected into the second lumen (not shown) may inflate the second inflatable balloon after it has been positioned in the inferior vena cava.

Venous perfusion catheter 1' has a multiplicity of orifices 11' located in its distal tip 3' which redirect blood flowing through the superior vena cava toward the right atrium into axially extending venous cavity 12' where the blood is transported through cavity 12' to the cardiopulmonary bypass pump. Blood flowing through the inferior vena cava is prevented from reaching the right atrium by the inflation of second inflatable balloon 73' and the blood therefore flows through the plurality of venous return ports 16' into a third axially extending venous cavity 87 where the blood is transported through axially extending venous cavity 87 to the cardiopulmonary bypass pump. Although not shown in the drawings, prior to the blood being delivered to the cardiopulmonary bypass pump, a junction is formed to permit the confluence of the blood flow in axially extending venous cavity 87 and axially extending venous cavity 12'. The confluence then is directed into the intake of the cardiopulmonary bypass pump.

Figure 14A:
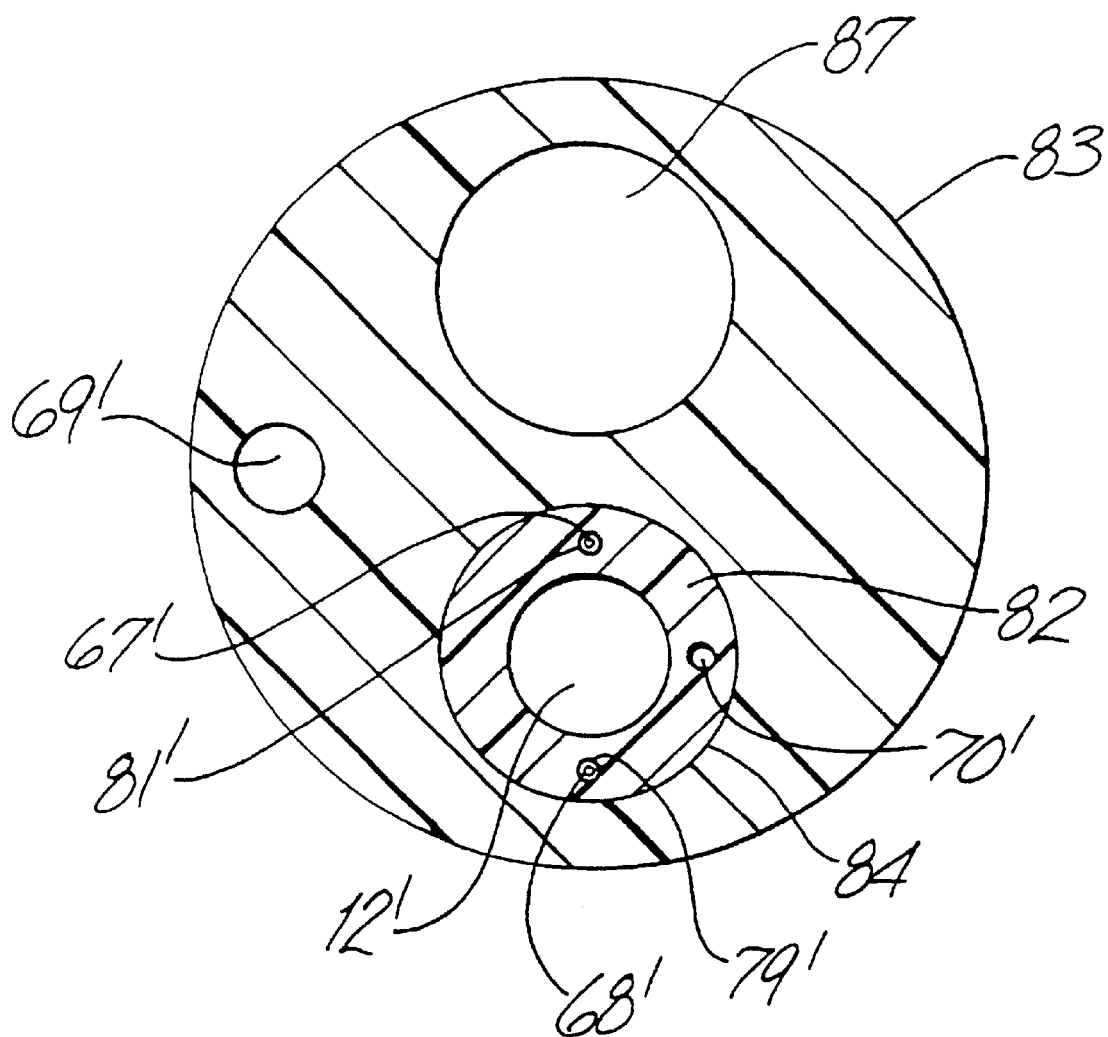
FIG. 14A is an enlarged view of FIG. 14.
Figure 17:
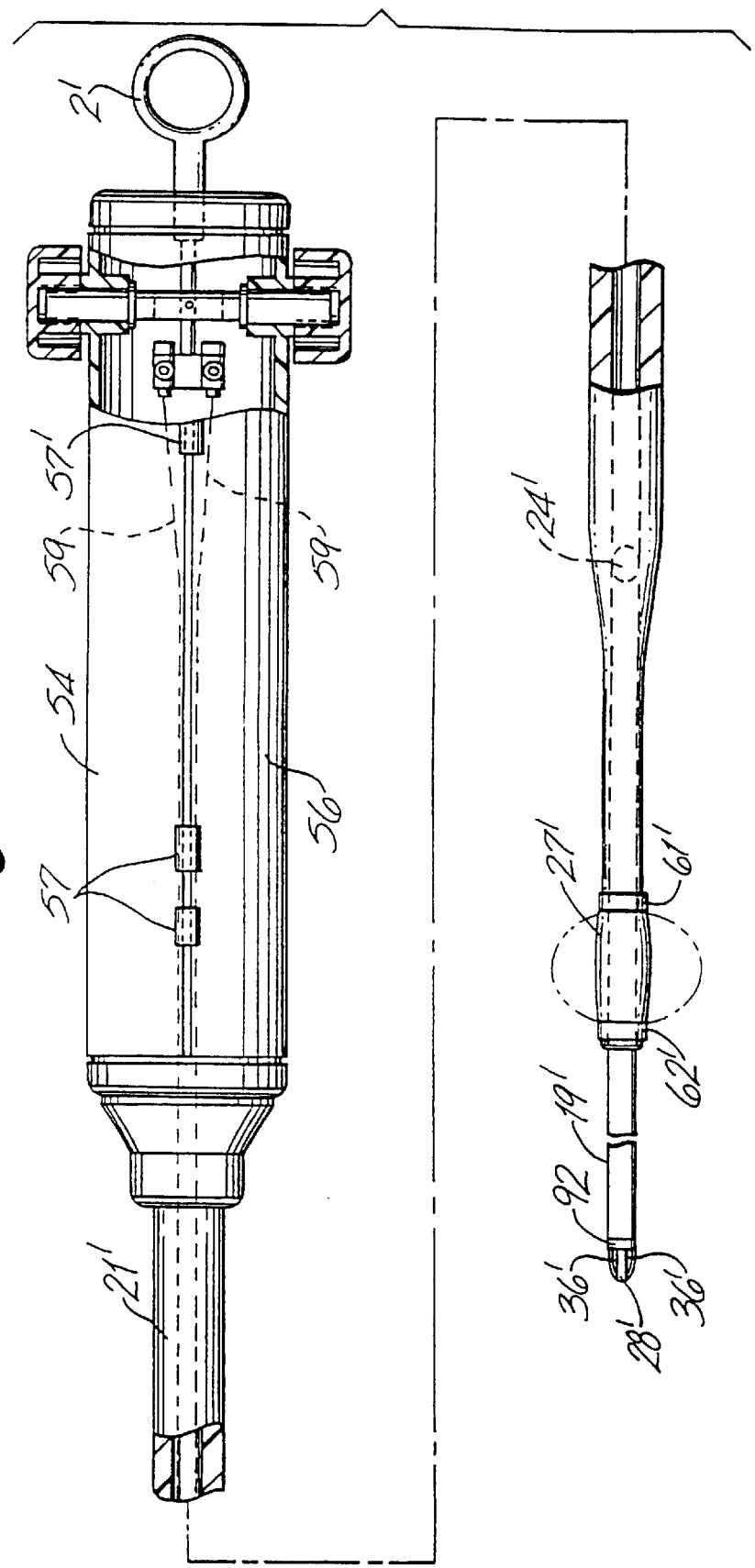
FIG. 17 is a part cross-sectional top view of FIG. 16.

By referring to FIG. 14a, it can be seen that first flexible cannula 82 has a pair of opposing venous steering lumens 79' and 81' where steering wires 68' and 67' extend axially through the lumens; the steering wires connect to a steering mechanism which is described below.

Venous perfusion catheter 1' is preferably inserted into the femoral vein in the groin region and then advanced through the femoral vein to the atrio-caval junction by steering first venous flexible cannula member 82. This is accomplished by the application of opposing tension to steering wires 67' and 68'. Venous catheter 1' may also be advanced through the femoral vein through the use of a guide wire which is first introduced into the vein and then advanced through appropriate imaging to the atrio-caval junction. The proximal end of the wire may then be inserted through orifice 11' of first flexible cannula 82 and cannula 1' advanced along the guide wire until it reaches the atrio-caval junction where the balloons are then positioned and inflated.

Although not shown in the figures, isolation of the heart may be achieved by utilizing two venous perfusion catheters of identical construction. These catheters would each have an inflatable balloon at their distal ends. One of the catheters would be inserted through a peripheral vein, the jugular vein for example, and the distal tip advanced into the superior vena cava and positioned to occlude the superior vena cava at the atrio-caval junction. Orifices located proximally of the balloon would permit blood flowing toward the right atrium to be diverted into a conduit within the catheter for transport to the cardiopulmonary by-pass machine. Similarly, the other catheter of like structure would be inserted through the femoral vein and advanced and positioned in the inferior vena cava at the atrio-caval junction, inflated, and blood flow redirected through orifices located proximally of the balloon to the cardiopulmonary bypass pump.

Other embodiments of arterial perfusion catheters of this invention are illustrated in FIGS. 15 through 19.

Each of the arterial perfusion catheters described in FIGS. 15 through 19 embody an extended distal portion which may be extended across the aortic valve and into the left ventricle to provide a left ventricle venting function;

cardioplegia solution may still be delivered into the aortic root as in the above-described embodiments of the arterial perfusion catheter or the same flow path may be used for aspiration of the aortic root. FIG. 15 is an illustration of one embodiment of an arterial perfusion catheter where the first flexible cannula 19 has a fixed distance between the distal tip 28 of the catheter and the inflatable balloon 27. Other embodiments, shown in FIGS. 16, 18 and 19 illustrate the distal portion of arterial catheters where the arterial perfusion catheter has a first flexible cannula portion which is extendable from the second flexible cannula 21 after balloon 27 is positioned in the aortic arch. Referring now to FIG. 16, the handpiece 54 which was previously described is again utilized to carry first flexible arterial cannula 19'. Cannula 19' may be made of the same materials of previous catheter embodiments described above. First arterial catheter 19' has a distal tip 28' which is tapered to accommodate the passage of the catheter through the arterial vessels. A plurality of second openings 36' are located in distal tip 28 and communicate with third arterial lumen 88 which extends axially through flexible cannula 19' to provide a flow channel for blood vented from the left ventricle decompression roller pump 40 (shown in FIG. 38) where the blood is pumped thereafter to the arterial reservoir.

A second flexible cannula 21' is shown in FIG. 16 where first flexible cannula 19' slideably extends through second arterial cavity 50' contained in second flexible cannula 21'. To deliver blood to arterial circulation, second flexible cannula 21' has a first arterial cavity 48' which has a first opening 24'. First opening 24' communicates with first arterial cavity 48' which in turn communicates with the outlet side of the cardiopulmonary bypass pump and is connected to the pump by connector 49'. Second cannula member 21' at its distal end 89 carries an inflatable balloon 27" which is expandable so as to permit occlusion of the aortic arch. As can be seen in FIG. 16, a plurality of inflation ports 44' communicate with the internal region of inflatable balloon 27' and also with second arterial lumen 46' which extends axially through second flexible cannula 21' and communicates with arterial inflation port 90. A suitable connector may be attached to second flexible cannula 21' to provide for the injection of a saline or other solution to permit the surgeon to selectively expand balloon 27'.

Venting of the aortic root is accomplished through the use of a multiplicity of arterial venting orifices 91 which communicate with first arterial lumen 38'. Arterial lumen 38' extends at least in part axially through first flexible cannula 19'. A first proximate port 43' communicates with first lumen 38' at the junction of first flexible cannula member 19 with selector switch 39'. Selector switch 39' allows the surgeon to selectively place first lumen 38' in communication with either cardioplegia connector 41' or aspiration connector 42'; thus the surgeon may selectively introduce a cardioplegia solution through cardioplegia connector 41' where the solution under pressure of a infusion roller pump is pumped through first lumen 38' to arterial venting orifices 91' for delivery into the aortic root. Alternatively, the surgeon may place selector switch 39' in a second position whereby aspirator connector 42' communicates with a suction roller pump and places first lumen 38' in communication with the pump for aspirating fluid from the aortic root.

Figure 7A:
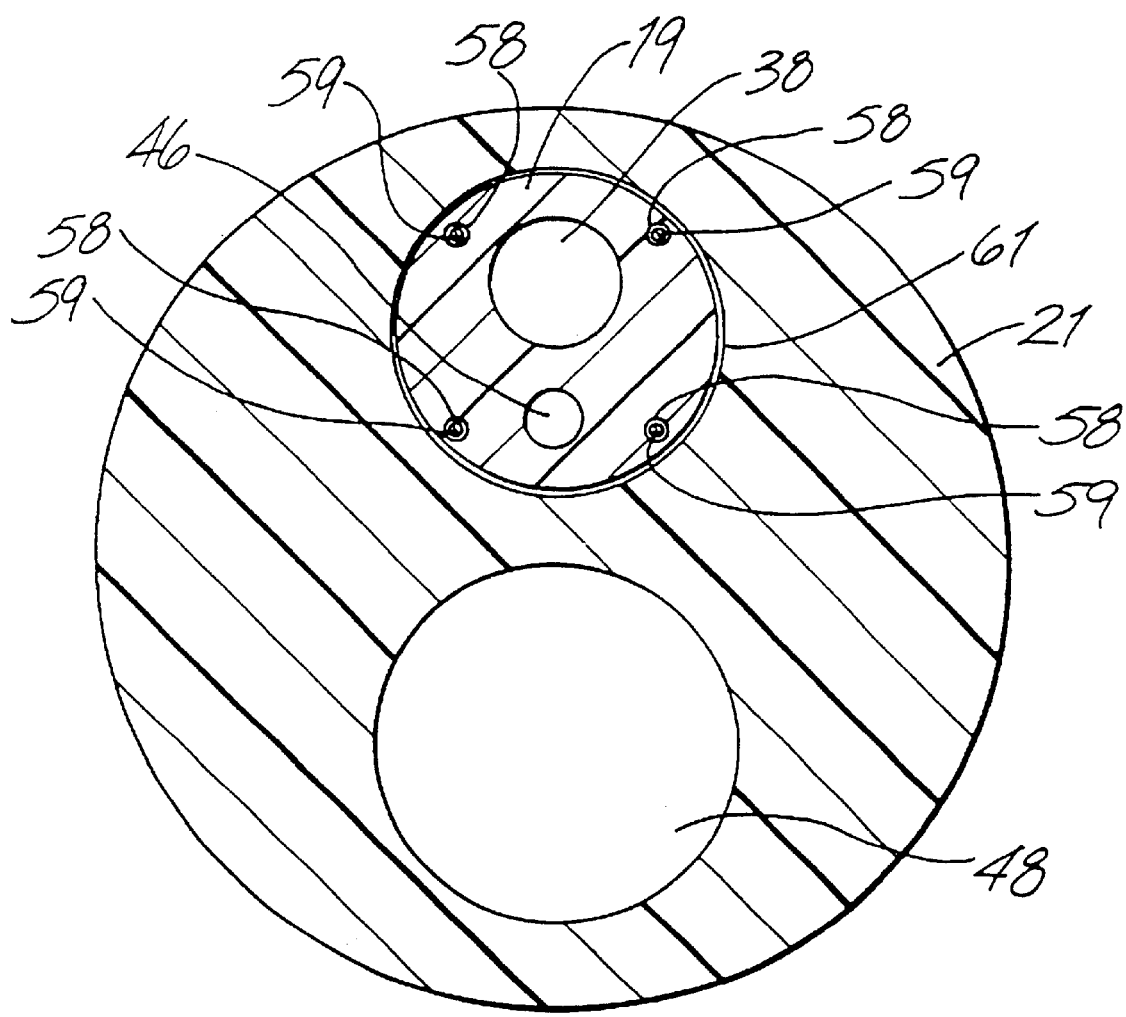
FIG. 7A is an enlarged view of FIG. 7.

As previously described in FIG. 5, the handpiece 51 provides for the inter-changeability of the various venous perfusion and arterial perfusion catheter embodiments of this invention. First flexible cannula member 19' is clamped between mating frame members 54 and 56 of handpiece 51 and securely held by plug members 52 and 53. Although not illustrated, first flexible cannula member 19' is steerable through the use of opposing steering wires 59' which are carried by cannula 19' and extend through a plurality of steering lumens as shown in FIG. 7a where the steering lumens are identified by numeral 58. Steering wires 59' are connectable to the steering mechanism 63 such that my manipulation of the joy stick 2' the tension in steering wires 59' may be varied which will allow the distal tip of flexible catheter 19' to articulate so as to permit the surgeon to advance the catheter through the arterial vessel. The steering mechanism 63 relationship with handpiece 54 is described below in more detail.

To assist the surgeon in locating the distal tip 28' of arterial perfusion catheter 18' and also to position balloon 27' in the aortic arch, a sensor 92 is fixed adjacent the distal end 28' of first flexible cannula member 19' where sensor 92 may be made of a ultrasonic reflective material, or coated with a piezoelectric material or may be a radiopaque marker for flouroscopically imaging the distal tip 28' of the catheter. Sensors 61' and 62' are fixed to second flexible cannula member 21' adjacent the proximal and distal ends of balloon 27' respectively. These sensors perform the identical function of those sensors previously identified which straddle the inflatable balloons on the venous perfusion and arterial perfusion catheter embodiments of this invention. By referring to FIG. 17, which is a top view of FIG. 16, it can be seen that sensors 61', 62' and 92 circumferencially enclose the catheters to which they are attached so as to promote visualization of the distal extremity of flexible cannula 19" and the distal and proximal extremity of inflatable balloon 27'.

Another embodiment of an arterial perfusion catheter of this invention is shown in FIG. 18. In the embodiment shown in FIG. 18, the distal tip 28" of first flexible cannula 19" has a plurality of distal orifices 36" which communicate with third lumen 88' that provides a flow path for blood suctioned from the left ventricle to the cardiopulmonary bypass pump. The aortic valve 93 is shown in phantom and arterial venting orifices 91' are shown to be located on the opposite side of the aortic valve from distal orifices 36". The arterial venting orifices 91' communicate with first arterial lumen 38" which may be selectively placed in communication with a cardioplegia pump or an aspiration pump such that cardioplegia solution may be delivered through orifices 91' or blood may be vented through the orifices into the first lumen for delivery to the intake side of the cardiopulmonary bypass pump.

To position first flexible cannula member 19" and second flexible cannula 21" in the aorta, a wire 94 is first advanced through an arterial vessel in communication with the aorta and extended across the aortic valve into the left ventricle. First flexible cannula member 19" is advanced over wire 94 until distal tip 28" is positioned in the left ventricle. As can be seen in FIG. 18 first flexible cannula member 19" is slideably mounted to second cannula member 21" such that the distance between inflatable balloon 27" and the tip of the first flexible cannula member may be selectively controlled. Thus, after first flexible cannula member 19" is advanced over wire 94 into the left ventricle, inflatable balloon 27" may be selectively positioned and thereafter inflated by injecting a saline or other solution through second arterial lumen 46"; second arterial lumen 46" communicates with a multiplicity of inflation ports 44" which communicate with the interior region of inflatable balloon 27". As in previous arterial perfusion catheter embodiments described above, inflatable balloon 27" has sensors 61" and 62" for delineating the distal and proximal ends of the balloon for positioning the balloon in the aortic arch cephalid of the aortic root. Thus, after the balloon is in position and inflated the arterial venting orifices 91' will be positioned adjacent the aortic root such that cardioplegia solution may be injected through the orifices and flow into the coronary arteries to stop the heart.

Advancing a catheter over a wire to guide a catheter through a vascular vessel is well known in the prior art. This catheter device, however, permits the tip of the catheter to be positioned in the left ventricle where blood may be suctioned through the multiplicity of orifices 36". The catheter allows blood in the left ventricle to be vented while at the same time blood present in the aortic root may also be vented through arterial venting orifices 91'. The cardioplegia solution may thereafter be infused through arterial venting orifices 91' and the solution will flow into the coronary arteries and stop the heart.

Referring now to FIG. 19, another embodiment of an arterial perfusion catheter of this invention is shown which may be positioned in the aorta by the use. of sensors or positioned by advancing the catheter over guide wire 94. However, unlike the embodiment of FIG. 18, in this embodiment, the arterial inflatable balloon 27''' is at a fixed distance from the distal end 28''' of first flexible cannula member 19'''. The positioning of this embodiment of the invention in the aorta is illustrated in FIG. 15. First flexible cannula member 19''' has second openings 96 that communicate with third lumen 88" which in turn communicates with arterial decompression port 97 thus providing a passageway for blood vented from the left ventricle. The vented blood is carried to the left ventricle decompression/vent roller pump from which the blood is pumped to the venous reservoir of the cardiopulmonary bypass pump. Likewise, a multiplicity of arterial venting orifices 91" communicate with first arterial lumen 38''' and provide a flow path for the cardioplegia solution to be injected into the aortic root and also provide a flow path for the venting of blood from the aortic root which is carried as in the previous embodiments of the arterial catheters to the suction roller pump. The blood is then pumped to the bubble oxygenator and heat exchanger of the arterial reservoir of the cardiopulmonary bypass pump. Second lumen 146 communicates with inflation ports 44''' which in turn communicate with the inferior region of inflatable balloon 27'''. An inflation source 25 (shown in FIG. 38) is utilized to inflate balloon 27''' after it is positioned in the aorta.

Figure 20:
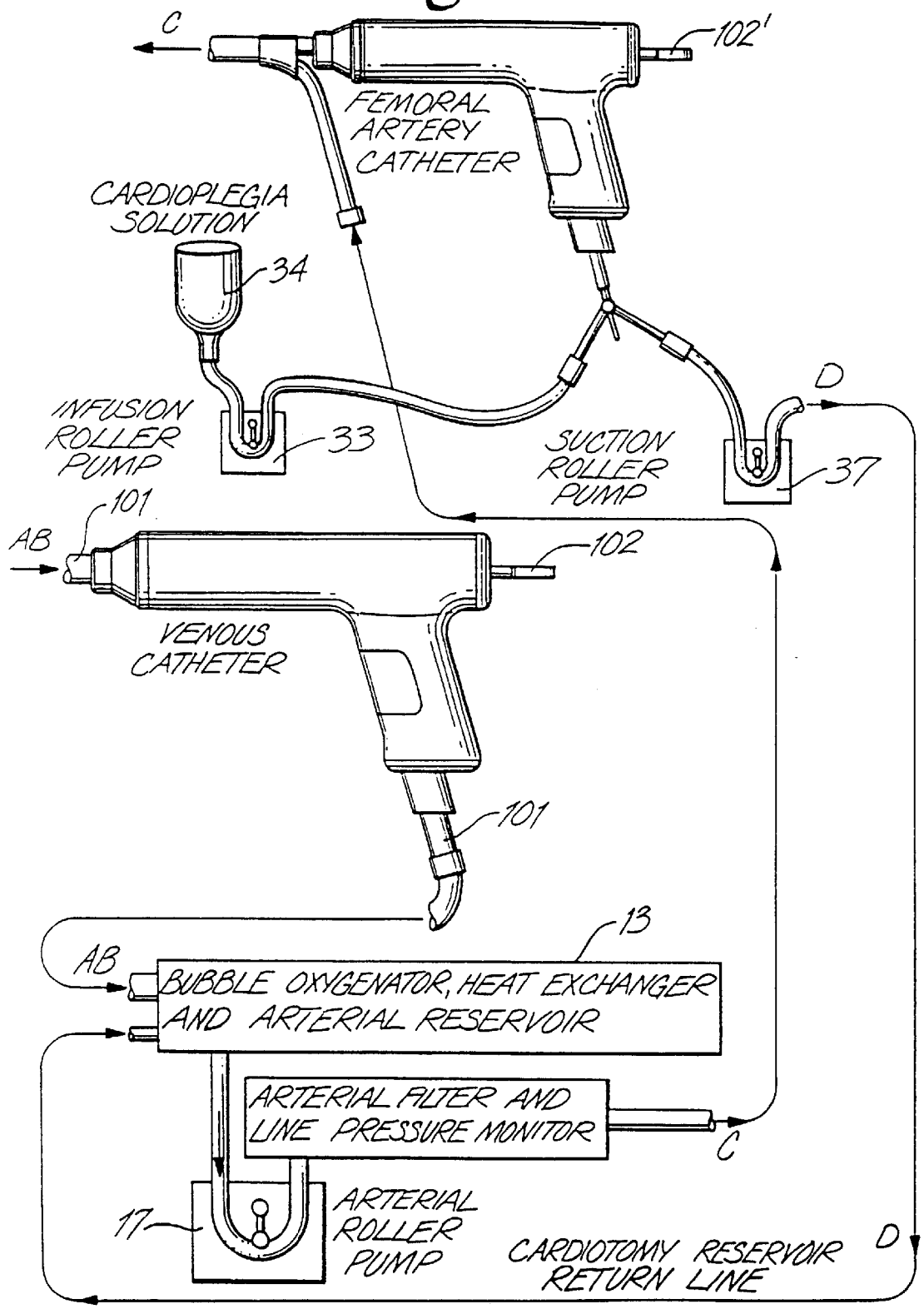
FIG. 20 is a schematic view illustrating a femoral artery catheter and venous catheter system for achieving cardiopulmonary bypass.

FIG. 20 is a schematic view illustrating a system of venous perfusion and arterial perfusion catheters for use in obtaining total cardiopulmonary bypass support and isolation of the heart; however, the system shown in FIG. 20 utilizes an arterial perfusion catheter which is advanced through the femoral artery. Any of the embodiments of venous perfusion catheters previously described may be utilized with this type arterial catheter and the descriptions of venous catheters detailed above may be incorporated for explanation purposes to obtain partial or total bypass.

FIGS. 21 through 30 illustrate arterial perfusion catheter embodiments of this invention to be advanced through the femoral artery and thereafter positioned such that an expander or balloon may be inflated to occlude the aorta cephalid of the aortic root and oxygenated blood then delivered through the catheters into arterial circulation. As in the above-described arterial perfusion catheter embodiments of this invention, the femoral artery catheters also deliver a cardioplegia solution to arrest the heart, provide for venting the aortic root through the same flow channel, and in certain embodiments provide for the distal tip of the catheter to extend into the left ventricle across the aortic valve to permit decompression of the left ventricle before the right atrium is isolated by inflation of the inflatable balloons carried by the venous perfusion catheter.

Referring now to FIG. 20, this catheter system incorporates a venous catheter 101 which is inserted peripherally into the femoral vein and advanced through the femoral vein by the steering mechanism controlled by joy stick 102. As can be seen, the schematic shown in FIG. 20 is identical to the schematic show in FIG. 1; however, the catheter system utilizes a femoral artery perfusion catheter. By referring to FIG. 21 it can be seen that the venous perfusion catheter illustrated in FIG. 21 is identical to the venous perfusion catheter illustrated in FIG. 3. In view of the catheter similarity, the description of the venous catheter in FIG. 3 will be incorporated into the description of the venous catheter shown in FIG. 21. Similarly, the schematic of the arterial catheter shown in FIG. 1 is identical to the schematic shown in FIG. 20 with the exception that the arterial perfusion catheter referred to in FIG. 20 is a femoral artery catheter. With this exception, the previously set forth schematic description of FIG. 1 is incorporated into FIG. 20.

Referring now to FIG. 21, femoral arterial perfusion catheter 118 has a first flexible cannula 119 and a second flexible cannula 121 where first flexible cannula 119 is slideably carried by second cannula 121. As in previous arterial perfusion catheter embodiments, femoral arterial perfusion catheter 118 has an inflatable balloon 127 attached to first flexible cannula member 119 adjacent its distal tip 128 where distal tip 128 has a plurality of orifices 136 for delivering a cardioplegia solution into the coronary arteries for arresting the heart. To deliver oxygenated blood into arterial circulation, second flexible cannula 121 has multiplicity of first openings 124 through which the oxygenated blood (as shown by arrow c in FIG. 21) is pumped by arterial roller pump 17 (FIG. 20). Blood may also be vented from the aortic root through a multiplicity of orifices 36 in the distal tip 124 of first flexible cannula 119 and returned to the arterial reservoir of the pump.

To position inflatable balloon 127 in the ascending aortic arch 123, the femoral perfusion catheter 118 is inserted through the femoral artery (preferably through an incision made in the groin area) and both the first flexible cannula 119 and second flexible cannula 121 are advanced through the femoral artery until the second flexible cannula is positioned in a region which is located proximally of the descending aorta; first flexible cannula 119 is thereafter advanced through the aortic arch and balloon 127 positioned in the aortic root cephalid of the junction of the coronary arteries where its location is determined by ultrasound or radiographic techniques which are well known in the prior art.

Referring now to FIG. 22, it can be seen that femoral arterial perfusion catheter 118, as in previous embodiments of arterial perfusion catheters of this invention, is carried by the handpiece 51 was described in FIGS. 4, 8 and 16; the structure of handpiece 51, therefore, which was described in those figures, is incorporated into FIG. 22 by reference. Referring again to FIG. 22, it can be seen that first flexible cannula 119 has a first arterial lumen 138 which communicates with the multiplicity of orifices 136 in the distal tip 128 of flexible catheter 119. First arterial lumen 138 communicates at its proximal end with first proximate port 143. The proximal end of first flexible cannula member 119 is connected to a connector switch 139 which permits selective communication between first lumen 138 and infusion roller pump 34 or suction roller pump 37, respectively, through selection of either cardioplegia connector 141 or aspiration connector 142. (As previously described in FIG. 4, both the cardioplegia connector 141 and the aspiration connector 142 communicate with first proximate port 143 such that first lumen 138 may selectively provide a fluid passage for the delivery of cardioplegia solution to distal orifices 136 or to permit the aspiration of blood from the aortic root cephalid of the junction of the coronary arteries.) Occlusion of the aortic arch cephalid of the coronary artery junction (and thus isolation of the left ventricle of the heart) is accomplished by positioning inflatable balloon 127 in the aortic root and thereafter inflating the balloon to occlude the aorta. Inflation of balloon 127 is achieved through the use of a saline solution or other fluid infused through second lumen 146 contained in first flexible cannula 119. Second lumen 146 communicates with the interior region of inflatable balloon 127 through a multiplicity of inflation ports 144 and the saline solution is injected through arterial inlet port 147 which communicates with second lumen 146.

Distal tip 128 of flexible cannula 119 is tapered to accommodate and promote ready passage through the femoral artery and is preferably made of a reflective plastic material to assist in establishing the image of the tip ultrasonically at the proximal end of inflatable balloon 127. Imaging is also achieved by use of circumferentially extending sensor 161 carried by first flexible cannula 119 where the sensor may be made of a plastic or other suitable material reflective of ultrasonic waves, or coated with a piezoelectric material or a radiopaque material to permit fluoroscopic positioning of the proximal end of the balloon. The position of a reflective sensor or radiopaque marker is illustrated in FIG. 23.

FIG. 23 is an exploded representation of the distal portion of femoral arterial perfusion catheter 118 and FIG. 25 is a cross-section of the right portion of FIG. 23 taken along the lines 23—23. Referring now to FIG. 23, it can be seen that second flexible cannula 121 has an axially extending first arterial cavity 148 which communicates with a multiplicity of openings 124. The proximal end of second flexible cannula 121 contains a connector 149 by which the second flexible cannula is connected to the cardiopulmonary bypass pump. First arterial cavity 148 communicates with the cardiopulmonary bypass pump and with multiplicity of openings 124 to permit oxygenated blood to be pumped from the cardiopulmonary bypass pump to arterial circulation. FIG. 24 is a left side view of FIG. 23 and illustrates inflatable balloon 127 in phantom lines. A bottom view of femoral arterial perfusion catheter 118 is shown in FIG. 26 and illustrates the multiplicity of openings 124 which accommodate blood flow from first arterial cavity 148 into arterial circulation.

By referring to FIGS. 22 and 25, it can be seen that steering wires 159 axially extend through steering lumens 158 to permit the distal tip 128 of first flexible cannula member 119 to be articulated within the femoral artery and to steer the distal tip through the aortic arch for positioning inflatable balloon 127 cephalid of the aortic root. Steering wires 159 are carried by first flexible cannula 119 and pass through steering lumens 158 for connection to steering mechanism 63 which is shown in FIGS. 28 and 29 and will be more specifically described below.

Another embodiment of the femoral arterial perfusion catheter is shown in FIG. 27. This embodiment permits the distal tip of the first flexible cannula to advance through the aortic valve and into the left ventricle where blood from the left ventricle may be vented while at the same time, on the cephalid side of the aortic valve, a cardioplegia solution may be injected into the aortic root for flow into the coronary arteries to arrest the heart. Referring again to FIG. 27, it can be seen that the distal tip 128' has a multiplicity of orifices 136' through which blood may be vented from the left ventricle. At the distal end of balloon 127', the multiplicity of venting orifices 191 located adjacent to inflatable balloon 127' permit either the infusion of the cardioplegia solution or venting of the aortic root. The distal portion of flexible cannula 119' extending between the balloon 127' and distal tip 128' contains both the multiplicity of venting orifices 191 and the multiplicity of orifices 136'. Thus, the distal tip is sufficiently spaced from the orifice 191 to permit the simultaneous venting of both the aortic root and the left ventricle of the heart. This spacing may be a predetermined fixed distance as shown in FIG. 19. Alternatively, as shown in FIG. 18 inflatable balloon 127' may be carried by second flexible cannula 121 to permit slideable movement between the distal tip portion 128' of first flexible cannula member 119' and second flexible cannula member 121'. The structure of the distal portion as described in FIG. 18 is incorporated into this embodiment of the femoral arterial perfusion catheter to permit the slideable extension of the distal tip 128' through the aortic valve. Similarly, the structure shown in FIG. 19 is incorporated into the femoral arterial perfusion catheter where the distal tip 128' is at a fixed distance from the inflatable balloon 127'.

The steering mechanism 63 carried by handpiece 51 is illustrated in FIGS. 28 and 29. Handpiece 51 may be used with either the arterial perfusion catheters or the venous perfusion catheters described above. As can be seen in FIG. 28, joy stick 2 can be pivoted either in the horizontal plane or in the vertical plane (shown by arrows XX' in the horizontal plane and YY' in the vertical plane). Joy stick 2 comprises a shaft member 151 which may be pivoted horizontally about pivot pin 52 and the shaft 151 passes through an axially extending slot 53 which is contained in pivot shaft 154. Pivot shaft 154 is pivotally mounted to the handpiece 51 such that pivot shaft 154 may rotate about its longitudinal axis 155 thereby permitting movement of the joy stick 2 in the vertical plane as shown by the arrows YY'. Joy stick shaft member 151 has opposing planar regions 156 and 156' which extend through slot 53 and terminate in a L-shaped shoulder 157 that engages a like dimensioned groove 163 in threaded shaft 164. A mounting plate 166 threads onto threaded shaft 164 and carries mandrills 167 about which the steering wires 159 are respectively wound.

Referring to FIG. 29, mandrill 167 is captively held between a pair of molded locking wedges 168 and 169 which are mirror images of each other. The locking wedges 168 and 169 have transversely extending rods 168' and 169', which when joined together, capture the steering wire 159. The wedges when joined are inserted into longitudinally extending bores 171 contained in mounting plate 166. Thus, to create the tension in steering wires 159 to enable the joy stick to steer the catheter, steering wires 159 are first inserted through bores 171 and then wrapped about mandrill 167. Mandrill 167 is thereafter clamped between locking wedges 168 and 169 and rods 168' and 169' are then inserted into axially extending bores 171. Tension is then achieved in steering wires 159 by tightening nut 172 onto the threaded end of threaded shaft 164. Since the housing 20 is locked between the opposing mating frames 54 and 56 of the handpiece 51, a tightening of nut 172 will create tension in the steering wires.

Referring now to FIGS. 35, 36 and 37, the distal end of a catheter (for illustration purposes identified by numerical 19) is shown and the structure illustrated for securing guide wires 159 to the distal tip of the catheter. FIG. 37 illustrates a clamping ring 172 which has a distal surface 173 that contains four equally spaced notches 174 and four equally spaced openings 176 which are located intermediate distal surface 173 and proximate surface 177 of clamping ring 172. As can be seen in FIG. 37, to anchor the steering wire 159, it is threaded through a respective opening 176 and then looped about the distal surface 173 after which it is again inserted through a respective opening 176. Referring again to FIG. 35, it can be seen that the clamping ring 172 is captively held in the distal tip 28 of the first flexible cannula; distal surface 173 of the clamping ring bears against shoulder 178 of the tip and the proximal surface 177 of the clamping ring bears against the distal transverse wall 179 of first flexible cannula member 19. First flexible cannula member 19 and the distal tip 28 are bonded together by the sensor member 180. Thus, by horizontal movement of the joy stick 2, opposing steering wires 159 will experience different tensions and therefore the tip 28 of the catheter can be articulated horizontally. Similarly, by movement of the joy stick in the vertical plane opposing steering wires 159 will experience different tensions and the tip of the catheter may be made to articulate in the vertical direction.

Figure 31:
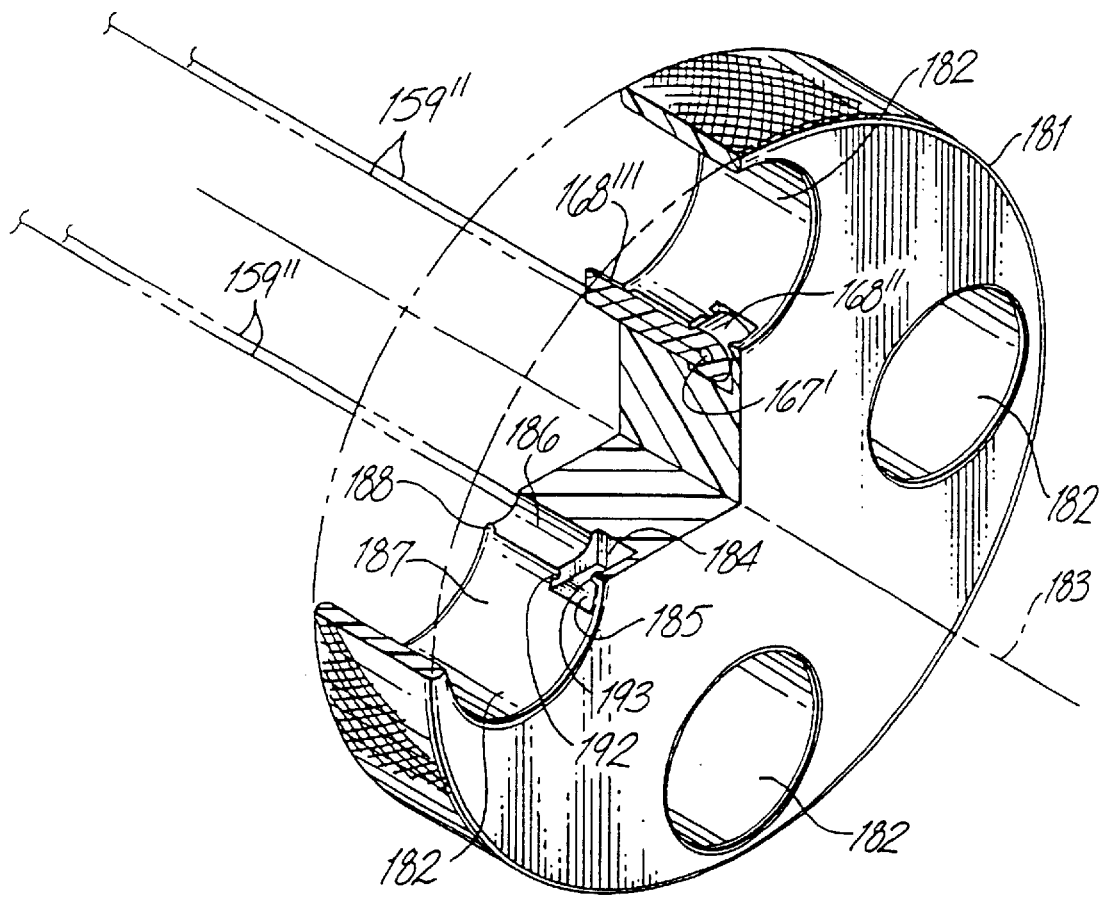
FIG. 31 is a part cross-sectional perspective view of the embodiment of the steering mechanism of this invention shown in FIG. 30.

Another embodiment of a steering mechanism is shown in FIGS. 30, 31, 32 and 33. FIG. 31 is a perspective view of a control plate 181 which is hand manipulated to obtain tension in steering wires 159". Control plate 181 is preferably made of a plastic material and has four cylindrical gripping holes 182 at equal angular spacings about central axis 183. This embodiment of the steering mechanism also utilizes an opposing pair of locking wedges 168" and 169" which have extending therefrom rods 168'" and 169'". The steering wire 169" is wrapped about the mandrill 167' which is then captively held between the respective locking wedges. To permit the insertion of the assembly of the locking wedge, mandrill, and steering wire into the control plate 181, a radially extending slot 184 with an opening 185 in the surface of cylindrical gripping holes 182 is utilized. An axially extending cavity 186 has a diameter slightly larger than the assembled diameter of the opposing rods 168'" and 169'" and cavity 186 intersects the inner surface 187 of cylindrical gripping holes 182 thereby forming an axially extending opening through which the assembled rods may be inserted. A retention clip 188 retains the assembled rods in cavity 186 after insertion. The locking wedges 168" and 169" likewise insert into radially extending slot 184 and are mounted by forcing the locking wedges through opening 185 in a radial direction and the locking wedges are held in radially extending slot 184 by retaining clips 192 and 193. By referring to FIGS. 32 and 33, the orientation of the locking wedges 168" and 169" and the assembled rods 168'" and 169'" can be seen after the assembly is mounted to the control plate 181. By referring to FIG. 30, the connection of the control plate to the catheter wires 159" is further illustrated where it can be seen that steering wires 159" emerge from first flexible cannula housing 20 through ports 194 and 195.

The structure above described and illustrated in FIG. 31 is incorporated into FIG. 34 which is an illustration of the steering wires 159" acting as conductors for signals generated by an ultrasound source acting on a piezoelectric sensor.

Figure 42:
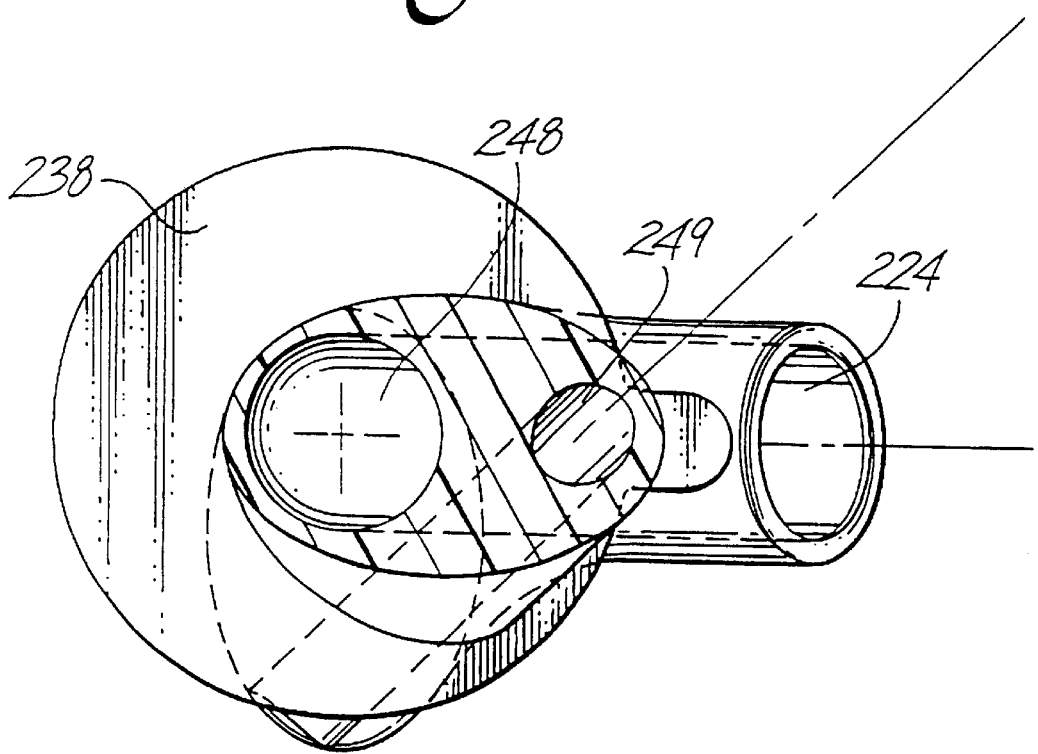
FIG. 42 is a part cross-sectional view taken along the lines 42—42 of FIG. 41.

Yet another, further, embodiment of this invention relates to an arterial perfusion catheter which may be inserted directly into the aorta minimally invasively. This technique first requires inserting a thorascope through a 12 mm incision made between the 4th and 8th intercostal space where the thorascope is used to identify the descending thoracic aorta and distal arch. The thorascope is further utilized to obtain an actual image of the cardiac anatomic structure which assists the surgeon in fashioning a pair of circular tourniquet purse string sutures at the sight selected for insertion of the catheter into the descending thoracic aorta. After the purse string sutures are fashioned, a side-biting vascular clamp is then applied to occlude and isolate the insertion sight from the rest of the aorta. This maneuver prevents bleeding when the catheter is advanced through a hole made in the center of the purse strings. After the catheter is advanced through the hole, the tourniquets are drawn taut to snugly seal the aortic tissue around the catheter entry site and the side-biting vascular clamp is thereafter removed. To retain the rigidity of the arterial perfusion catheter during insertion of the catheter through the descending thoracic aorta, a stylet (which is shown in phantom on FIG. 42) is utilized. Stylet 197 may be made of a stainless steel or other material of sufficient rigidity to enable the surgeon to insert the catheter through the incision which has been made in the center of the purse string sutures.

FIG. 39 illustrates the 4th innercostal space 198 through which the arterial perfusion catheter 218 is inserted into the descending thoracic aorta 199. As can be seen in FIG. 39, arterial perfusion catheter 218 has a first flexible cannula 219 and a second flexible cannula 221. First flexible cannula 219 as in the previous embodiments described above of the arterial perfusion catheter embodies an inflatable balloon 227 which is utilized to occlude the ascending aorta 223 above the junction of the coronary arteries 220 cephalid of the aortic root 222. The structure of first flexible cannula 219 is identical to the arterial perfusion catheter structures for the first flexible cannula which have been described above. As can be seen in FIG. 39, the distal portion of flexible cannula 219 in part extends beyond the mitral or aortic valve 225 into the left ventricle 230. At the distal tip 228 there are a multiplicity of venting orifices 236 for venting blood from the left ventricle after the venous perfusion catheters have been positioned and the cardiopulmonary bypass pump activated. The distal portion of first flexible cannula 219 is comparable to that described in FIG. 19. A first sensor 229 is spaced adjacent to and proximally of venting orifices 236; and a second sensor 230 is located adjacent to inflatable balloon 227 and proximally of arterial venting orifices 291. Arterial venting orifices 291 communicate with the first lumen of first flexible cannula member 219 (the first lumen being shown as 38'" in FIG. 19) and are utilized for the injection of a cardioplegia solution into the aortic root or alternatively for the venting of blood from the aortic root cephalid of the aortic valve 225. First and second sensors 229 and 230 may be made of a brass bead material covered by a piezoelectric coating or they may be made of a material reflective of ultrasound. The sensors may also be radiopaque markers for positioning the balloon and for identifying the location of the venting orifices 236 fluoroscopically.

Figure 43:
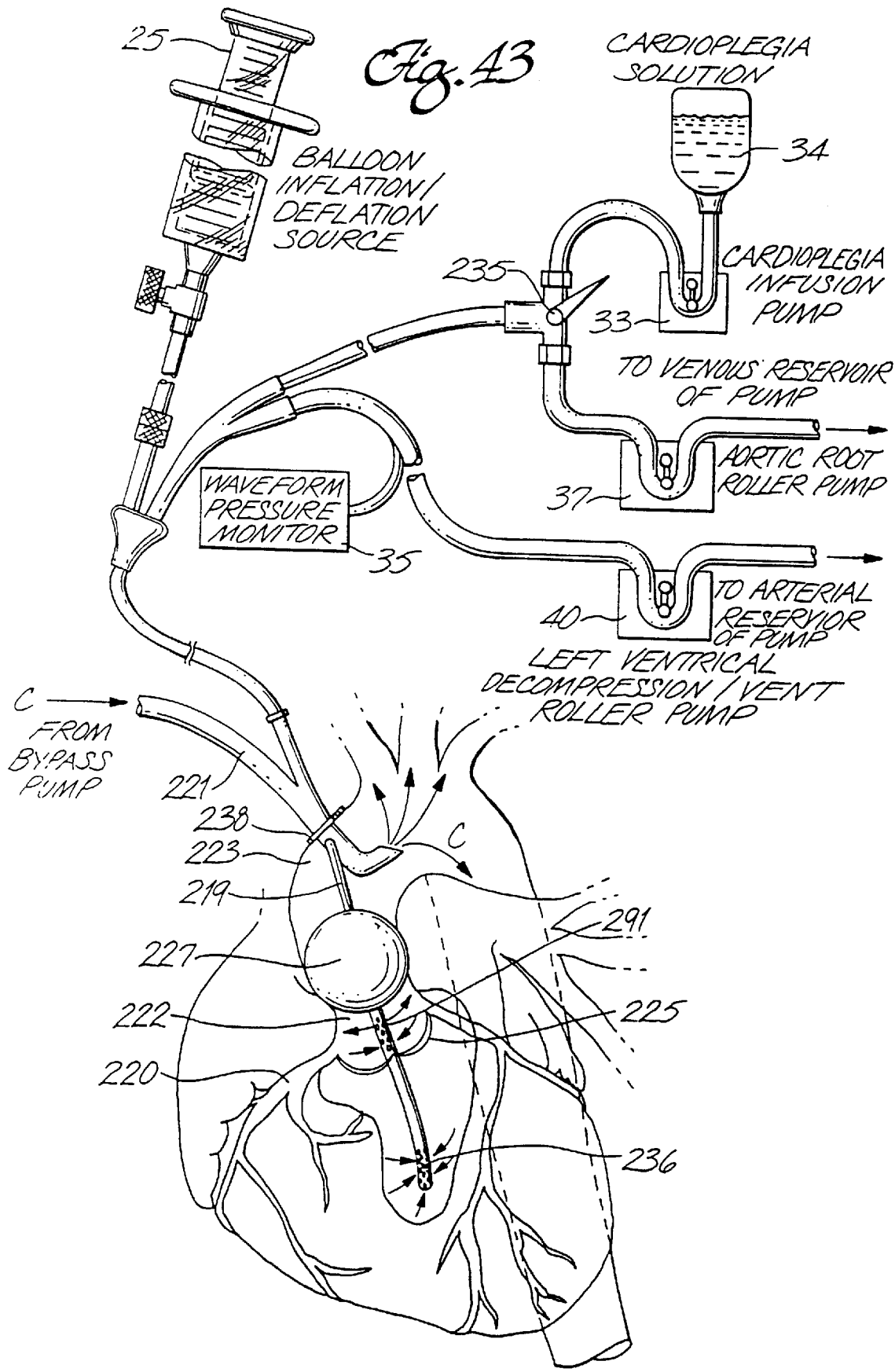
FIG. 43 is a schematic illustration of another embodiment of an arterial perfusion catheter of the catheter system of this invention.
Figure 44:
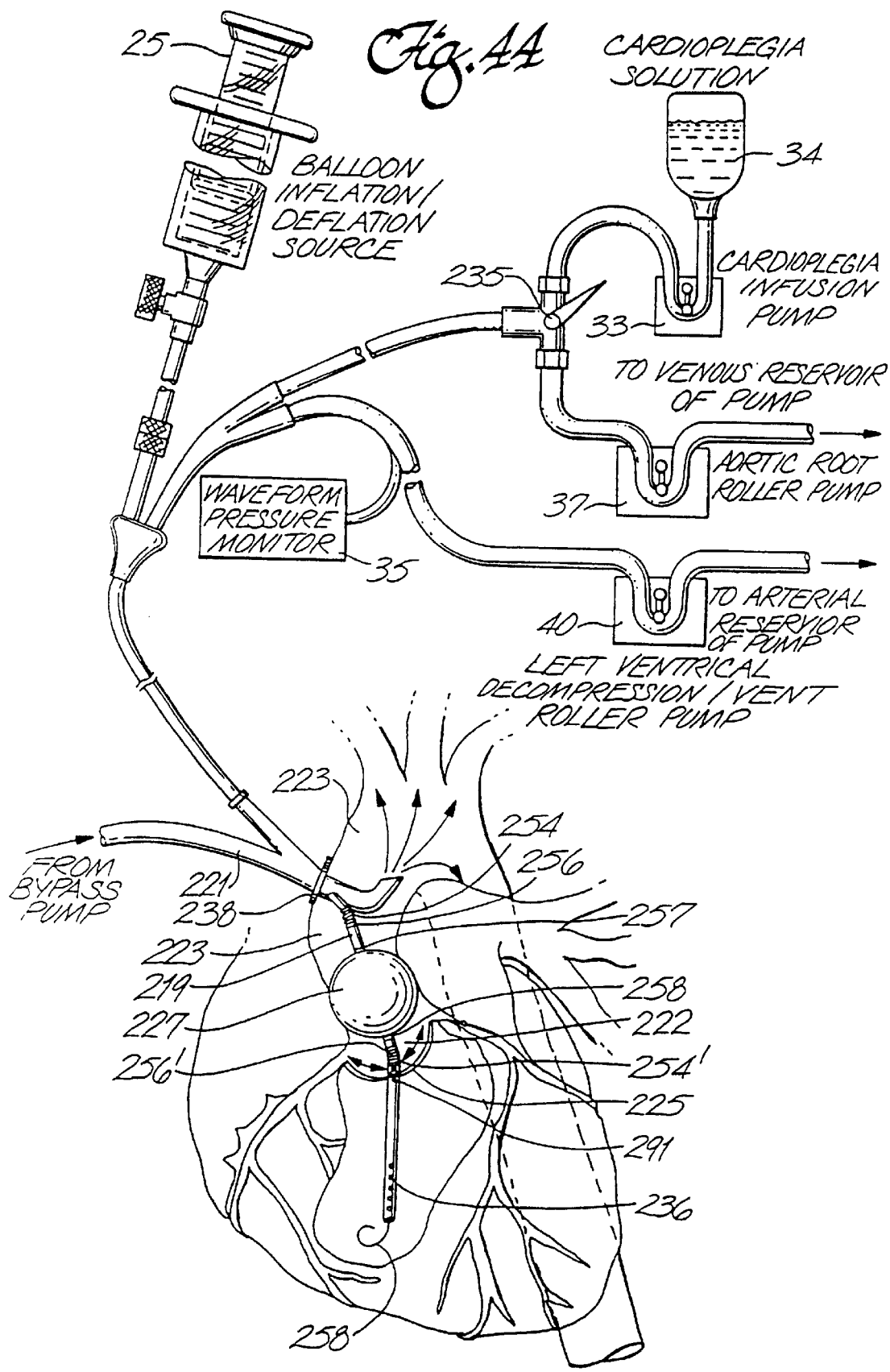
FIG. 44 is a schematic illustration of yet another embodiment of an arterial perfusion catheter of the catheter system of this invention.

Referring now to FIG. 38, a schematic presentation illustrates the elements of the arterial perfusion catheter circuit. These elements provide for injection of cardioplegia solution, venting of the aortic root, balloon inflation and deflation, arterial circulation blood from the bypass pump, and left ventricle decompression. FIGS. 43 and 44 are schematic illustrations of arterial perfusion catheters identical to that disclosed in FIG. 38, however, in FIGS. 43 and 44, the arterial perfusion catheter is inserted into the ascending aortic arch after a sternotomy has been performed and the heart exposed. Thus, the illustration in FIG. 43 differs from that in FIG. 38 by the location of the insertion of the catheter into the aorta. This illustration is representative of a technique which can be utilized if the heart has been exposed through a sternotomy or thoracotomy. By referring again to FIG. 38, the circuit for the arterial perfusion catheter illustrates the cardioplegia solution 34 being in communication with the cardioplegia infusion pump 33 which in turn communicates with selector switch 235. Selector switch 235 allows the surgeon to selectively introduce cardioplegia solution into the aortic root through venting orifices 291 or to suction the aortic root where blood is suctioned by aortic root roller pump 37 and delivered to the arterial reservoir of the cardiopulmonary bypass pump. As schematically shown in FIG. 38, a wave form pressure monitor 35, a device well known in the prior art, may be used to position the inflatable balloon 227 in the aortic root 222 by monitoring the characteristic pressure wave forms transported by the third lumen (as shown in FIG. 19) to a display monitor. Blood which is suctioned through arterial venting orifices 236 is returned by the third lumen (88" of FIG. 19) to the arterial reservoir of the cardiopulmonary bypass pump by left ventricle decompression roller pump 40. Oxygenated blood as shown by arrow c is then pumped from the bypass pump through the second flexible cannula 221 to arterial circulation. The balloon inflation/deflation source 25 is shown in communication with first flexible cannula 219 and communicates with a second arterial lumen (146 of FIG. 19) for the delivery of the saline solution or other fluid to inflate and deflate inflatable balloon 227.

FIGS. 39, 40, 41 and 42 illustrate in greater detail the second flexible cannula 221. Second flexible cannula 221 requires for insertion first placing purse string sutures into the descending thoracic aorta 199 or the ascending aorta and thereafter pushing the flexible cannula with stylus 197 in part into the aorta as shown in FIGS. 43 and 44. A perspective view of the distal end of the second flexible cannula 221 is illustrated in FIG. 40. As can be seen in FIG. 40, second flexible cannula 221 has a distal tip 226 having a first opening 224 for delivering oxygenized blood to arterial circulation. First opening 224 communicates with first arterial cavity 248 which in turn communicates with the outlet of the cardiopulmonary bypass pump. A second arterial cavity 249 extends angularly through the housing 251 through which first arterial cavity 248 also extends; first and second arterial cavities 248 and 249 are sufficiently spaced within housing 251 to preclude communication between them. Second arterial cavity 249 is constructed to receive first flexible cannula 219 and provide a path through which first flexible cannula 219 may be advanced to position inflatable balloon 227 in the aortic arch and to position arterial venting orifices 291 and 236 in relationship to the mitral or aortic valve. First flexible cannula 219 emerges from the housing 251 through opening 252 which lies within the aorta after the distal portion of the housing is inserted through the aortic tissue 237. As above-described, the distal portion of housing 251 is inserted through an incision made in the aortic tissue after a pair of purse string sutures have been inserted into the tissue. The purse string sutures are tightened after the distal portion of the housing is inserted through the aortic incision in a tourniquet fashion to prevent leakage of blood through the aortic wall. A grommet seal 238 sealingly surrounds the housing 251 and has a distal surface 253 bearing against the aorta which not only prevents further advancement of the distal portion of second flexible cannula 221 into the aorta but also acts as a further seal to prevent leakage of blood from the aorta through the purse string sutures. By referring to FIG. 42, a cross-sectional view taken in the direction of the lines 42—42, the non-communication of first arterial cavity 248 and second arterial cavity 249 is further illustrated.

Another modification or embodiment of the arterial perfusion catheter 221 is shown in FIG. 44. In this embodiment, first flexible cannula 219 has a region of flexion 254 located adjacent to and proximally of inflatable balloon 227. Region of flexion 254 has less flexural rigidity due to a series of accordian-like serrations 256. Similarly, adjacent to and slightly distally of inflatable balloon 27 a second region of flexion 254' is utilized to enhance the bending of first flexible cannula 219. This promotes the adaptation of the distal portion of first flexible cannula 219 distally of the aortic valve 225. The second region of flexion 254 also contains a series of serrations 256' to enhance the bending of first flexible cannula 219 distally of inflatable balloon 227.

Sensors 257 and 258 are carried by first flexible cannula 219 adjacent the proximate and distal ends of balloon 227. The sensors as above-described, are used to locate and position inflatable balloon 227 in the aorta as the first flexible cannula is advanced through the housing 251 of the second flexible cannula. An alternative method for advancing first flexible cannula 219 across the aortic valve 225 and into the left ventricle of the heart is provided by a wire 258 over which the first flexible cannula may be advanced as more definitively described and shown in FIG. 19.

The method therefore for providing cardiopulmonary bypass pump support during heart surgery requires the insertion of a venous perfusion catheter through a peripheral vein access site and thereafter positioning the distal venous return ports of the catheter in the superior and inferior vena cava at the atrio-caval junction. The venous perfusion catheter contains inflatable occlusion balloons that allow the choice of either partial or total cardiopulmonary bypass support. Total bypass support would occur if the balloons completely occluded both the inferior and superior vena cava thereby preventing blood flow into the right atrium. An insertion site for the venous perfusion catheter may be the femoral vein, iliac vein, subclavian vein, axillary vein, or internal jugular vein. Insertion of the catheter through a peripheral vein access site avoids the necessity for a major chest incision to expose the heart as well as to eliminate the surgical trauma which would occur to the right atrium, superior vena cava, and inferior vena cava. This procedure also eliminates costly surgical instruments, sutures, tourniquets, and reduces the operative time associated with conventional approaches to cardiopulmonary bypass. To provide blood into arterial circulation, an arterial perfusion catheter is inserted peripherally into arterial vessels which permit the first flexible cannula portion of the arterial perfusion catheter to be advanced through the vessel into the ascending aorta. In one method of this invention, the arterial perfusion catheter carries an inflatable balloon proximately of the distal tip of the catheter for occluding the aorta after the balloon is positioned in the ascending aorta cephalid of the junction of the coronary arteries in the aortic root. The arterial catheter is then connected to the cardiopulmonary bypass pump which is then activated to permit oxygenated blood to be delivered to arterial circulation and the left ventricle decompression pump also activated. The inflatable balloon carried by the arterial perfusion catheter is then inflated to sufficiently occlude the passage of blood from the aortic root into systemic arterial circulation and the cardioplegia solution is then infused into the aortic root to arrest the heart. By thereafter inflating the second and first balloons of the venous perfusion catheter sufficiently to preclude blood flow from the inferior and superior vena cava into the right atrium, total cardiopulmonary bypass support is achieved. (Partial inflation so as not to completely occlude the vena cava would result in partial bypass support.)

Another method for providing cardiopulmonary bypass pump support during heart surgery includes inserting a first arterial catheter into a preselected arterial vessel where the catheter is advanced within the vessel into the aortic arch. The arterial catheter carries an inflatable balloon located near the tip of the catheter for occluding blood flow from the left ventricle into arterial circulation. A second arterial perfusion catheter may be then inserted into a second preselected arterial vessel and advanced into the aortic arch where the second arterial perfusion catheter has preselected openings at its distal end for delivering blood to arterial circulation from the cardiopulmonary bypass pump. The first arterial catheter is positioned such that the balloon is located cephalid of the junction of the coronary arteries with the aortic root. The venous perfusion catheter is then positioned such that the inflatable balloons carried by the catheter may be inflated to compelete occlude the inferior and superior vena cava thereby precluding blood flow into the right atrium. The second arterial catheter is then connected to the cardiopulmonary bypass pump and the venous catheter is connected to the inlet side of the pump. The bypass pump is then activated and the left ventricle decompression pump activated and the inflatable balloon carried by the arterial perfusion catheter is sufficiently inflated to occlude the passage of blood from the aortic root into systemic arterial circulation. Cardioplegia solution is then infused into the aortic root to arrest the heart and the aortic root is then vented. The two balloons carried by the venous perfusion catheter are then inflated sufficiently to occlude the superior and inferior vena cava respectively thereby isolating the right atrium, and the heart, thus establishing total cardiopulmonary bypass support.

Yet another method to obtain total cardiopulmonary bypass although not described or illustrated in the drawings, is to insert two venous perfusion catheters into preselected veins where the purpose of one of the catheters would be to inflate a distal balloon which would occlude the superior vena cava and redirect the blood flowing towards the right atrium of the heart by appropriate orifices located proximally of the inflated balloon back to the arterial reservoir of the cardiopulmonary bypass pump. A second catheter would be utilized to occlude the inferior vena cava where the second catheter would have orifices located proximally of the balloon for intercepting blood flow into the right atrium and redirecting it toward the arterial reservoir of the cardiopulmonary bypass pump.

The methods of this invention to achieve cardiopulmonary bypass support all include the use of venous perfusion catheters remotely insertable into the veins. Preferably, the insertion would be into the femoral vein and the catheter then advanced and positioned at the atrio-caval junction by ultrasound or radiopaque techniques.

To achieve delivery of blood into aterial circulation, arterial perfusion catheters may be inserted peripherally into arterial vessels and then advanced and positioned in the aorta or directly inserted into the aorta by utilizing purse string sutures. Either insertion technique of the arterial catheter would require both a cardioplegia solution to be delivered to the coronary arteries to arrest the heart and an aortic root vent pump. A feature of the arterial perfusion catheters would allow the distal tip of the catheter to transverse the aortic valve where the distal tip has a multiplicity of openings for venting the left ventricle.

While certain embodiments of the present invention relating to systems and methods for providing cardiopulmonary bypass pump support during heart surgery have been described, it is to be understood that they are subject to many modifications without departing from the spirit and scope of the claims as recited herein.

What is claimed is:

1. A method of occluding a patient's ascending aorta and delivering oxygenated blood from a bypass system, comprising:

providing a femoral arterial perfusion catheter having an occluding member, a blood flow lumen and a plurality of blood flow outlets in fluid communication with the blood flow lumen, the occluding member being movable from a collapsed shape to an expanded shape;

introducing the femoral arterial perfusion catheter into a patient's femoral artery;

positioning the occluding member in the patient's ascending aorta and the plurality of blood flow outlets in the descending aorta;

moving the occluding member from the collapsed shape to the expanded shape;

coupling the blood flow lumen to a source of oxygenated blood; and infusing oxygenated blood into the patient's descending aorta through the blood flow lumen and the plurality of blood flow outlets.

2. The method of claim 1, further comprising the steps of:

providing the femoral arterial perfusion catheter with a cardioplege lumen;

coupling the cardioplege lumen to a source of cardioplegic fluid; and infusing cardioplegic fluid into the patient's aortic root though the cardioplege lumen.

3. The method of claim 2, further comprising the step of:

venting the patient's aortic root through the cardioplege lumen.

4. The method of claim 1, wherein:

the providing step is carried out with the femoral arterial perfusion catheter having a first cannula and a second cannula slidably coupled to the first cannula, the first cannula having the occluding member and the second cannula having the blood flow lumen and the plurality of blood flow outlets.

5. The method of claim 1, wherein:

the second cannula has another lumen, the first cannula being slidably received in the another lumen of the second cannula.

6. The method of claim 1, wherein:

the providing step is carried out with the femoral arterial perfusion catheter has at least one wire embedded therein for steering a distal end.

* * * * *